United States Patent
Kwon et al.

(10) Patent No.: US 12,129,218 B2
(45) Date of Patent: Oct. 29, 2024

(54) AUTOTAC CHIMERIC COMPOUND, AND COMPOSITION FOR PREVENTING, AMELIORATING OR TREATING DISEASES THROUGH TARGETED PROTEIN DEGRADATION COMPRISING THE SAME

(71) Applicant: AUTOTAC INC., Seoul (KR)

(72) Inventors: Yong Tae Kwon, Seoul (KR); Chang Hoon Ji, Seoul (KR); Srinivasrao Ganipisetti, Seoul (KR); Hee Yeon Kim, Seoul (KR); Su Ran Mun, Seoul (KR); Chan Hoon Jung, Seoul (KR); Eui Jung Jung, Seoul (KR); Ki Woon Sung, Seoul (KR)

(73) Assignee: AUTOTAC INC., Seoul (KR)

( * ) Notice: Subject to any disclaimer, the term of this patent is extended or adjusted under 35 U.S.C. 154(b) by 919 days.

(21) Appl. No.: 17/262,157

(22) PCT Filed: Jul. 24, 2019

(86) PCT No.: PCT/KR2019/009205
§ 371 (c)(1),
(2) Date: Jan. 21, 2021

(87) PCT Pub. No.: WO2020/022785
PCT Pub. Date: Jan. 30, 2020

(65) Prior Publication Data
US 2021/0299253 A1    Sep. 30, 2021

Related U.S. Application Data

(60) Provisional application No. 62/702,473, filed on Jul. 24, 2018.

(51) Int. Cl.
*A61K 39/395*    (2006.01)
*A23L 33/10*    (2016.01)
(Continued)

(52) U.S. Cl.
CPC ............ *C07C 217/58* (2013.01); *A23L 33/10* (2016.08); *A61K 31/05* (2013.01); *A61K 31/12* (2013.01);
(Continued)

(58) Field of Classification Search
None
See application file for complete search history.

(56) References Cited

U.S. PATENT DOCUMENTS 4,167,581 A    9/1979    Smith
4,471,116 A    9/1984    Davidson et al.
(Continued)

FOREIGN PATENT DOCUMENTS

CN    102229602 A    11/2011
CN    107848932 A    3/2018
(Continued)

OTHER PUBLICATIONS

Bondeson et al., Nature Chemical Biology 2015, vol. 11, 2015, pp. 611-617 (Year: 2015).*

(Continued)

*Primary Examiner* — Karl J Puttlitz
(74) *Attorney, Agent, or Firm* — Sughrue Mion, PLLC

(57) ABSTRACT

The present invention relates to a novel AUTOTAC chimeric compound in which a new p62 ligand and a target-binding ligand are connected by a linker, a stereoisomer, hydrate, solvate or prodrug thereof, and a pharmaceutical or food composition for the prevention or treatment of diseases by degrading the target protein including the same as an active ingredient. They can target specific proteins to adjust their concentrations, and can also deliver drugs and other small molecule compounds to lysosomes. The AUTOTAC chimeric compound according to the present invention can be usefully used as a pharmaceutical composition for the pre-
(Continued)

vention, amelioration or treatment of various diseases by selectively eliminating specific proteins.

12 Claims, 15 Drawing Sheets

(51) Int. Cl.

| | | |
|---|---|---|
| A61K 31/05 | (2006.01) | |
| A61K 31/12 | (2006.01) | |
| A61K 31/138 | (2006.01) | |
| A61K 31/166 | (2006.01) | |
| A61K 31/192 | (2006.01) | |
| A61K 31/277 | (2006.01) | |
| A61K 31/336 | (2006.01) | |
| A61K 31/355 | (2006.01) | |
| A61K 31/4015 | (2006.01) | |
| A61K 31/4155 | (2006.01) | |
| A61K 31/4184 | (2006.01) | |
| A61K 31/421 | (2006.01) | |
| A61K 31/428 | (2006.01) | |
| A61K 31/4535 | (2006.01) | |
| A61K 31/4709 | (2006.01) | |
| A61K 31/4745 | (2006.01) | |
| A61K 31/496 | (2006.01) | |
| A61K 31/50 | (2006.01) | |
| A61K 31/5025 | (2006.01) | |
| A61K 31/506 | (2006.01) | |
| A61K 31/517 | (2006.01) | |
| A61K 31/5377 | (2006.01) | |
| A61K 31/5415 | (2006.01) | |
| A61K 31/551 | (2006.01) | |
| A61K 31/565 | (2006.01) | |
| A61K 47/54 | (2017.01) | |
| A61K 47/55 | (2017.01) | |
| A61K 47/68 | (2017.01) | |
| A61P 25/28 | (2006.01) | |
| C07C 43/23 | (2006.01) | |
| C07C 47/575 | (2006.01) | |
| C07C 217/58 | (2006.01) | |
| C07C 235/06 | (2006.01) | |
| C07C 237/06 | (2006.01) | |
| C07C 275/24 | (2006.01) | |
| C07C 279/12 | (2006.01) | |
| C07D 303/18 | (2006.01) | |

(52) U.S. Cl.
CPC .......... *A61K 31/138* (2013.01); *A61K 31/166* (2013.01); *A61K 31/192* (2013.01); *A61K 31/277* (2013.01); *A61K 31/336* (2013.01); *A61K 31/355* (2013.01); *A61K 31/4015* (2013.01); *A61K 31/4155* (2013.01); *A61K 31/4184* (2013.01); *A61K 31/421* (2013.01); *A61K 31/428* (2013.01); *A61K 31/4535* (2013.01); *A61K 31/4709* (2013.01); *A61K 31/4745* (2013.01); *A61K 31/496* (2013.01); *A61K 31/50* (2013.01); *A61K 31/5025* (2013.01); *A61K 31/506* (2013.01); *A61K 31/517* (2013.01); *A61K 31/5377* (2013.01); *A61K 31/5415* (2013.01); *A61K 31/551* (2013.01); *A61K 31/565* (2013.01); *A61K 39/3955* (2013.01); *A61K 47/54* (2017.08); *A61K 47/55* (2017.08); *A61K 47/6803* (2017.08); *A61K 47/6849* (2017.08); *A61P 25/28* (2018.01); *C07C 43/23* (2013.01); *C07C 47/575* (2013.01); *C07C 235/06* (2013.01); *C07C 237/06* (2013.01); *C07C 275/24* (2013.01); *C07C 279/12* (2013.01); *C07D 303/18* (2013.01); *C07B 2200/07* (2013.01)

(56) References Cited

U.S. PATENT DOCUMENTS

| | | | |
|---|---|---|---|
| 4,857,522 A | 8/1989 | DiPietro et al. | |
| 2004/0009932 A1 | 1/2004 | Phelan et al. | |
| 2015/0175607 A1* | 6/2015 | Xie | C07D 475/08 |
| | | | 514/249 |
| 2016/0031799 A1 | 2/2016 | Xie et al. | |
| 2018/0243244 A1 | 8/2018 | Kwon et al. | |
| 2018/0265452 A1 | 9/2018 | Xie | |
| 2021/0024454 A1 | 1/2021 | Kwon et al. | |
| 2021/0163399 A1 | 6/2021 | Kwon et al. | |
| 2021/0347749 A1 | 11/2021 | Kwon et al. | |

FOREIGN PATENT DOCUMENTS

| | | | |
|---|---|---|---|
| CN | 112105598 A | | 12/2020 |
| EP | 3338787 A1 | | 6/2018 |
| KR | 10-2015-0039894 A | | 4/2015 |
| KR | 10-2017-0021525 | | 2/2017 |
| KR | 10-2017-0023045 A | | 3/2017 |
| KR | 10-2149539 B1 | | 8/2020 |
| KR | 10-2154294 B1 | | 9/2020 |
| WO | WO2013-022919 | | 2/2013 |
| WO | 2013106643 | * | 7/2013 |
| WO | 2015/031710 A1 | | 3/2015 |
| WO | WO2015-031710 | | 3/2015 |
| WO | WO2016-200827 | | 12/2016 |
| WO | WO2017-030292 | | 2/2017 |
| WO | WO2017-079267 | | 5/2017 |

OTHER PUBLICATIONS

Lu et al., Chemistry and Biology 2015, vol. 22, No. 6, pp. 755-763 (Year: 2015).*
Winter et al., Science 2015, vol. 348, No. 6241, pp. 1376-1381 (Year: 2015).*
Islam et al., Int. J. Mol. Sci. 2018, 19, 1405 (Year: 2018).*
Australian Office Action dated Aug. 29, 2022 in Australian (AU) Application No. 2019312065.
John W.A. Findlay et al., "Relationships between Immunogen Structure and Antisera Specificity in the Narcotic Alkaloid Series", Clinical Chemistry, 1981, vol. 27, No. 9, pp. 1524-1535 (12 p. total).
Maciej J. Stefanko et al., "Synthesis of functionalised polyethylene glycol derivatives of naproxen for biomedical applications", Tetrahedron, 2008, vol. 64, No. 44, pp. 10132-10139 (8 pages total).
Nicolai Stuhr-Hansen et al., "Synthesis of Symmetrical and Non-Symmetrical Bivalent Neurotransmitter Ligands", ChemistrySelect, 2016, vol. 1, No. 3, pp. 407-413 (7 pages total).
Office Action dated Oct. 19, 2023 in U.S. Appl. No. 17/262,129.
International Search Report and Written Opinion of the International Searching Authority issued Nov. 11, 2019 in International Application No. PCT/KR2019/009204.
Barlow et al., "β-Adrenoceptor Stimulant Properties of Amidoalkylamino-Substituted 1-Aryl-2-ethanols and 1-(Aryloxy)-2-propanols", J. Med. Chem., 1981, vol. 24, pp. 315-322.
International Search Report and Written Opinion of the International Searching Authority issued Nov. 11, 2019 in International Application No. PCT/KR2019/009203.
Puissant et al., "Resveratrol Promotes Autophagic Cell Death in Chronic Myelogenous Leukemia Cells via JNK-Mediated p62/SQSTM1 Expression and AMPK Activation", Cancer Research, 2010, vol. 70, No. 3, pp. 1042-1052.
Teramachi et al., "Blocking the ZZ domain of sequestosome1/p62 suppresses myeloma growth and osteoclast formation in vitro and induces dramatic bone formation in myeloma-bearing bones in vivo", Leukemia, 2016, vol. 30, pp. 390-398.
Office Action issued Feb. 1, 2022 in Japanese Application No. 2021-503886.

(56) References Cited

OTHER PUBLICATIONS

Lei et al., "Targeting oncoproteins for degradation by small molecules in myeloid leukemia", Leukemia & Lymphoma, 2017, pp. 1-8 (9 pages total).
Yongtae Kwon, AUTOTAC (Autophagy-targeting chimera) Technology, 2018, pp. 6-7 (7 pages total).
Office Action issued Feb. 2, 2023 in U.S. Appl. No. 17/262,129.
Office Action issued Jul. 21, 2023 in Chinese Application No. 201980047607.6.
Ji et al., "The AUTOTAC chemical biology platform for targeted protein degradation via the autophagy-lysosome system", Nature Communications, (2022) 13:904 | https://doi.org/10.1038/s41467-022-28520-4.
Communication dated Feb. 20, 2023, issued in Korean Application No. 10-2020-0092536.
Communication dated Feb. 20, 2023, issued in Korean Application No. 10-2020-0101379.
CAS Registry No. 1262521-61-8, 2011, 2 pages.
CAS Registry No. 562847-32-9, 2003, 1 page.
CAS Registry No. 99396-44-8, 1985, 2 pages.
CAS Registry No. 99342-74-2, 1985, 1 page.
CAS Registry No. 86955-68-2, 1984, 2 pages.
CAS Registry No. 77209-47-3, 1984, 1 page.
CAS Registry No. 76420-86-5, 1984, 2 pages.
CAS Registry No. 76420-85-4, 1984, 1 page.
CAS Registry No. 74867-70-2, 1984, 2 pages.
CAS Registry No. 58165-85-8, 1984, 1 page.
CAS Registry No. 2068956-48-7, 2017, 1 page.
CAS Registry No. 2000000-61-1, 2016, 1 page.
CAS Registry No. 1994480-74-8, 2016, 1 page.
CAS Registry No. 1881420-75-2, 2016, 1 page.
CAS Registry No. 1876857-32-7, 2016, 1 page.
CAS Registry No. 1874579-12-0, 2016, 2 pages.
CAS Registry No. 1869641-58-6, 2016, 1 page.
CAS Registry No. 1865340-43-7, 2016, 1 page.
CAS Registry No. 1859613-63-0, 2016, 1 page.
CAS Registry No. 1858409-61-6, 2016, 1 page.
CAS Registry No. 1827185-42-1, 2015, 1 page.
CAS Registry No. 1181454-24-9, 2009, 1 page.
CAS Registry No. 1181445-59-9, 2009, 1 page.
CAS Registry No. 940199-73-5, 2007, 1 page.
CAS Registry No. 892571-67-4, 2006, 1 page.
CAS Registry No. 861442-53-7, 2005, 1 page.
CAS Registry No. 861409-41-8, 2005, 1 page.
CAS Registry No. 774192-20-0, 2004, 1 page.
CAS Registry No. 190018-01-0, 1997, 1 page.
Registry(STN) [online], Nov. 16, 1984, CAS Registration No. 51169-99-4 (1 page total).
Registry(STN) [online], Nov. 16, 1984, CAS Registration No. 47689-63-4 (1 page total).
Registry(STN) [online], Jul. 27, 2004, CAS Registration No. 717091-45-7 (1 page total).
Kaiser, C. et al., "Adrenergic agents. 4. Substituted phenoxypropanolamine derivatives as potential β-adrenergic agonists," Journal of Medicinal Chemistry, 1977, vol. 20, No. 5, pp. 687-692 (6 pages total).
Yadav, J. S. et al., "An efficient protocol for regioselective ring opening of epoxides using samarium triflate: Synthesis of propranolol, atenolol and RO363," Journal of Molecular Catalysis A: Chemical, 2007, vol. 261, No. 2, pp. 207-212 (6 pages total).
Nelson, W. L. et al., "The 3, 4-Catechol derivative of propranolol, a minor dihydroxylated metabolite," Journal of Medicinal Chemistry, 1984, vol. 27, No. 7, pp. 857-861 (5 pages total).
Office Action issued Mar. 8, 2022 in Japanese Application No. 2021-503891.
"CAS RN1181561-56-7", STN Registry Database, 2009 (3 pages total).
"CAS RN1181561-57-8", STN Registry Database, 2009 (4 pages total).
"CAS RN1217054-95-9", STN Registry Database, 2010 (3 pages total).
"CAS RN1869641-58-6", STN Registry Database, 2016 (4 pages total).
"CAS RN1874579-12-0", STN Registry Database, 2016 (3 pages total).
"CAS RN774192-20-0", STN Registry Database, 2004, (14 pages total).
"CAS RN87265-43-8", STN Registry Database, 1984 (5 pages total).
"CAS RN892571-80-1", STN Registry Database, 2006 (3 pages total).
"CAS RN892573-08-9", STN Registry Database, 2006 (4 pages total).
Keith D. Green et al., "Identification and Characterization of Inhibitors of the Aminoglycoside Resistance Acetyltransferase Eis from Mycobacterium tuberculosis", ChemMedChem, 2012, vol. 7, pp. 73-77 (5 pages total).
PCT Search Report & Written Opinion for PCT/KR2019/009205, dated Nov. 8, 2019.
Ciechanover, A. & Kwon, Y.T., Exp Mol Med 47, e147 (2015).
Dikic, I. & Elazar, Z., Nat Rev Mol Cell Biol 19, 349-364 (2018).
Caccamo, A., Majumder, S., Richardson, A., Strong, R. & Oddo, S., J Biol Chem 285, 13107-20 (2010).
Ji, C.H. & Kwon, Y.T., Mol Cells 40, 441-449 (2017).
Jung, C. H., Ro, S. H., Cao, J., Otto, N. M. & Kim, D. H., FEBS Lett 584, 1287-95 (2010).
Ravikumar, B., Duden, R. & Rubinsztein, D.C., Hum Mol Genet 11, 1107-17 (2002).
Rodriguez-Navarro, J.A. et al., Neurobiol Dis 39, 423-38 (2010).
Sriram, S.M. & Kwon, Y.T., Nat Struct Mol Biol 17, 1164-5 (2010).
Sriram, S.M., Kim, B.Y. & Kwon, Y.T., Nat Rev Mol Cell Biol 12, 735-47 (2011).
Tasaki, T. et al., Mol Cell Biol 25, 7120-36 (2005).
Webb, J.L., Ravikumar, B., Atkins, J., Skepper, J.N. & Rubinsztein, D.C., J Biol Chem 278, 25009-13 (2003).
Puissant et al., Cancer Res., Feb. 1, 2010, vol. 70, No. 3, pp. 1042-1052.
AUTOTAC (Autophagy-targeting chimera) Technology, Nov. 29, 2018, pp. 6-7.
Bondeson et al., Cell Chem Biol 25, 78-87.e5 (2019).
Xiong J Cell Physiol. 2019;1-9.
Lei et al., Leukemia & Lymphoma, Dec. 4, 2017, pp. 1-8.
An and Fu, EBioMedicine 36, 553-562 (2018).

* cited by examiner

[Fig. 1]
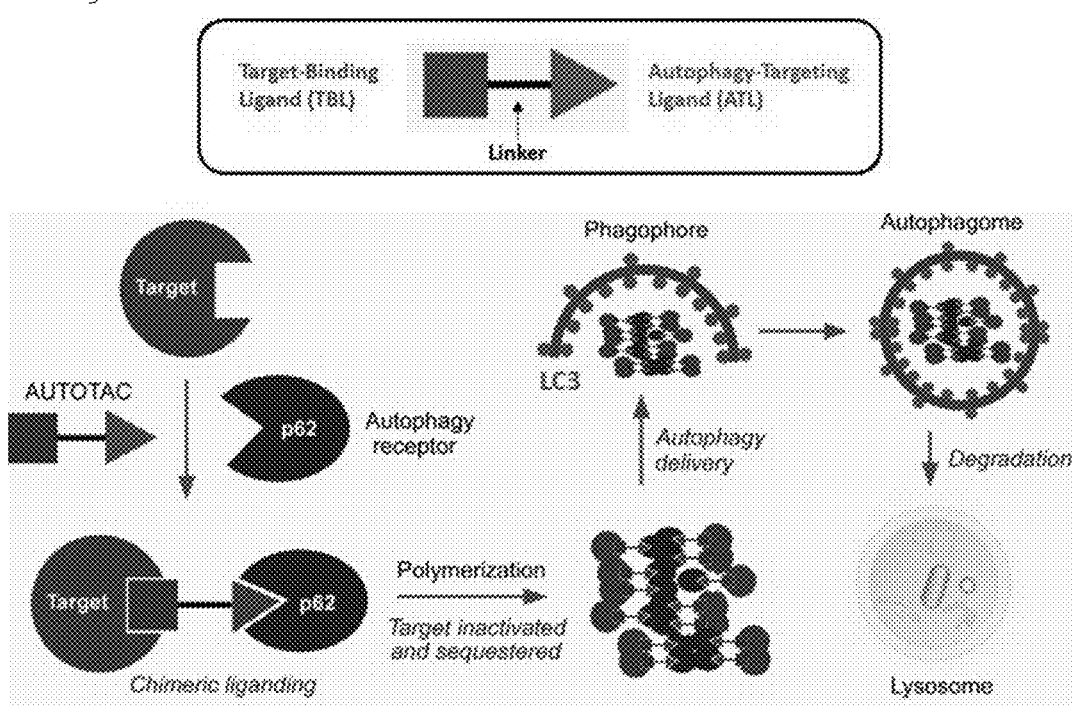

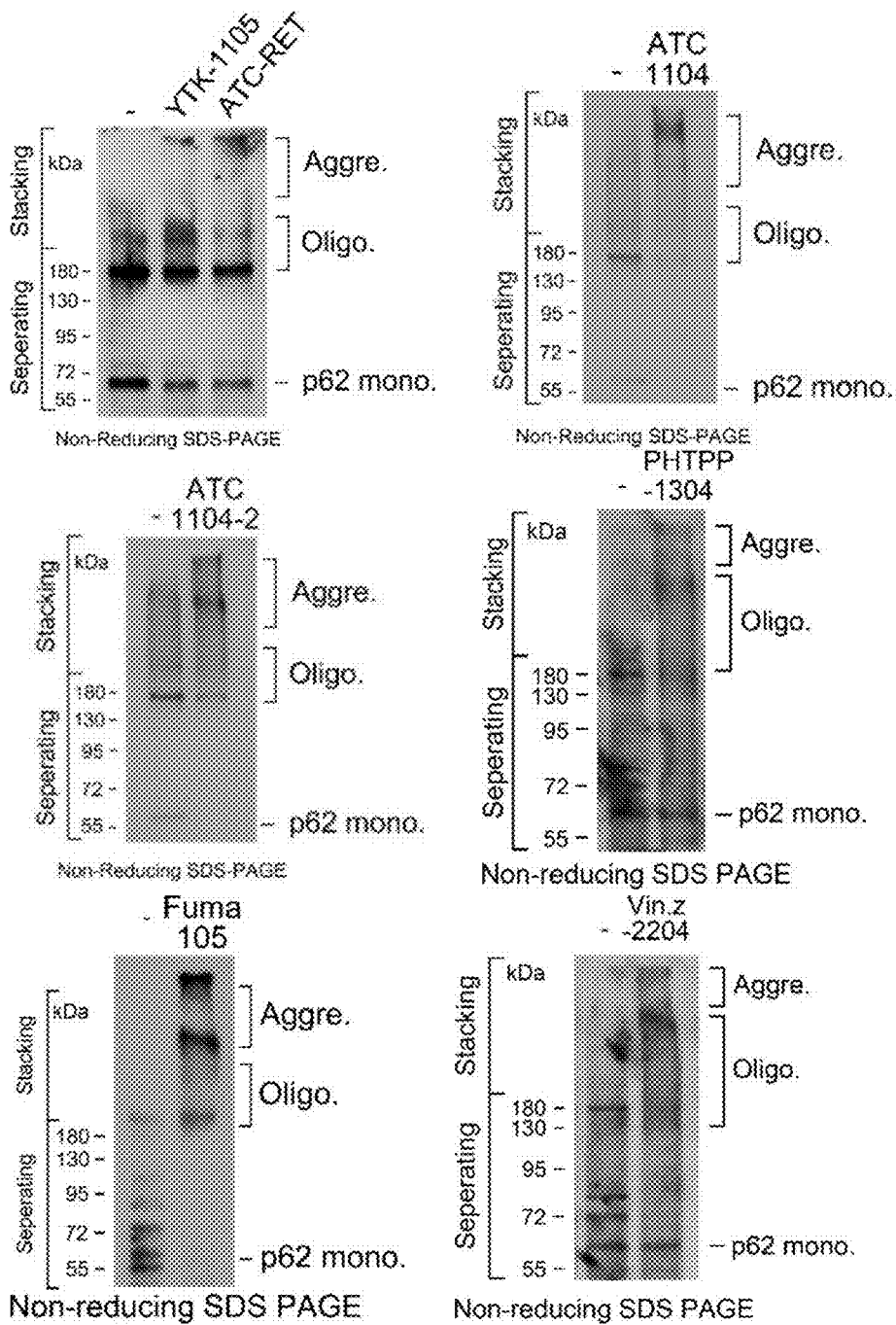
[Fig. 2a]

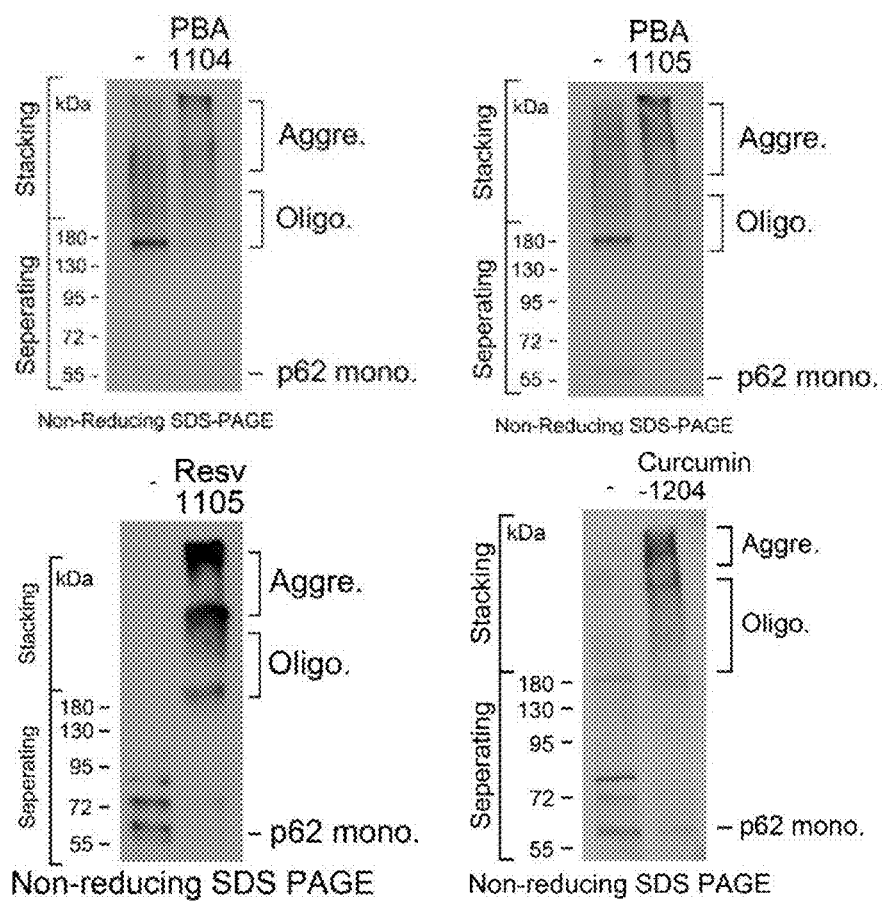

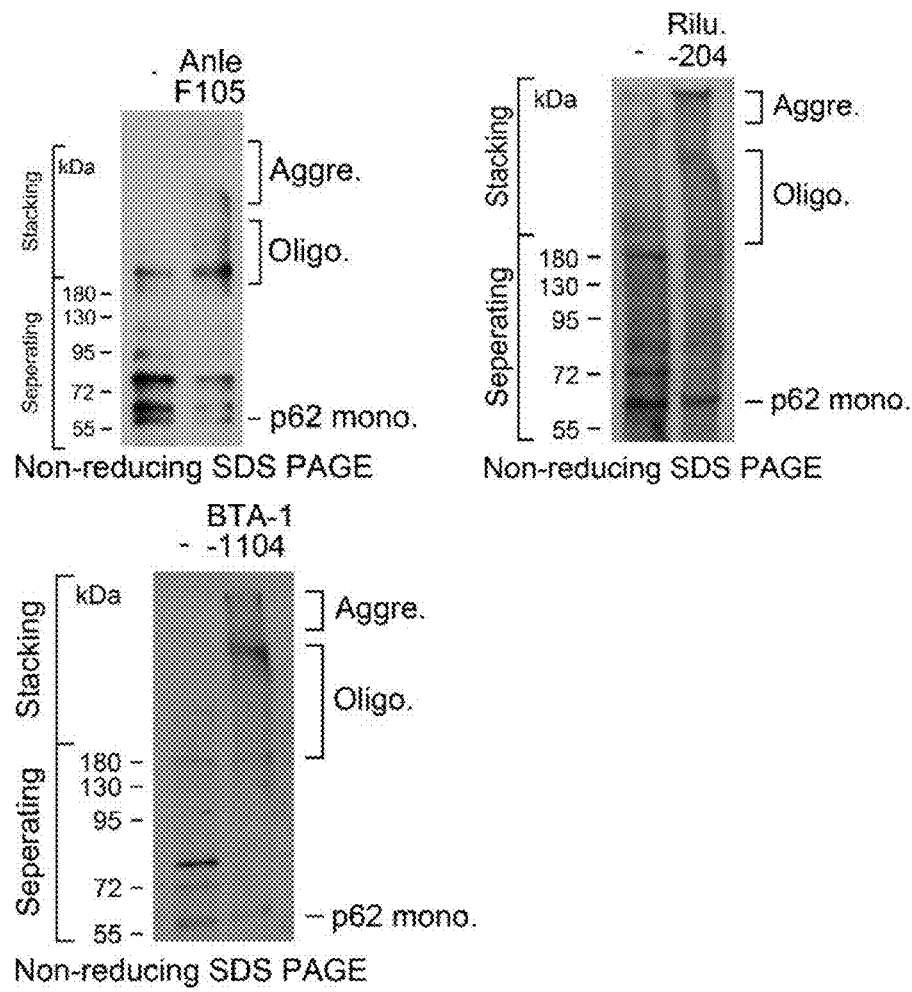
[Fig. 2c]

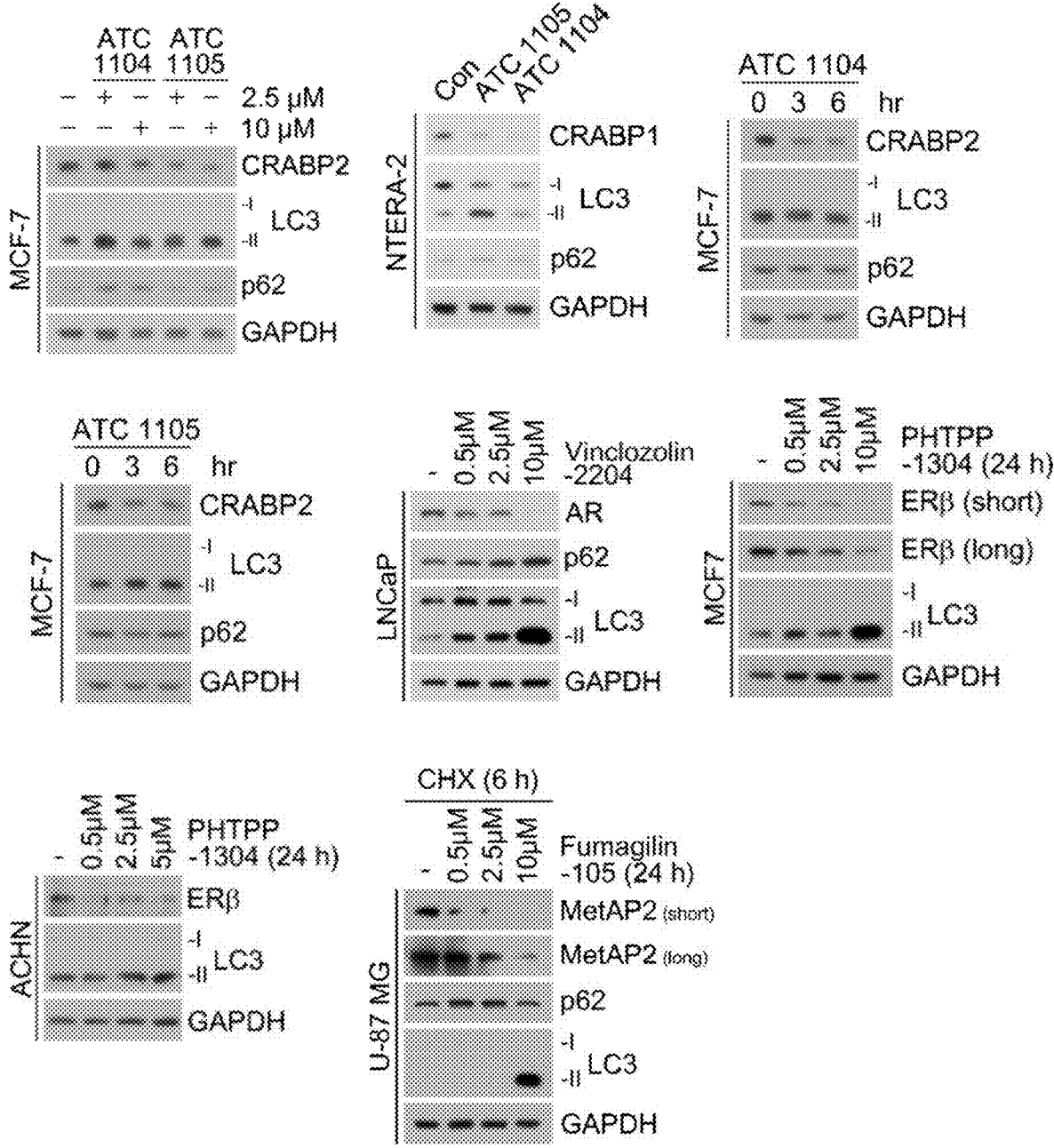
[Fig. 3a]

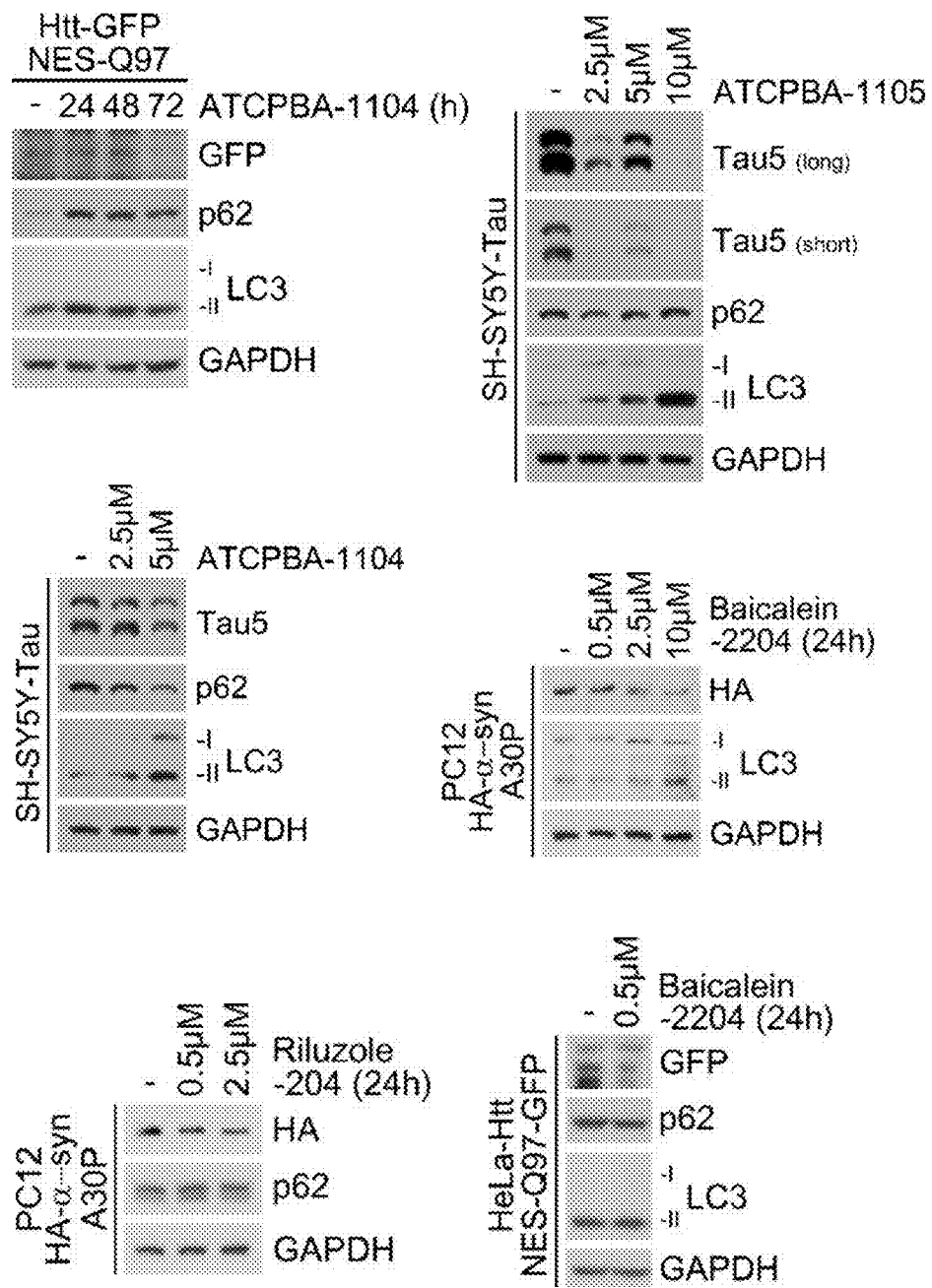
[Fig. 3b]

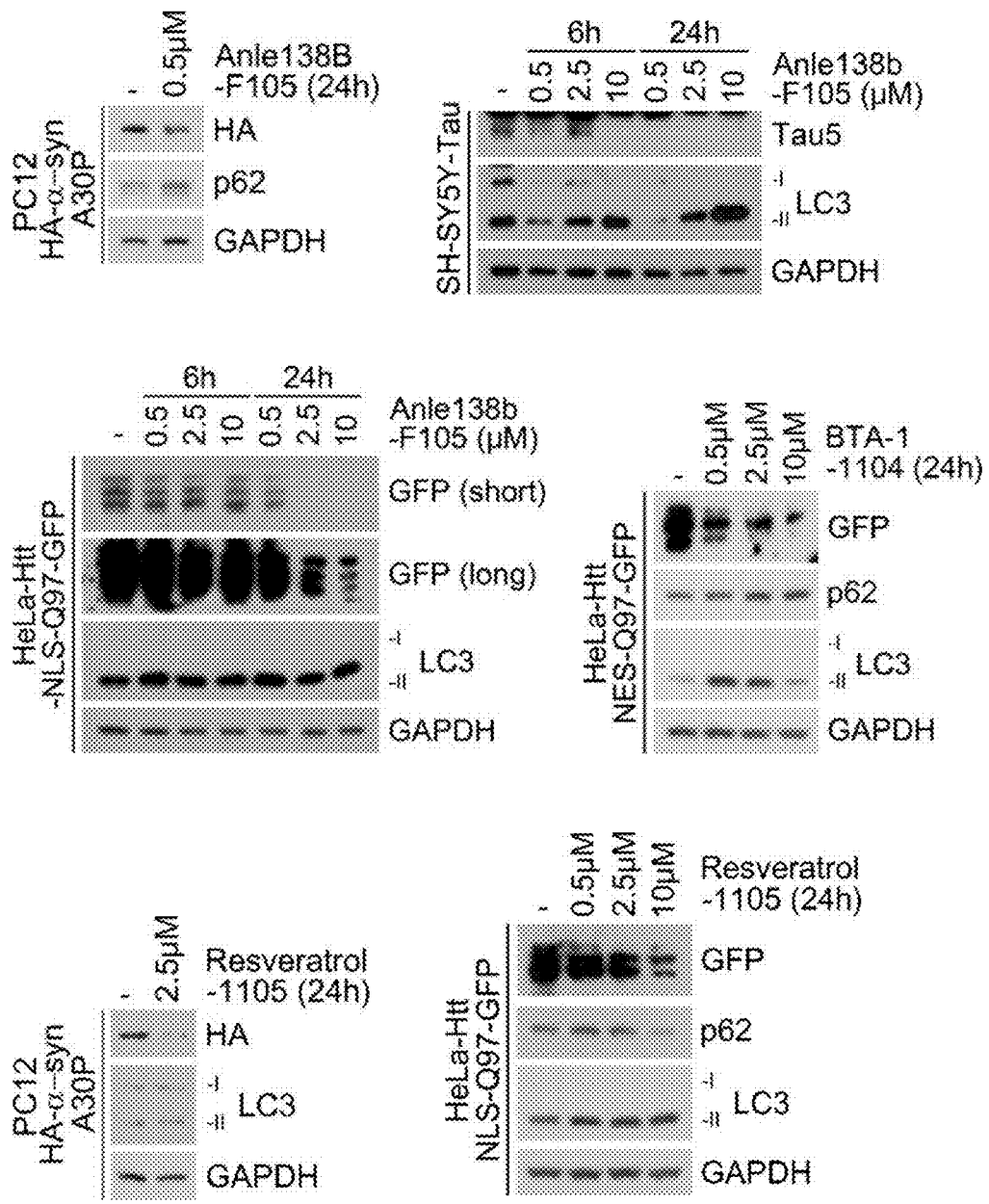
[Fig. 3c]

[Fig. 4a]
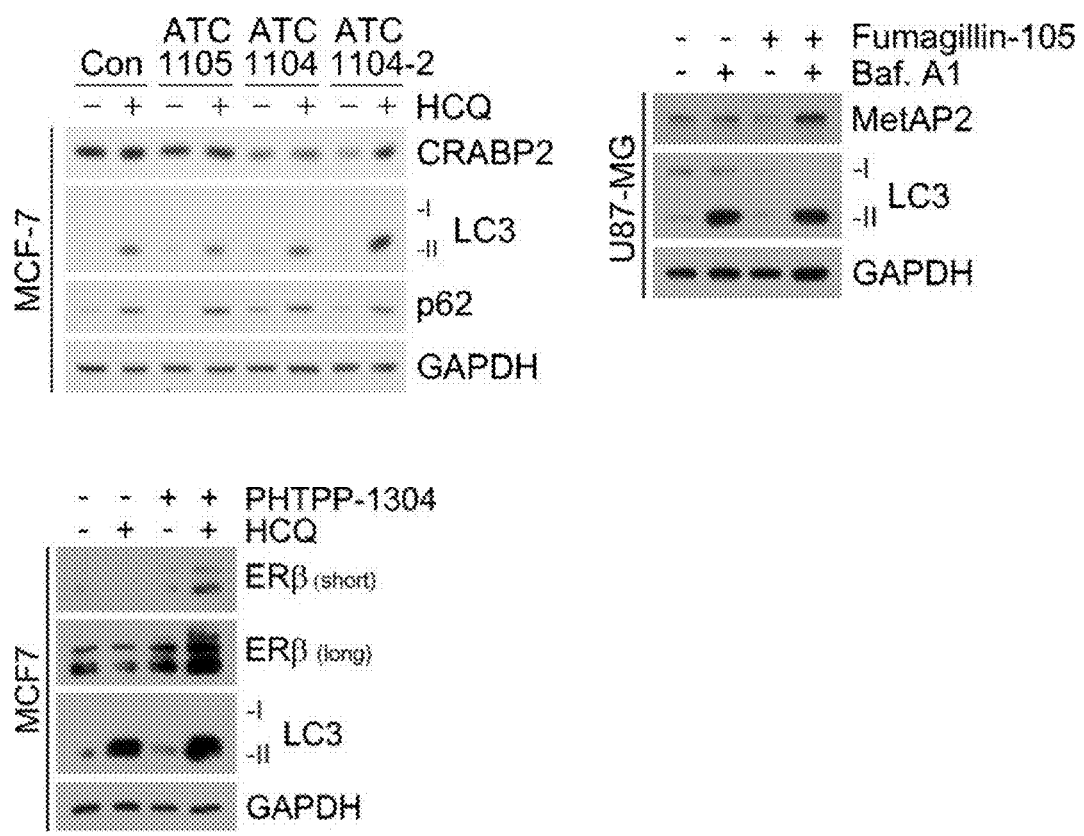

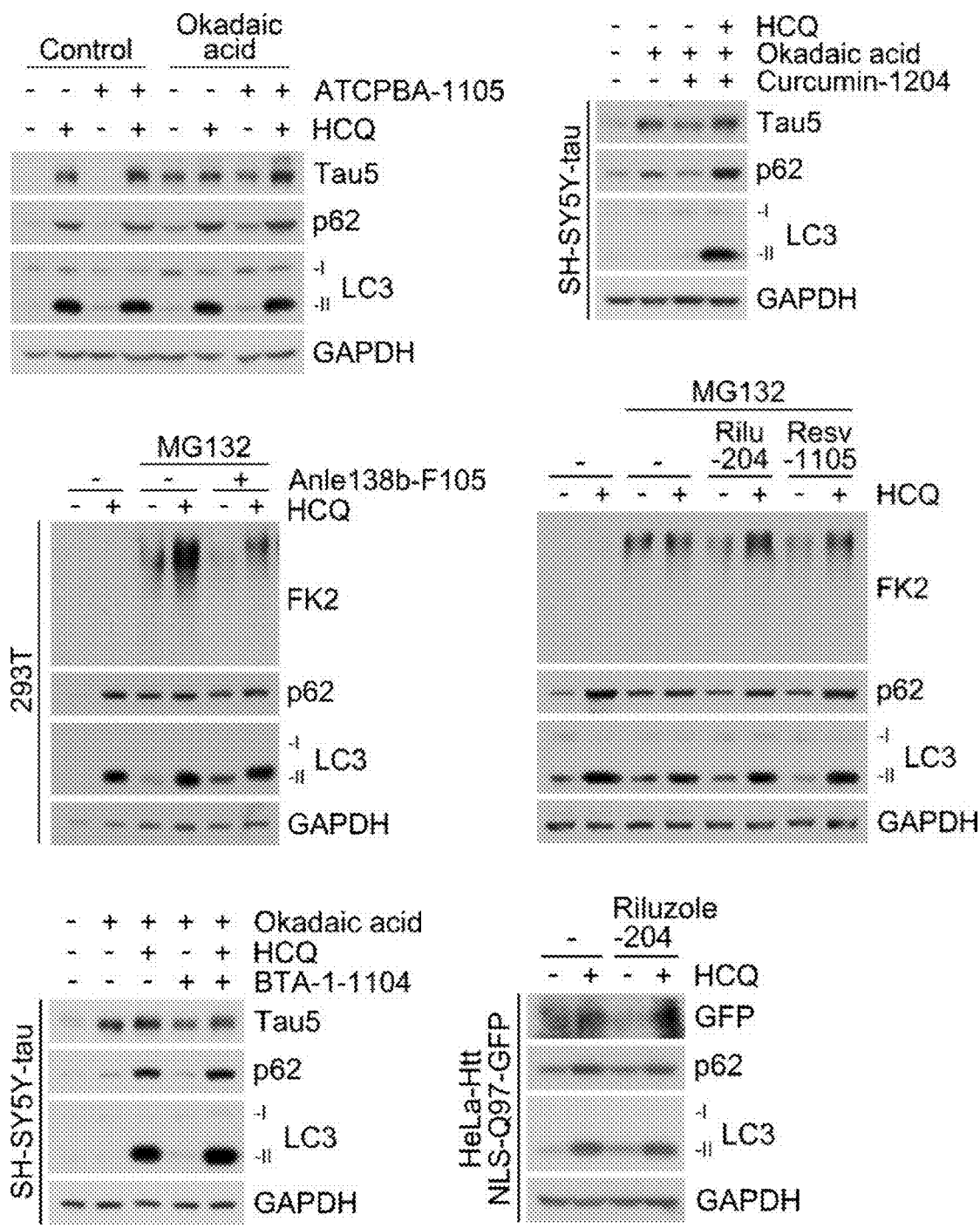
[Fig. 4b]

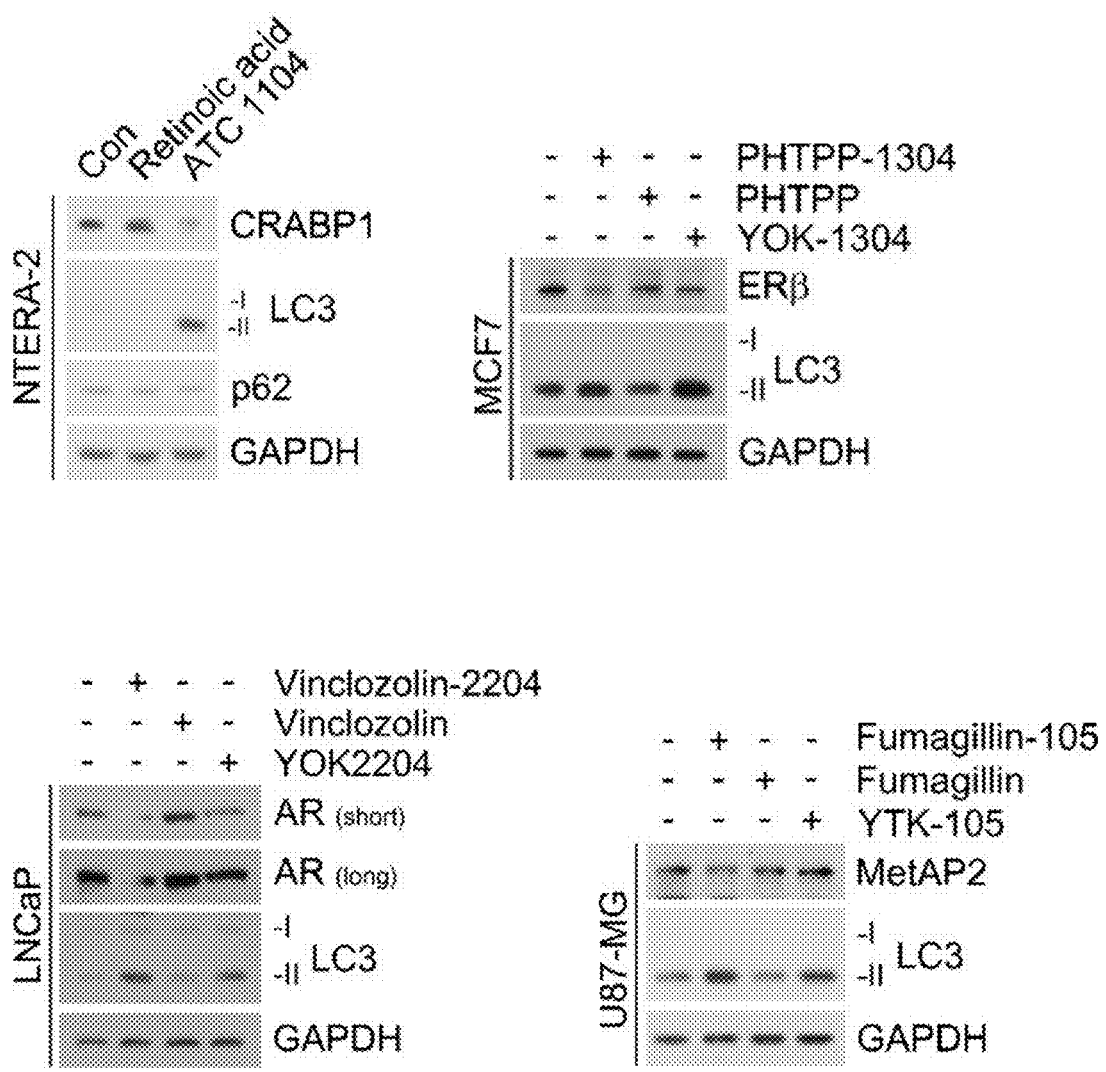
[Fig. 5a]

【Fig. 5b】
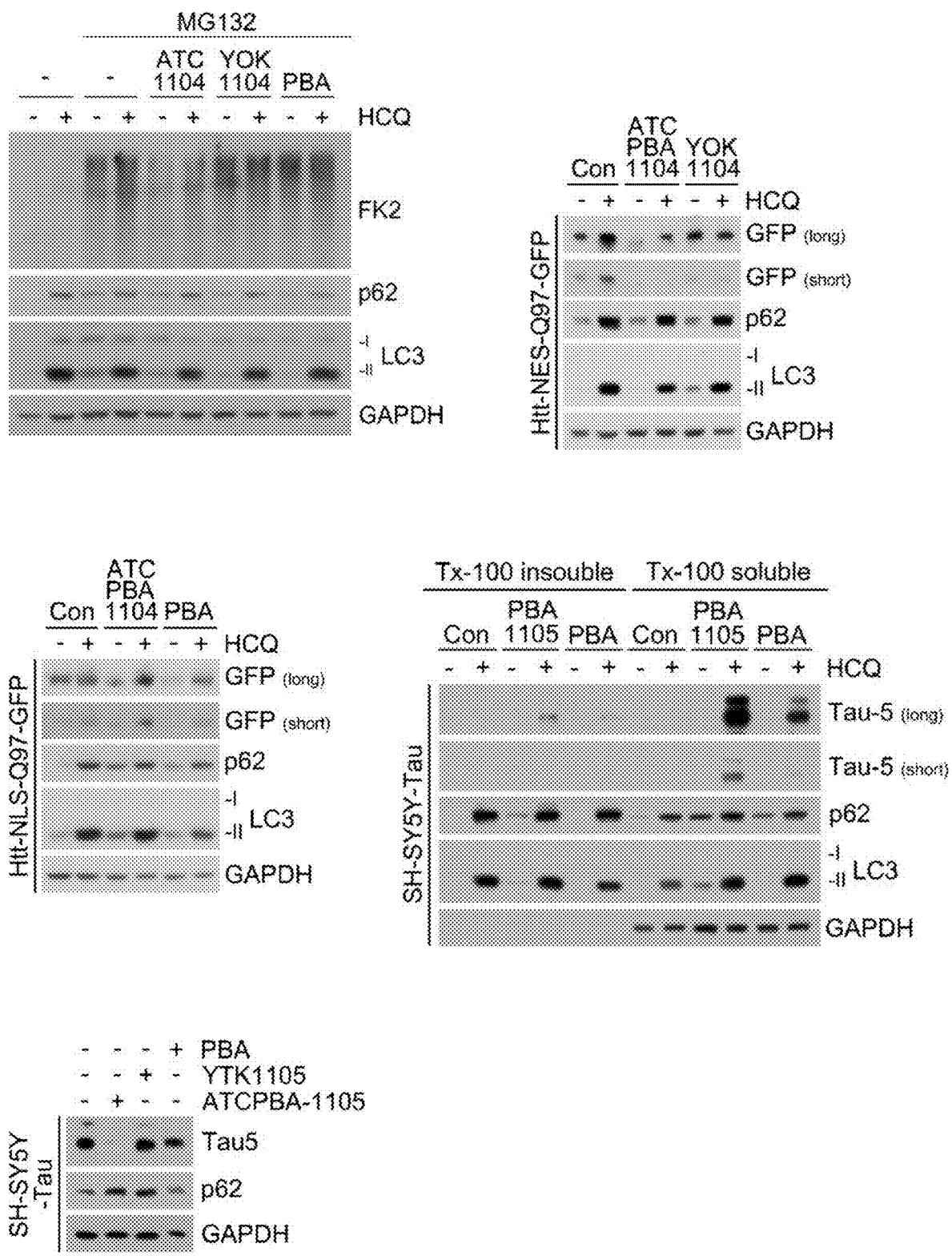

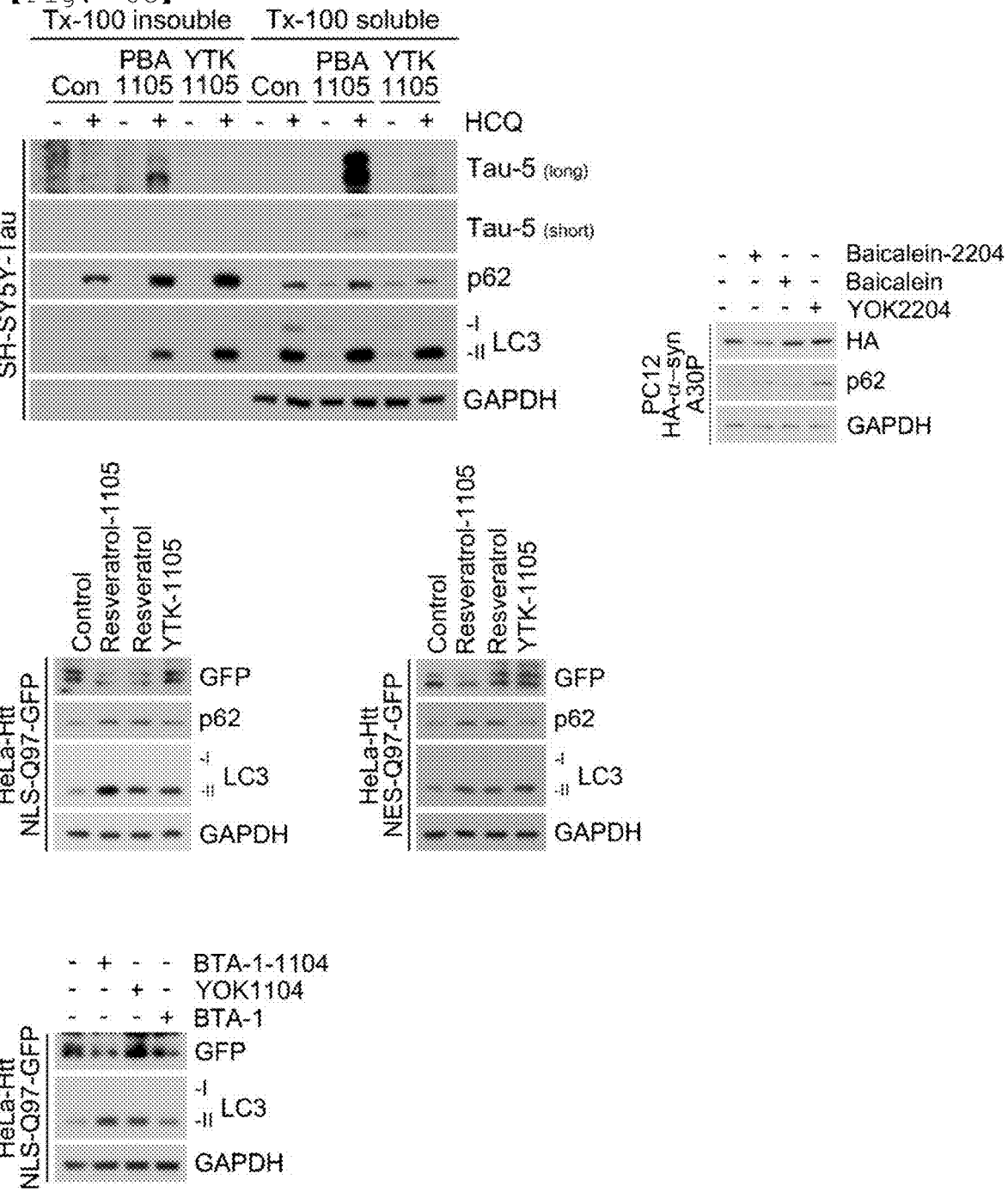

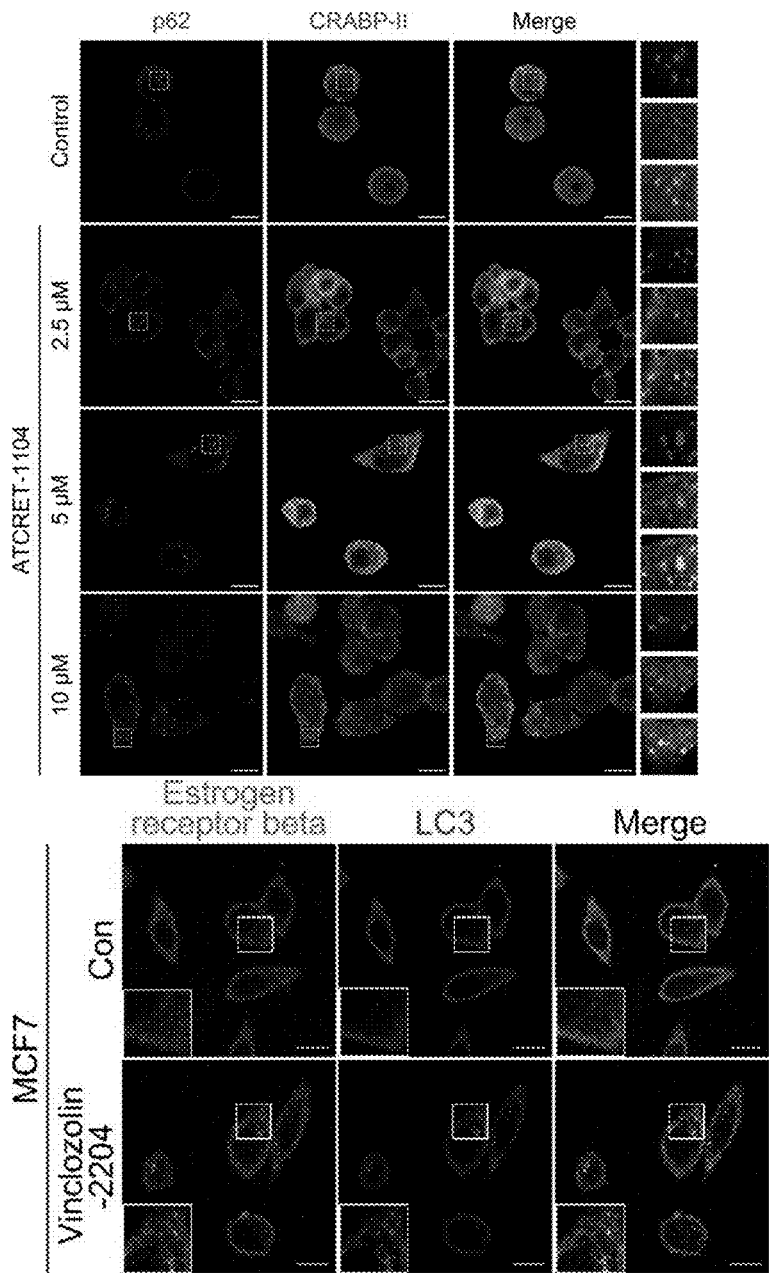
[Fig. 6a]

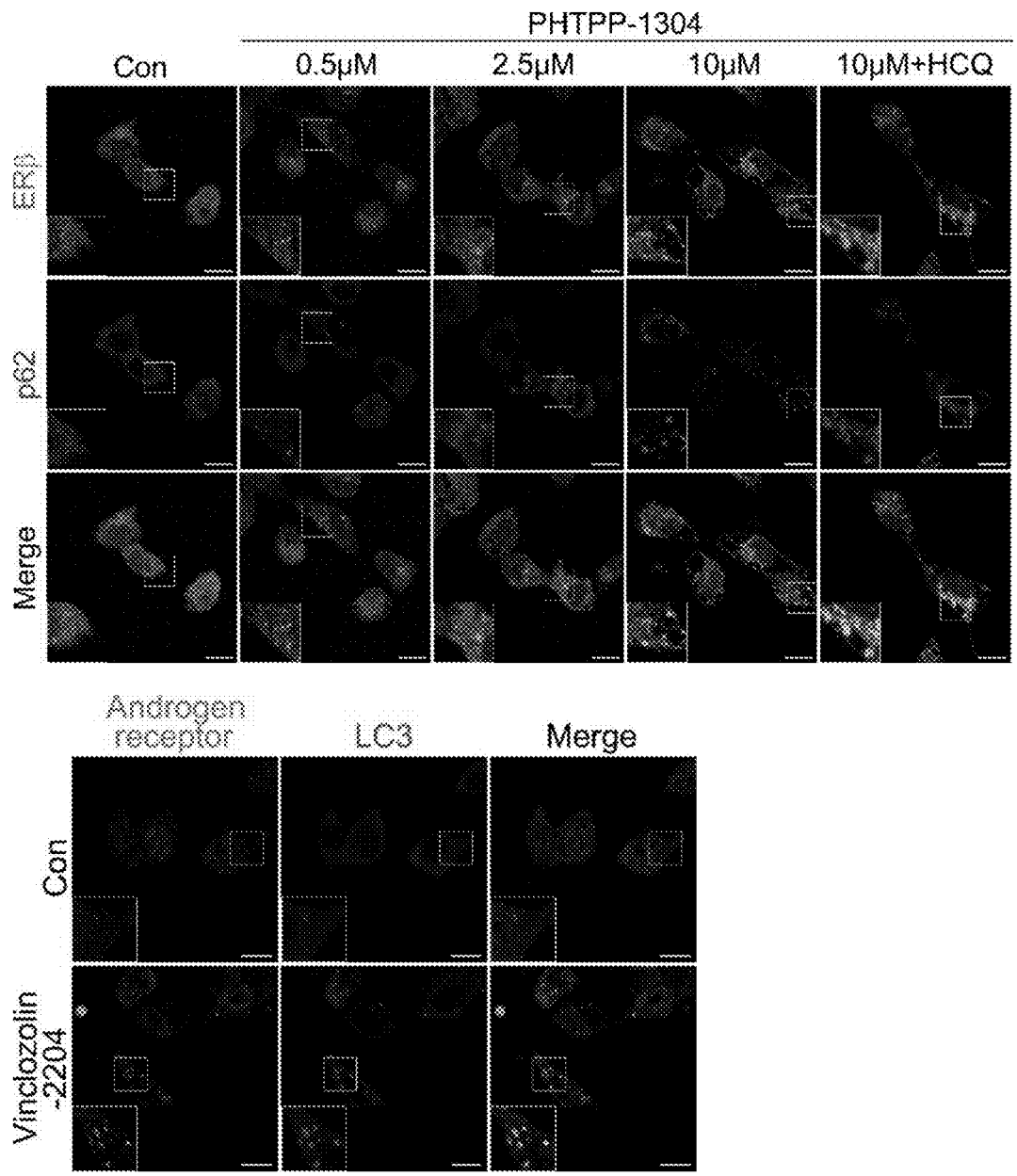
[Fig. 6b]

[Fig. 6c]
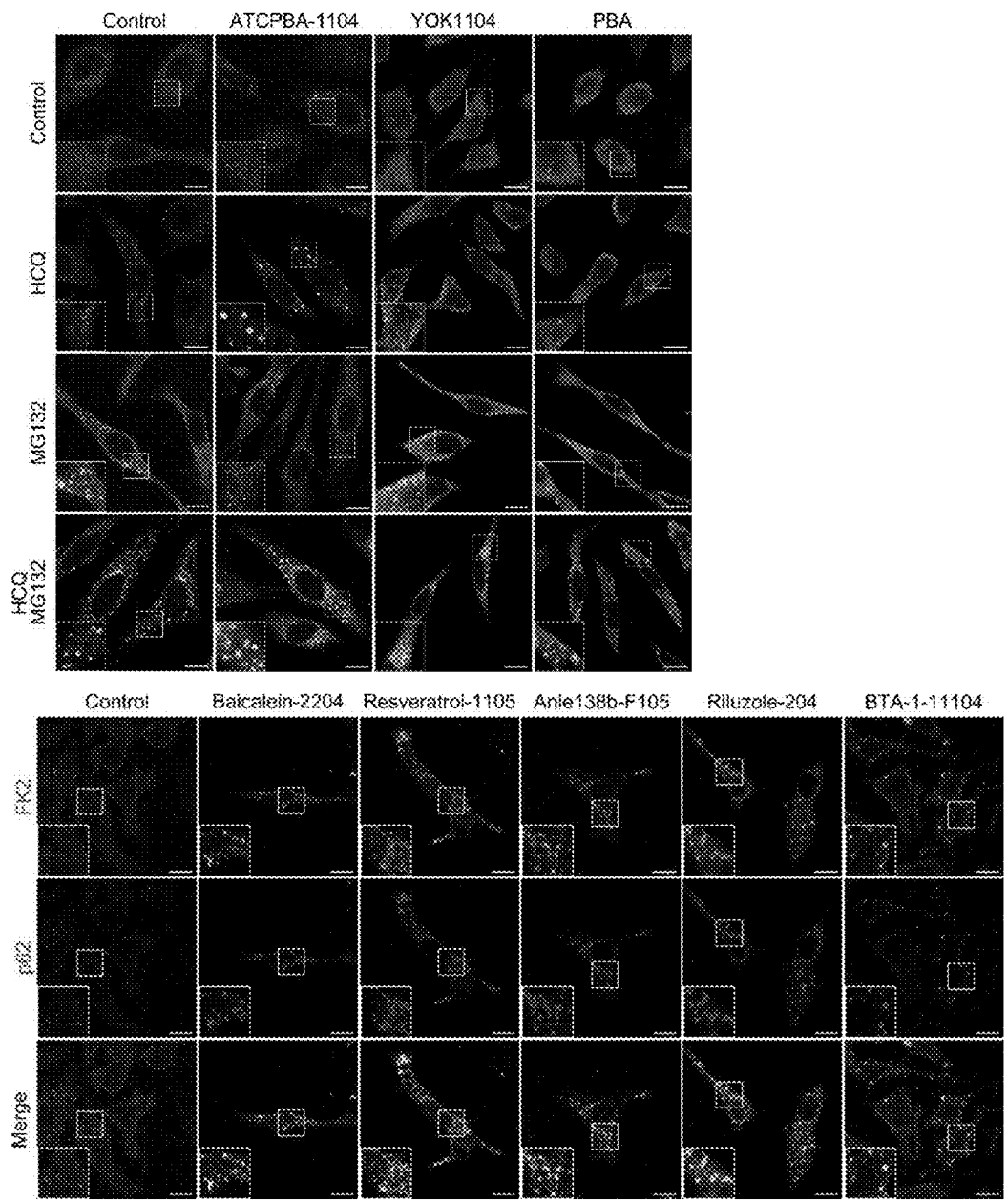

AUTOTAC CHIMERIC COMPOUND, AND COMPOSITION FOR PREVENTING, AMELIORATING OR TREATING DISEASES THROUGH TARGETED PROTEIN DEGRADATION COMPRISING THE SAME

REFERENCE TO RELATED APPLICATIONS

The present application is a National Stage Application of PCT Application No. PCT/KR2019/009205 filed on Jul. 24, 2019, which claims priority to Provisional U.S. Application No. 62/702,473, filed Jul. 24, 2018, which are incorporated herein in their entirety.

FIELD OF THE INVENTION

The present invention relates to a novel chimeric compound, and more particularly to a chimeric compound in which a p62 ligand and a target-binding ligand are connected by a linker, and a pharmaceutical or food composition for preventing or treating diseases through targeted protein degradation comprising the same.

DESCRIPTION OF THE RELATED ART

The N-end rule pathway is a proteolytic system where a specific N-terminal residue of a protein acts as a degradation signal. The N-end rule degradation signal is exemplified by type I basic residues including N-terminal arginine (Nt-Arg), lysine (Nt-Lys) and histidine (Nt-His); and type II hydrophobic residues including phenylalanine (Nt-Phe), leucine (Nt-Leu), tryptophan (Nt-Trp), tyrosine (Nt-Tyr) and isoleucine (Nt-Ile). These N-terminal residues bind to specific N-recognins (hereinafter referred to as N-ligands). The present inventors have first discovered or cloned previously known N-recognins, namely UBR1, UBR2, UBR4, and UBR5, and found that they utilize the UBR box as a substrate recognition domain (Tasaki, T. et al., Mol Cell Biol 25, 7120-36 (2005)). The present inventors have also found that the UBR box binds to type-I N-end rule ligands (Nt-Arg, Nt-Lys, Nt-His) such as N-terminal arginine residue to recognize a substrate and to link a ubiquitin chain to the substrate. It has further been found that UBR1 and UBR2 have an N-domain which plays an important role in the binding of type-2 N-end rule ligands (Nt-Trp, Nt-Phe, Nt-Tyr, Nt-Leu, and Nt-Ile) (Sriram, S. M., Kim, B. Y. & Kwon, Y. T., Nat Rev Mol Cell Biol 12, 735-47 (2011)). The ubiquitinized substrate produced from the binding between N-recognins and N-end rule ligands is delivered to proteasome where it is degraded into a short peptide. In this process, specific N-terminal residues (Nt-Arg, Nt-His, Nt-Lys, Nt-Trp, Nt-Phe, Nt-Tyr, Nt-Leu, Nt-Leu) are the essential determinants of binding since N-recognins provide most of the hydrogen bonds needed to target the N-end rule substrate (Sriram, S. M. & Kwon, Y. T., Nat Struct Mol Biol 17, 1164-5 (2010)).

Intracellular protein degradation is mainly performed by the ubiquitin-proteasome system (UPS) and the autophagy-lysosome system. In general, UPS regulates the intracellular concentrations of regulators with normal folding, or degrades proteins that have been misfolded and have lost their functions. At this time, the substrate is directly or indirectly recognized and ubiquitinated by estimated about 500-1,000 E3 ligases, and then unfolded into polypeptide helices and degraded by proteasomes (Ji and Kwon, Mol Cells 40, 441-449 (2017)). In normal cells, the process of the ubiquitin-proteasome system is smooth, but disease-related proteins become misfolded proteins that are incorrectly folded, or aggregates resulting from the accumulation of misfolded proteins block proteasome functions, or proteasome function declines during aging, or the degradation of proteins associated with diseases are not smoothly performed due to the reprogramming of protein transcription and translation (Ciechanover, A. & Kwon, Y. T., Exp Mol Med 47, e147 (2015)). In a representative example, the respective major pathological proteins of proteinopathies (Alzheimer's disease, Huntington's disease, Parkinson's disease, human mad cow disease, Lou Gehrig's disease/amyotrophic lateral sclerosis, alpha-1 antitrypsin deficiency, keratopathy, type 2 diabetes, etc.) are misfolded, ubiquitinated and accumulated, and these surplus protein wastes are converted back into aggregates (Aguzzi and O'Connor, Nat Rev Drug Discov 9, 237-48 (2010)). Such specific mutant proteins have a strong property of being transformed into aggregates, and thus are not degraded into the proteasome described above. The reason is that since proteasome has a narrow inner diameter of about 13 Angstroms, the misfolded protein must be unfolded, and when the proteins are aggregated, they will not be unfolded. In another representative example, cancer cells are known to increase transcription and translation of oncoproteins and simultaneously inhibit the degradation by reprogramming intracellular transcription and translation (Xiong et al., J Cell Physiol 234, 14031-14039 (2019)). In addition, subunit proteins and transmembrane proteins that form a complex also have limited degradation due to the ubiquitin-proteasome system.

Autophagy is a major intracellular protein degradation system along with UPS (ubiquitin-proteasome system). Autophagy is a protein degradation process essential to maintain cell homeostasis and genetic stability by degrading aged or impaired cellular organelles or damaged or abnormally folded proteins and their aggregates (Ji and Kwon, Mol Cells 40, 441-449 (2017)). In particular, when pathological proteins and their aggregates are accumulated in a cytoplasm, they can become cytotoxic substances, and thus, should be received and degraded by autophagy. The mechanism for autophagy is largely divided into macroautophagy, microautophagy and chaperone-mediated autophagy, and it is divided into bulk autophagy and selective autophagy, depending on the purpose of degrading the intracellular substrate (Dikic, I. & Elazar, Z., Nat Rev Mol Cell Biol 19, 349-364 (2018)). Of these, selective autophagy and chaperone-mediated autophagy cause selective degradation of unwanted intracellular proteins and dysfunctional organelles. By inducing selective autophagy, the development of new therapies for diseases based on the accumulation of pathologically misfolded proteins and dysfunctional organelles is currently building a new paradigm. p62/SQSTM1/Sequestosome-1 protein is important for initiating the formation of autophagosome which is a mediator in the mechanism for selective autophagy, and delivering the contents. At this time, p62 proteins bind to pathological proteins and their aggregates, which are then delivered to autophagosome. P62 undergoes self-oligomerization as a key process when delivering pathological proteins to autophagosomes (Dikic, I. & Elazar, Z., Nat Rev Mol Cell Biol 19, 349-364 (2018)). At this time, the pathological proteins are concentrated together to reduce the volume, thus facilitating degradation by autophagy. PB1 domain mediates the self-oligomerization of p62, but the regulatory mechanism thereof is not well known. The misfolded protein-p62 conjugate delivered to autophagosome can be degraded by lysosomal enzymes as the autophagosome binds to a lysosome.

Through the mechanisms described above, autophagy is important for maintaining cell homeostasis by regulating intracellular changes in damaged proteins and cellular organelles. When autophagic function is weakened, it leads to the accumulation and aggregation of the misfolded proteins, which results in proteinopathies or cancer. Studies on the activation of bulk autophagy to treat these diseases have been actively conducted (Ciechanover, A. & Kwon, Y. T., Exp Mol Med 47, e147 (2015)). A regulator that normally inhibits bulk autophagy is mTOR. A method of activating autophagy using mTOR inhibitors is most widely used (Jung, C. H., Ro, S. H., Cao, J., Otto, N. M. & Kim, D. H., FEBS Lett 584, 1287-95 (2010)). Specifically, by using rapamycin treatment, amyloid beta (Ab) and tau were eliminated and simultaneously cognitive ability was improved in an AD animal model over-expressing APP (Caccamo, A., Majumder, S., Richardson, A., Strong, R. & Oddo, S., J Biol Chem 285, 13107-20 (2010)); tau was eliminated in an AD animal model over-expressing tau (Rodriguez-Navarro, J. A. et al., Neurobiol Dis 39, 423-38 (2010)); and the overexpressed mutant alpha-synuclein protein aggregate was eliminated in a PD mouse model (Webb, J. L., Ravikumar, B., Atkins, J., Skepper, J. N. & Rubinsztein, D. C., J Biol Chem 278, 25009-13 (2003)). It was confirmed that in a HD mouse, CCI-779, a rapamycin-like substance, is used to efficiently eliminate huntingtin aggregates and also to improve animal behavior and cognitive ability (Ravikumar, B., Duden, R. & Rubinsztein, D. C., Hum Mol Genet 11, 1107-17 (2002)). However, mTOR plays a very important role in various intracellular pathways including NF-kB. Therefore, although it exhibits excellent activity to eliminate misfolded protein aggregates of proteinopathies, there is a limitation in that these bulk autophagy activators, which are known that mTOR is a drug target, are used as therapeutic agents. In addition, there are no effective autophagosome-targeted therapies and therapeutic agents to target disease-inducing proteins.

In central dogma, genetic information stored in DNA is transcribed into RNA and translated into proteins to regulate cell functions. In the case of DNA, target cleavage can occur using DNA editing technology such as CRISPR; and in the case of RNA, target degradation can occur using siRNA. However, in the case of proteins, targeted degradation techniques are relatively limited. If it can be degraded by targeting disease-inducing proteins, it may be used as a platform technology for drug development in the pharmaceutical industry. PROTAC (PROteolysis Targeting Chimera) is a technology developed to effect intracellular degradation of target proteins. PROTAC uses a chimeric compound of a ligand that recognizes a target protein and a ligand that recognizes an E3 ubiquitin enzyme (An and Fu, EBioMedicine 36, 553-562 (2018)). When the target binder binds to disease-inducing protein and brings it closer to E3, E3 recognizes as a substrate and performs ubiquitination to induce proteasomal degradation. Since the existing disease treatment paradigm is protein enzyme inhibition, the development of new therapies for proteins that cannot be targeted with the existing therapeutic agent is of a great importance. From these viewpoints, PROTAC is an attractive new therapeutic development method by enabling selective degradation under ubiquitin-proteasome system with respect to proteins that cannot be targeted by a conventional enzyme inhibition method. However, PROTAC induces proteasomal degradation by utilizing only ligands that recognize the E3 ubiquitin enzyme, and therefore, when the target protein is misfolded to form an aggregate, or to form a complex, or to bind to a membrane structure, it is difficult to degrade (Bondeson et al., Cell Chem Biol 25, 78-87.e5 (2019)). In addition, PROTAC is unable to degrade intracellular organelles such as endoplasmic reticulum and mitochondria, and pathogens such as viruses and bacteria. Therefore, there is a need for the development of a method to target pathological proteins, organelles and aggregates and deliver them to selective autophagy.

In order to regulate cell functions, a method of indirectly regulating protein activity and concentration by editing DNA or by degrading RNA is widely used. In particular, RNA enables target degradation using siRNA, but has low cell permeability of siRNA, and is delivered into cells using transfection reagents, etc. Therefore, the process is complicated and expensive. Moreover, if the target protein is stable, it is difficult to lower the protein concentration even if RNA is degraded. Therefore, it is necessary to develop a method or a substance, i.e., a protein degrader, that directly degrades by targeting specific proteins.

DISCLOSURE

Technical Problem

Traditional drugs vary such as small molecule synthetic compounds, antibodies, proteins, peptides, etc., but the basic principle is to bind to an active site of a particular protein to inhibit the activity of disease-causing proteins, thereby exhibiting drug efficacies. These traditional drug development methods have some limitations. First, high concentrations of drugs are required, which can cause side effects of the drugs. Since drug-protein binding is not a stable covalent bond, it can be separated. That is, when the drug binds to the target protein, it exhibits drug efficacy, but when the drug is separated from the target protein, it does not exhibit drug efficacy. Therefore, in order to maintain the drug efficacy, a high drug concentration must be maintained throughout the body. However, increasing the drug concentration for drug efficacy allows the drug to bind to other unexpected proteins, and this situation can lead to drug side effects. Second, drug target proteins are limited. Until now, approximately 400 types of drug target proteins have been approved by the US Food and Drug Administration (FDA). Over 90% of these are enzymes, transmitter proteins, channel/membrane proteins, etc. Because these drug target proteins have an active site and a binding site, it can be relatively easily found with relatively traditional drug development process. However, there are an estimated 3,000 proteins associated with disease, and currently, only about 13% of approved drugs are used for the target. Therefore, a paradigm shift in development of new drugs is necessary, and when using target protein degradation technology, it has the following advantages over existing therapeutic agents. Firstly, because it can degrade transcription factors, proteins involved in signal transduction through protein binding, and aggregated and accumulated proteins such as tau, it is possible to regulate undruggable proteins that are difficult to target with conventional drugs. Secondly, it is possible to overcome the phenomenon in which the target protein is overexpressed and overactivated or tolerated by drugs, or the drug efficacy may be reduced by activation of other signal transduction systems. Thirdly, since the target protein degradation material is reused after degrading the target protein, it can be administered at a low dose, and the side effects associated therewith are also reduced. Fourthly, since a specified time is required to degrade and reproduce the target protein, the administration cycle is increased and the economy is high.

In order to solve the problems of the existing therapeutic agent as described above, it is an object of the present invention to provide a novel AUTOTAC (Autophagy-targeting chimera) compound in which a novel p62 ligand compound inducing activation and oligomerization of p62 proteins, and a target-binding ligand are connected by a linker (FIG. 1).

It is another object of the present invention to provide a pharmaceutical or food composition for eliminating disease-inducing proteins comprising the aforementioned AUTOTAC compound as an active ingredient.

It is yet another object of the present invention to provide a biochemical screening method and technology for effecting intracellular degradation of target proteins.

Technical Solution

In order to achieve the above objects, one embodiment of the present invention provides novel AUTOTAC chimeric compounds in which a ligand binding to the ZZ domain of p62 and a target-binding ligand are connected by a linker.

Another embodiment of the present invention provides (1) a method of inducing p62 oligomerization and structural activation; (2) a method of increasing p62-LC3 binding; (3) a method of delivering p62 and a target protein to autophagosome; (4) a method of activating autophagosome biogenesis; (5) targeting and delivering a target protein to autophagy; (6) a method of targeting and inactivating a target protein; and (7) a method of degrading a target protein by lysosome.

In another embodiment, the present invention provides a pharmaceutical composition or a health functional food for the prevention or treatment of diseases, containing the aforementioned AUTOTAC chimeric compound as an active ingredient. Preferably, the diseases include not only cancer or degenerative brain diseases, but also other diseases that can be expected to have a therapeutic effect upon target degradation of certain proteins such as rare intractable diseases.

The core technology of the present invention is to (1) connect a target protein with p62 using an AUTOTAC material, (2) induce self-oligomerization of p62, (3) allow a target protein to form a complex with p62, thereby biologically inactivating the target protein, (4) then deliver the target protein-p62 complex to an autophagy membrane such as a phagophore, and (5) degrade the target protein-p62 complex in lysosomes.

The pharmacokinetics and core technologies of the present invention are summarized in FIG. 1.

Specifically, as shown in FIG. 1, the AUTOTAC chimeric compound has a structure in which a target-binding ligand (TBL) and a p62 ZZ domain ligand, i.e., an autophagy-targeting ligand (ATL), are connected via a linker. It binds to the target protein via the target ligand, and the autophagy-targeting ligand is oligomerized after binding to the p62 ZZ domain which is an autophagy receptor. Subsequently, p62 is autophagy-targeted via binding to LC3 protruding from the autophagosome membrane, and the target protein is degraded in lysosomes. In the present invention, an attempt was made to effectively eliminate the target protein by activating p62 using a small molecule ligand that binds to p62 ZZ domain. Until now, there is a PROTAC compound using Ubiquitin proteasome system (UPS) for target protein degradation, but there have been no reports concerning low molecular weight compounds that degrade target proteins using autophagy. When autophagy is used unlike PROTAC, it is possible not only to degrade proteins that cannot be degraded by PROTAC, such as misfolded protein aggregates, membrane-bound proteins, and subunits of complexes, but also to degrade intracellular structures (inflammasome, stress granule, etc.), organelles (endoplasmic reticulum, mitochondria, peroxysome, etc.) and pathogens (virus, bacteria, etc.) that have invaded the cells. Through such target degradation, prophylactic and therapeutic effects can be expected in various diseases.

p62 protein is important for the initiation of autophagosome formation, which is a mediator in selective autophagy mechanism, and for the delivery of the content, i.e., the target protein. It has been observed that the novel AUTOTAC chimeric compound according to the present invention induces self-oligomerization of p62 via p62 activation. In addition, it was confirmed that the target protein was delivered to autophagosomes through such self-oligomerization, and thus the target protein was degraded in lysosomes.

Since the AUTOTAC chimeric compound according to the present invention can not only induce intracellular autophagy but also induce autophagosome targeting of target proteins, and thus enable selective degradation under autophagy mechanism of proteins that cannot be targeted by a conventional enzyme inhibition method, it can provide a novel therapeutic agent.

Advantageous Effects

The AUTOTAC chimeric compound according to the present invention has a structure in which a target-binding ligand (TBL) and a ligand binding to the ZZ domain of p62 protein, i.e., an autophagy-targeting ligand (ATL), are connected via a linker. The autophagy is activated via an autophagy-targeting ligand to bring the target protein to autophagosome and degrade it in lysosomes.

The present invention is a platform technology capable of degrading a desired target protein when connecting a ligand of a protein to be degraded to an autophagy targeting ligand-linker, and thus is applicable as a drug for preventing, ameliorating and treating various diseases.

BRIEF DESCRIPTION OF THE DRAWINGS

FIG. 1 shows a schematic diagram showing the configuration of a novel AUTOTAC chimeric compound according to the present invention, and showing that the compound binds to the p62 protein and simultaneously to the target proteins, organelles and aggregates, which are delivered to autophagosomes, which are the mediators of macroautophagy via the p62 protein, and finally degraded by lysosomes.

FIGS. 2a, 2b and 2c are an immunoblot assay result showing the oligomerization and high molecular weight aggregation efficacy of the corresponding p62 protein by the AUTOTAC compounds. These show that the oligomerization and high molecular weight aggregation of the p62 protein increase according to the treatment with the compounds. Immunoblotting shows representative results from three or more independent experiments.

FIG. 3 is an immunoblot assay result showing the degradation efficacy of the corresponding target protein by the AUTOTAC compounds according to the present invention. This shows that the target protein level decreases according to the treatment with the compounds. Immunoblotting shows representative results from three or more independent experiments.

FIGS. 4a and 4b are an immunoblot assay result showing that the degradation efficacy mechanism of the corresponding target protein is mediated by the AUTOTAC compounds according to the present invention through an autophagy-lysosome pathway. This shows that the target protein level is decreased by treating with the compounds, and the target protein level increases again when treated with hydroxychloroquine (HCQ) which is an autophagy-lysosome pathway inhibitor. Immunoblotting shows representative results from three or more independent experiments.

FIGS. 5a, 5b and 5c are an immunoblot assay result showing that the target protein degradation efficacies of the AUTOTAC chimeric compounds of the present invention are respectively superior to the target protein degradation efficacies of the p62 ligand alone or the target-binding ligand. This shows that the target protein level after treatment with the AUTOTAC chimeric compound is significantly decreased as compared with that after treatment with the p62 ligand or the target protein ligand. Immunoblotting shows representative results from three or more independent experiments.

FIGS. 6a, 6b and 6c are immunofluorescence staining assay results showing the efficacy of delivering the target protein and p62 protein together by the AUTOTAC chimeric compounds according to the present invention to autophagy. It can be confirmed that after treatment with the compounds, the intracellular puncta and co-existence of the target proteins and the p62 protein with the AUTOTAC compounds increase gradually.

DETAILED DESCRIPTION OF THE EMBODIMENTS

Hereinafter, the present invention will be described in more detail.

The present invention provides a chimeric compound comprising a p62 ligand (Autophagy Targeting Ligand, ATL), a target-binding ligand (TBL) and a linker, and a method of using the aforementioned compound to deliver target proteins, organelles and aggregates together with p62 to autophagosome, which is a mediator of macroautophagy, and degrade them in lysosome. Through such a method, the present invention provides a method for preventing, ameliorating or treating diseases by delivering disease-causing proteins, organelles and aggregates to autophagy and degrading them, and a composition for autophagy activation of pathological proteins, organelles and aggregates associated with diseases, and for the prevention, amelioration or treatment of the diseases, comprising the above-mentioned complex (hereinafter also referred to as "chimeric compound").

The present inventors have found that by using the p62 ligand, such a p62 ligand can activate autophagy to effectively deliver target proteins, organelles and aggregates to autophagosomes and eliminate them. The inventors have also found that when using the ligand in combination with a ligand capable of binding to the above pathological protein, it exhibits excellent elimination efficacy of pathological proteins and aggregates, and unlike conventional PROTAC compounds, there is no need to optimize the length of linker for forming a ternary complex (target protein-linker-E3 ligase ligand) for the folding of pathological proteins, E3 ligase selectivity and effective degradation. The novel chimeric compound developed by the present inventors in which a ligand of p62 and a target-binding ligand that binds to the target protein are connected via a linker is named AUTOTAC (AUTOphagy Targeting Chimera).

A feature of the present invention is a technique capable of degrading a desired protein by connecting a ligand of a protein to be degraded to a linker connected with a p62 ligand. That is, the chimeric compound in which the p62 ligand and the target-binding ligand are connected by a linker is a bifunctional small molecule, and a target protein that is degraded near the p62 associated with the autophagy of the protein binds to the ligand targeting them, thereby forming a structure that can easily degrade the target protein. The gist of the invention resides in that a therapeutic effect is expected by connecting to p62 a protein associated with various diseases in which prevention or treatment is required, and degrading the target protein in question.

In a preferred embodiment, the chimeric compound comprising the p62 ligand, the target-binding ligand and the linker according to the present invention is in the form of a chimeric compound in which the p62 ligand and the target-binding ligand are connected via a linker, more preferably, it may have the structure of the following Chemical Formula 1.

[Chemical Formula 1]

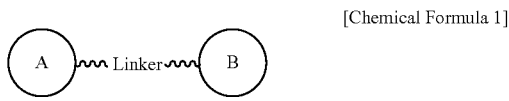

wherein, A represents a target-binding ligand, and B represents a p62 ligand. In Chemical Formula 1, A and B may be each connected to at least one linker.

In the present invention, the target-binding ligand is a ligand that binds to a specific target protein in the body, more specifically, pathological proteins causing a disease to be targeted, or organelles or aggregates. Such target proteins include, but are not limited to, preferably proteins associated with cancer, and proteins associated with various proteinopathic diseases. These target-binding ligands can be used without particular limitation as long as they are those binding to proteins associated with diseases to be prevented, ameliorated and treated, preferably target proteins, organelles or aggregates, associated with diseases, cancer, proteinopathic diseases, intractable diseases or genetic diseases caused by pathological proteins. Specific embodiments may include, but are not limited to, one or more selected from the group consisting of compounds shown in Table 1 below or a derivative structure derived from these structures.

The "derivative" structure means a structure in which a part of the structure of the target-binding ligand is modified by binding to a linker (e.g., the linking portion between the target-binding ligand and the linker is changed by the amide group due to the binding of the carboxyl group in the substituent to the linker having an amine group).

TABLE 1

| Target-binding ligand structure | Name | Related diseases |
|---|---|---|
| 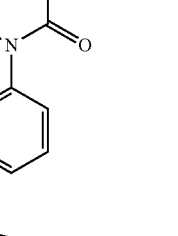 | LCS-1 | Aamyotrophic lateral sclerosis, Frontotemporal lobar degeneration) |
| 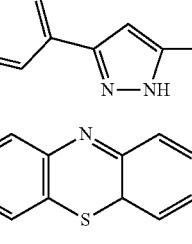 | Anel38b | Parkinson's disease, prion disease |
| 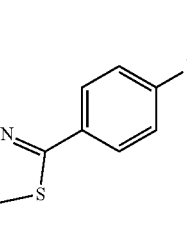 | Azure A | Alzheimer's disease |
| 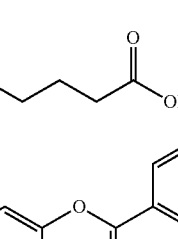 | BTA-1 | Alzheimer's disease, Huntington's disease |
| 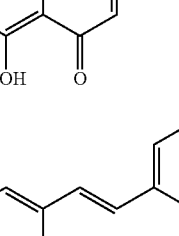 | 4-phenylbutyric acid (4-PBA) | Protein aggregate-related degenerative brain disease |
| 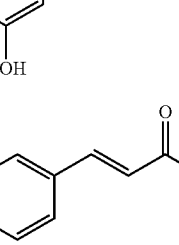 | Baicalein | Protein aggregate-related degenerative brain disease |
|  | Resveratrol | Protein aggregate-related degenerative brain disease |
|  | Curcumin | Protein aggregate-related degenerative brain disease |

TABLE 1-continued

| Target-binding ligand structure | Name | Related diseases |
|---|---|---|
| | Beta-Estradiol | Breast cancer |
| | Riluzole | Protein aggregate-related degenerative brain disease |
| | (Z)-4-OHT ((Z)-4-hydroxytamoxifen) | Breast cancer |
| | PHTPP | Kidney cancer |
| | Vinclozolin | Prostate cancer |
| | Fumagillin | Various cancers (angiogenesis and cancer metastasis) |

TABLE 1-continued
| Target-binding ligand structure | Name | Related diseases |
|---|---|---|
| 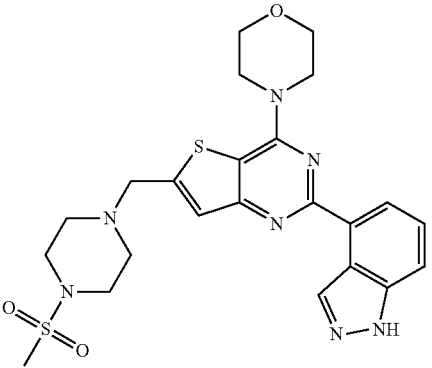 [SMILES: CS(=O)(=O)N1CCN(Cc2cc3nc(-c4cccc5[nH]ncc45)nc(N4CCOCC4)c3s2)CC1] | Pictisilib | Various cancers (PI3K-mediated cancer cell growth) |
| 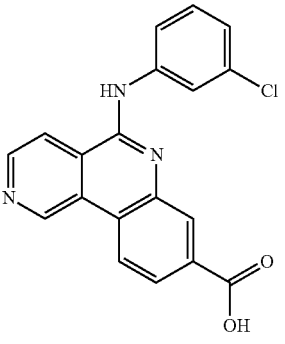 [SMILES: O=C(O)c1ccc2c(c1)nc(Nc1cccc(Cl)c1)c1ccncc12] | Silmitasertib | Various cancers (CSK2-mediated cancer cell growth) |
| 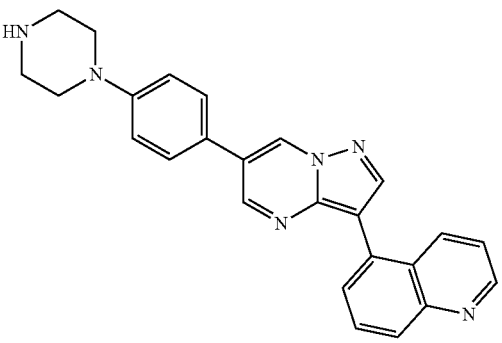 [SMILES: c1cc(-c2cnn3cc(-c4ccc(N5CCNCC5)cc4)cnc23)c2cccnc2c1] | LDN-212854 | Various cancers (BMPR1-mediated cell cancer growth) |
| 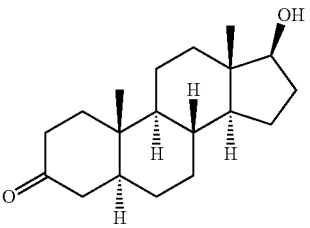 | Dihydrotestosterone (DHT) | Prostate cancer |

TABLE 1-continued

| Target-binding ligand structure | Name | Related diseases |
|---|---|---|
| 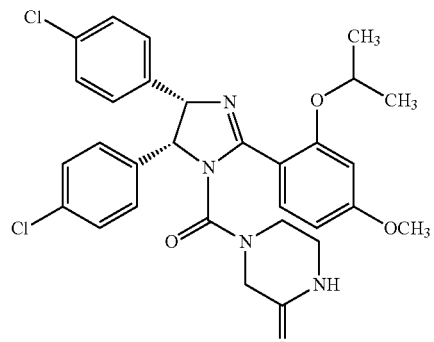 | Nutilin-3a | Various cancers (MDM2 - mediated cancer cell growth) |
| 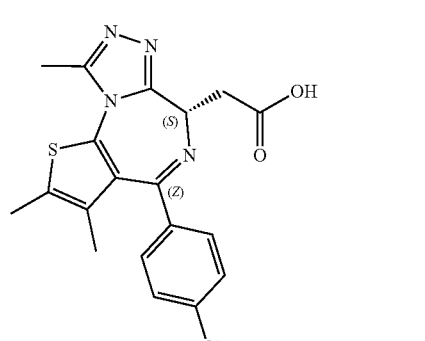 | JQ-1 | Various cancers (BRD 4 - mediated cancer cell growth) |
| 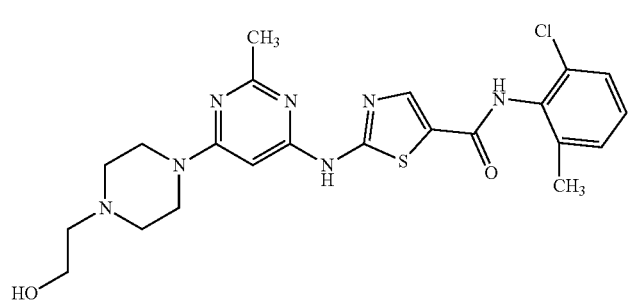 [SMILES: Cc1nc(Nc2ncc(C(=O)Nc3c(C)cccc3Cl)s2)cc(N2CCN(CCO)CC2)n1] | Dasatinib | Chronic myelogenous leukemia, acute myelogenous leukemia, acute lymphoblastic leukemia |
| 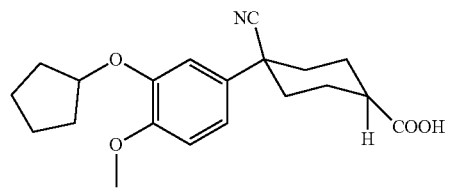 [SMILES: COc1ccc(C2(C#N)CCC(C(=O)O)CC2)cc1OC1CCCC1] | Cilomilast | Various cancers (PDE4-mediated cancer cell growth) |
| 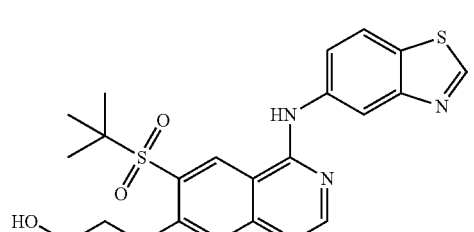 | GSK2983559 | Various cancers (RIPK2-mediated cancer cell growth) |

TABLE 1-continued

| Target-binding ligand structure | Name | Related diseases |
|---|---|---|
| 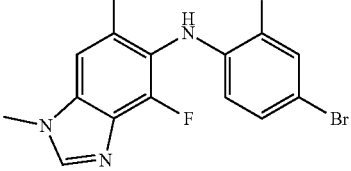 | Selumetinib | Various cancers (MEK-mediated cancer cell growth) |
| 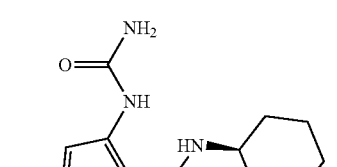 | AZD7762 | Various cancers (Chk1, Chk2-mediated cancer cell growth) |
| 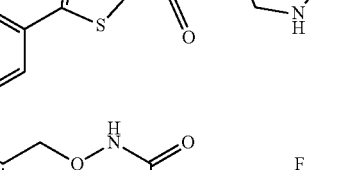 | PD0325901 | Various cancers (MEK-mediated cancer cell growth) |
| 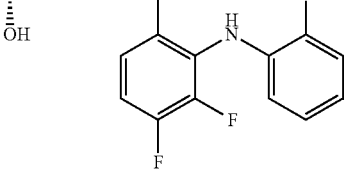 | Rolipram | Chronic myelogenous leukemia, acute myelogenous leukemia, acute lymphoblastic leukemia |
| 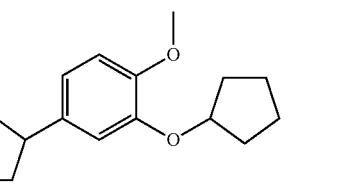 | GSK583 | Various cancers (RIPK2-mediated cancer cell growth) |

The linker connecting A and B in Chemical Formula 1 may be used without limitation as long as it has a structure in which both A and B are structurally connected. For example, such a linker may be -Q-(CH$_2$CH$_2$O)$_x$—(CH$_2$)$_y$—P—, or -Q-(CH$_2$CH$_2$CH$_2$O)$_x$—(CH$_2$)$_y$—P—, or -Q-(CH$_2$CH$_2$NH)$_x$—(CH$_2$)$_y$—P—, or -Q-(CH$_2$CH$_2$CONH)$_x$—(CH$_2$)$_y$—P— (where Q includes —NH—, —O—, =N—, —N(CH$_3$)—, which is a portion modified by binding to the target-binding ligand; P incudes —NH—, —O—, —CH$_2$—, —C(=O)—, which is a portion modified by binding to p62 ligand; x is an integer of 0 to 4; and y is an integer of 0 to 3), but is not limited thereto. Preferably, the bond between P and the p62 ligand may be —CONH—, —O—, —NH—, —NHCO—, or —COO—, In order to form such a bond, a portion of the p62 ligand, e.g., the Rc portion and the portion of the target-binding ligand, can be structurally modified. These modification methods are well known in the art.

In the present invention, the p62 ligand means p62, more specifically, a material that binds to the ZZ domain of p62. Due to binding to the p62 ZZ domain, these p62 ligands increase the oligomerization of p62 and activates autophagy, specifically, macroautophagy. In a preferred embodiment, the p62 ligand may have a structure of the following Chemical Formula 2.

[Chemical Formula 2]

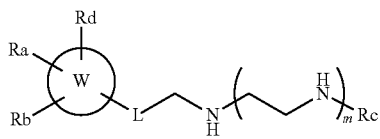

wherein,

W is C6-C10 aryl;

L is —$(CH_2)_{n1}$— or —O—$(CH_2)_{n2}$—CH(OH)—, provided that O in the —O—$(CH_2)_{n2}$—CH(OH)— is bonded to a benzene ring, where n1 is an integer of 1 to 4;

n2 is an integer of 1 to 4;

m is an integer of 0 to 2;

$R_a$ is $R_1$ or —$OR_1$, where $R_1$ is hydrogen or —$(CH_2)_{n3}$—$R'_1$, $R'_1$ is phenyl which is unsubstituted or substituted by hydroxy, halogen, $C_{1-4}$ alkyl, $C_{1-4}$ alkoxy, nitro, amino, ($C_{1-4}$ alkyl)amino, or di($C_{1-4}$ alkyl)amino, n3 is an integer of 1 to 6;

$R_b$ is —$OR_2$, where $R_2$ is hydrogen or —$(CH_2)_{n4}$—$R'_2$, $R'_2$ is phenyl which is unsubstituted or substituted by hydroxy, halogen, $C_{1-4}$ alkyl, $C_{1-4}$ alkoxy, nitro, amino, ($C_{1-4}$ alkyl)amino, or di($C_{1-4}$ alkyl)amino, n4 is an integer of 1 to 6;

$R_c$ is —$(CH_2)_{n5}$—OH, —$(CH_2)_{n5}$—NH—C(=NH) $NH_2$, —C(=NH) $NH_2$, —CH($R_3$)—COOH, or —CH(COO—$R_4$)—$CH_2CH_2CH_2$—NH—C(=NH) $NH_2$, —$(CH_2)_{n5}$—O—$(CH_2)_{n5}$—OH, —CONH$(CH_2)_{n5}$—OH, —CO$(CH_2)_{n6}$—OH, —$(CH_2)_{n6}$—CH($NH_2$)—COOH, —$(CH_2)_{n6}$—$CONH_2$, n5 is an integer of 2 to 4, n6 is an integer of 1 to 4, $R_3$ is hydrogen or $C_{1-4}$ alkyl, $R_4$ is $C_{1-4}$ alkyl, and $R_d$ is hydrogen, halogen, $C_{1-4}$ alkoxy or $C_{1-4}$ alkyl.

Preferably, the W may be phenyl.

Preferably, the L is —$(CH_2)_{n1}$— or —O—$(CH_2)_{n2}$—CH(OH)—, provided that O in the —O—$(CH_2)_{n2}$—CH(OH)— is bonded to a benzene ring.

Preferably, the n1 may be an integer of 0 to 1.

Preferably, the n2 may be an integer of 1 to 2.

Preferably, the $R_a$ may be hydrogen or —O—$(CH_2)_{n3}$—$R'_1$.

Preferably, the $R'_1$ may be phenyl that is unsubstituted or substituted by hydroxy, fluoro, chloro, bromo, methyl, ethyl, methoxy, ethoxy, nitro, amino or dimethylamino.

Preferably, the n3 may be an integer of 1 to 4.

Preferably, the $R_b$ may be hydroxy, or —O—$(CH_2)_{n4}$—$R'_2$.

Preferably, the $R'_2$ may be phenyl which is unsubstituted or substituted by hydroxy, fluoro, chloro, bromo, methyl, ethyl, methoxy, ethoxy, nitro, amino or dimethylamino.

Preferably, the n4 may be an integer of 1 to 4.

Preferably, the $R_c$ may be —$(CH_2)_{n5}$—OH, —$(CH_2)_{n5}$—NH—C(=NH) $NH_2$, —C(=NH) $NH_2$, —$(CH_2)_{n5}$—O—$(CH_2)_{n5}$—OH, —CONH$(CH_2)_{n5}$—OH, —CO$(CH_2)_{n6}$—OH, —$(CH_2)_{n6}$—CH($NH_2$)—COOH, or —$(CH_2)_{n6}$—$CONH_2$.

Preferably, the n5 may be an integer of 2 to 3. Preferably, the n6 may be an integer of 1 to 2. Preferably, the $R_d$ may be hydrogen, halogen, $C_{1-2}$ alkoxy or $C_{1-2}$ alkyl.

For binding to the linker, such a p62 ligand may be connected to the linker in the form of a derivative in which some groups have been modified in a form that facilitates binding to the linker. This can be changed by those skilled in the art appropriately using known techniques depending on the type of p62 ligand, the type of linker, and their binding form, and these modified derivative forms are also included in the p62 ligand of the present invention.

In a specific embodiment, the AUTOTAC chimeric compounds according to the present invention can be compounds shown in Table 2 below, but are not limited thereto.

TABLE 2

| | Chemical Structure | Name of Compound |
|---|---|---|
| Compound 1 | 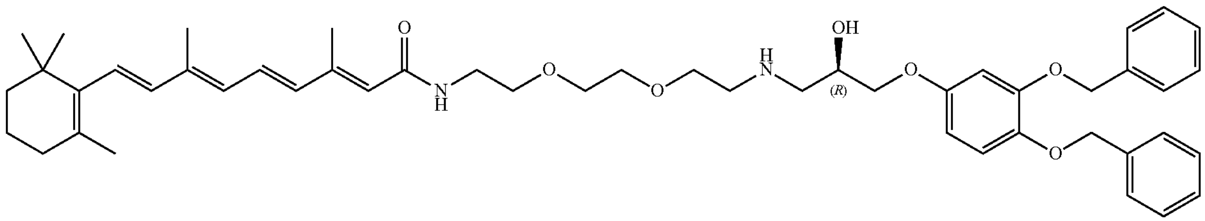 | (2E,4E,6E,8E)-N-(2-(2-(2-((R)-3-(3,4-bis(benzyloxy)phenoxy)-2-hydroxypropyl)amino)ethoxy)ethyl)-3,7-dimethyl-9-(2,6,6-trimethylcyclohex-1-en-1-yl)nona-2,4,6,8-tetraenamide |
| Compound 2 | 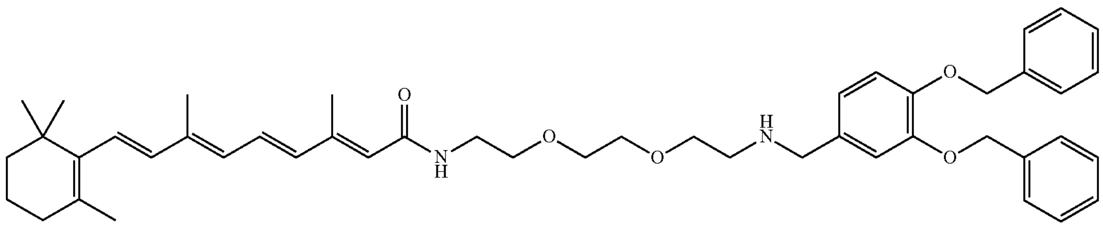 [SMILES: CC1=C(/C=C/C(C)=C/C=C/C(C)=C/C(=O)NCCOCCOCCNCc2ccc(OCc3ccccc3)c(OCc3ccccc3)c2)C(C)(C)CCC1] | (2E,4E,6E,8E)-N-(2-(2-(3,4-bis(benzyloxy)benzyl)amino)ethoxy)ethyl)-3,7-dimethyl-9-(2,6,6-trimethylcyclohex-1-en-1-yl)nona-2,4,6,8-tetraenamide |
| Compound 3 | 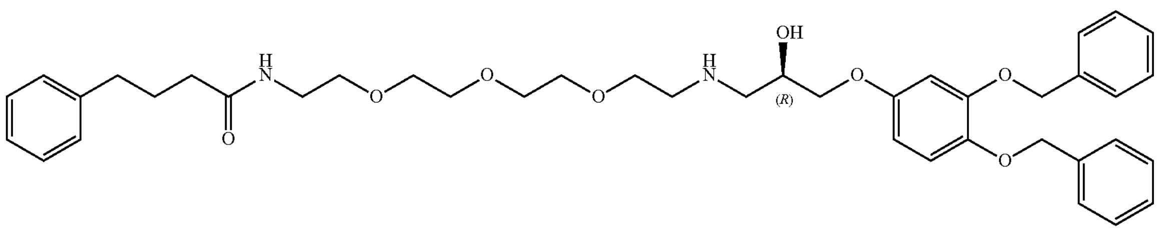 | (R)-N-(15-(3,4-bis(benzyloxy)phenoxy)-14-hydroxy-3,6,9-trioxa-12-azapentadecyl)-4-phenylbutanamide |
| Compound 4 | 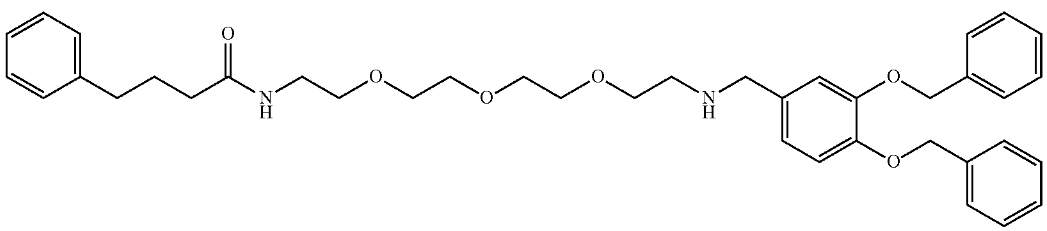 [SMILES: O=C(CCCc1ccccc1)NCCOCCOCCOCCNCc1ccc(OCc2ccccc2)c(OCc2ccccc2)c1] | N-(1-(3,4-bis(benzyloxy)phenyl)-5,8,11-trioxa-2-azatridecan-13-yl)-4-phenylbutanamide |

TABLE 2-continued

| | Chemical Structure | Name of Compound |
|---|---|---|
| Compound 5 | 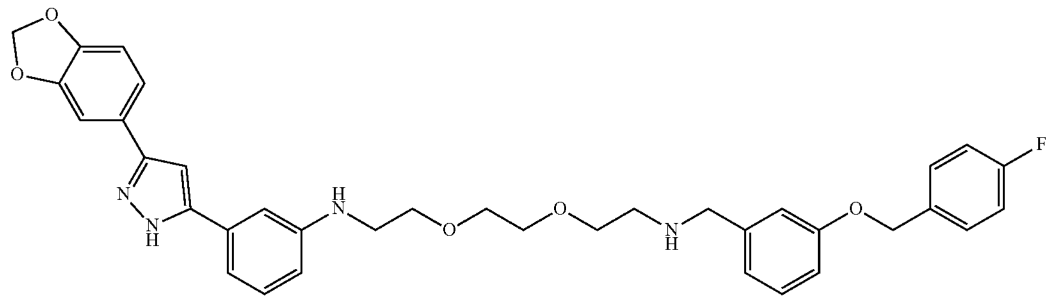 [SMILES: Fc1ccc(COc2cccc(CNCCOCCOCCNc3cccc(-c4cc(-c5ccc6c(c5)OCO6)n[nH]4)c3)c2)cc1] | 3-(3-(benzo[d][1,3]dioxol-5-yl)-1H-pyrazol-5-yl)-N-(2-(2-((3-((4-fluorobenzyl)oxy)benzyl)amino)ethoxy)ethoxy)ethyl)aniline |
| Compound 6 | 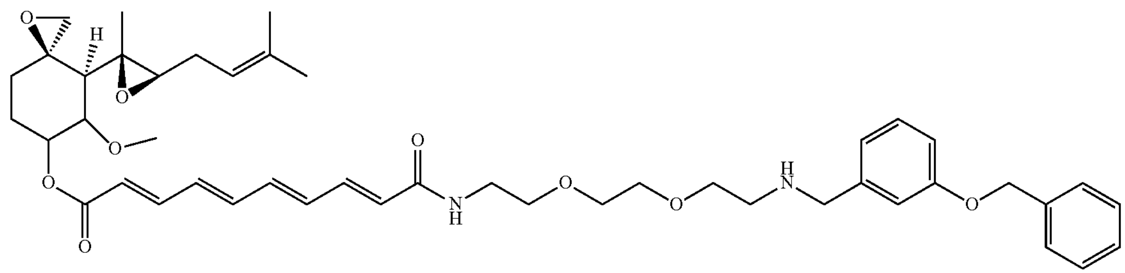 [SMILES: COC1C(OC(=O)/C=C/C=C/C=C/C=C/C(=O)NCCOCCOCCNCc2cccc(OCc3ccccc3)c2)CC[C@]2(CO2)[C@H]1[C@@]1(C)O[C@@H]1CC=C(C)C] | (3R,4S,5S,6R)-5-methoxy-4-((2R,3R)-2-methyl-3-(3-methylbut-2-en-1-yl)oxiran-2-yl)-1-oxaspiro[2.5]octan-6-yl(13E,15E,17E,19E)-1-(3-(benzyloxy)phenyl)-12-oxo-5,8-dioxa-2,11-diazahenicosa-13,15,17,19-tetraene-21-oate |
| Compound 7 | 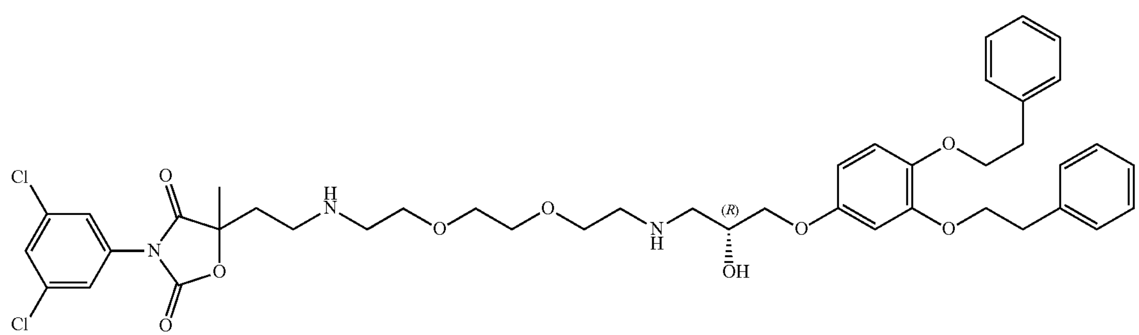 | 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione |

TABLE 2-continued

| | Chemical Structure | Name of Compound |
|---|---|---|
| Compound 8 | 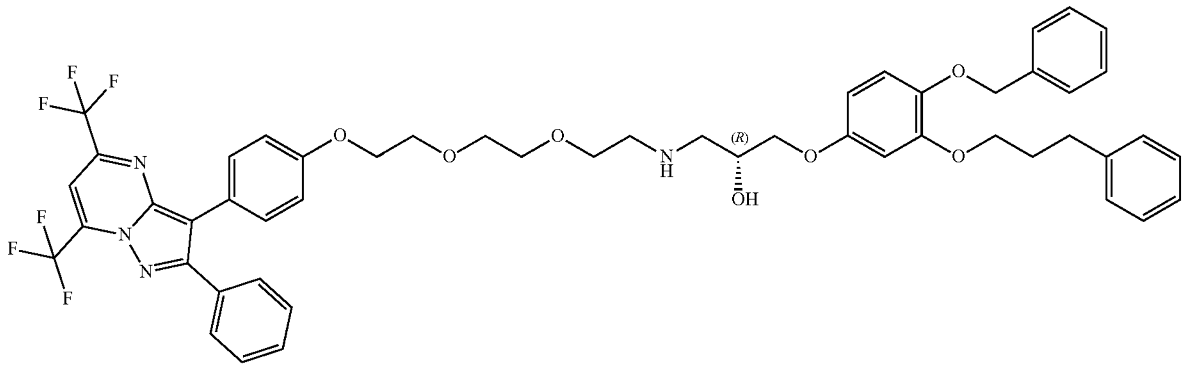 | (R)-1-(4-(benzyloxy)-3-(3-phenylpropoxy)phenoxy)-3-((2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol |
| Compound 9 | 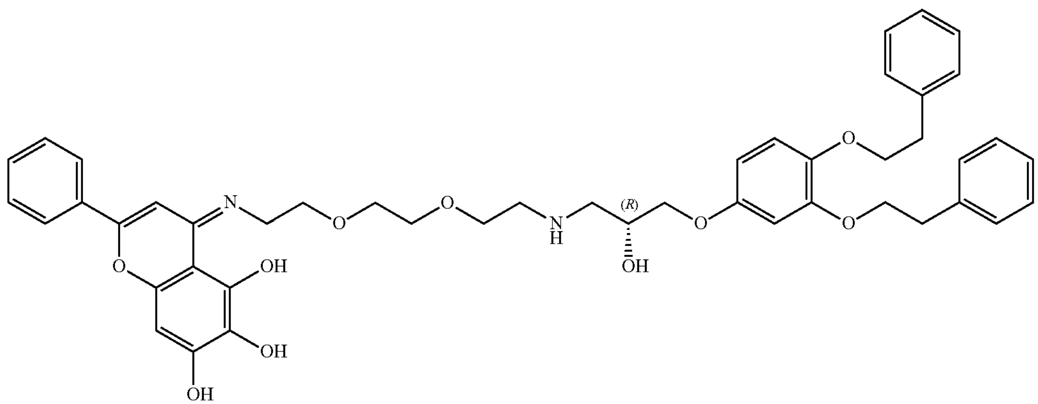 | (R,Z)-4-((2-(2-((3-(3,4-diphenethoxyphenoxy)-2-hydroxypropyl)amino)ethoxy)ethyl)imino)-2-phenyl-4H-chromene-5,6,7-triol |
| Compound 10 | 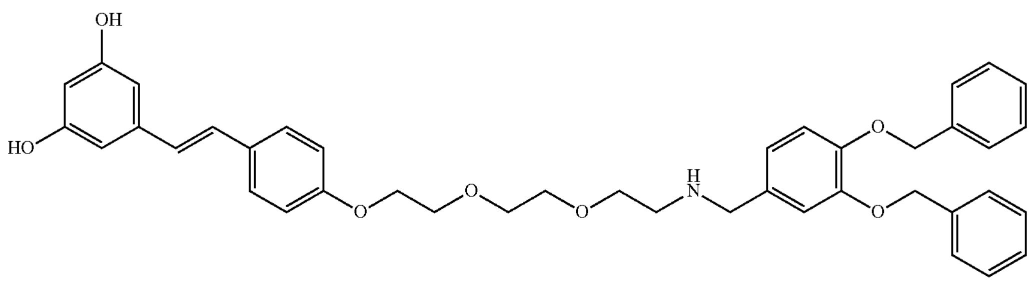 [SMILES: Oc1cc(O)cc(/C=C/c2ccc(OCCOCCOCCNCc3ccc(OCc4ccccc4)c(OCc4ccccc4)c3)cc2)c1] | (E)-5-(4-(2-(2-((3,4-bis(benzyloxy)benzyl)amino)ethoxy)ethoxy)styryl)benzene-1,3-diol |

TABLE 2-continued

| | Chemical Structure | Name of Compound |
|---|---|---|
| Compound 11 | 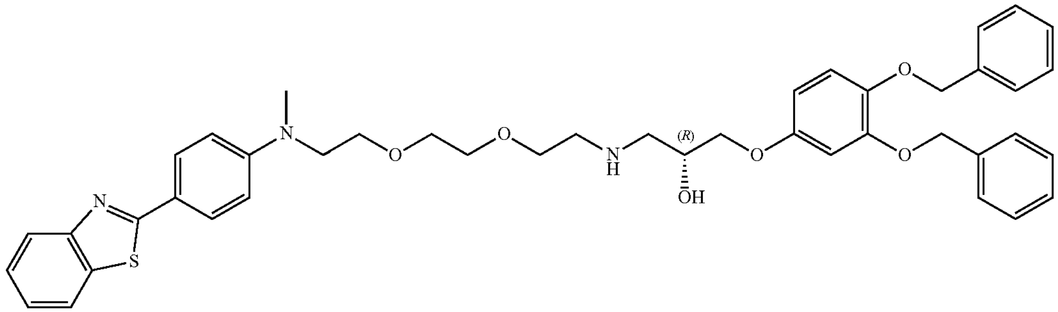 | (R)-2-(4-(benzo[d]thiazol-2-yl)phenyl)-14-(3,4-bis(benzyloxy)phenoxy)-5,8-dioxa-2,11-diazatetradecane-13-ol |
| Compound 12 | 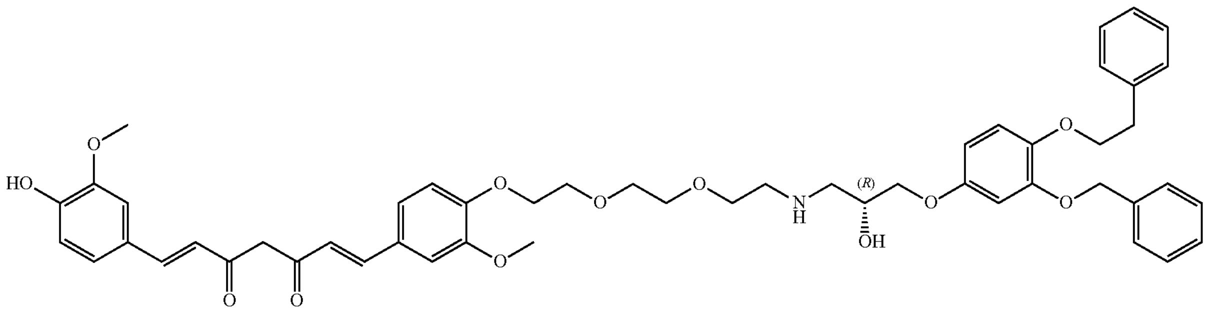 | (1E,6E)-1-(4-(2-(2-(((R)-3-(benzyloxy)-4-phenethoxyphenoxy)-2-hydroxypropyl)amino)ethoxy)ethoxy)-3-methoxyphenyl)-7-(4-hydroxy-3-methoxyphenyl)hepta-1,6-diene-3,5-dione |
| Compound 13 | 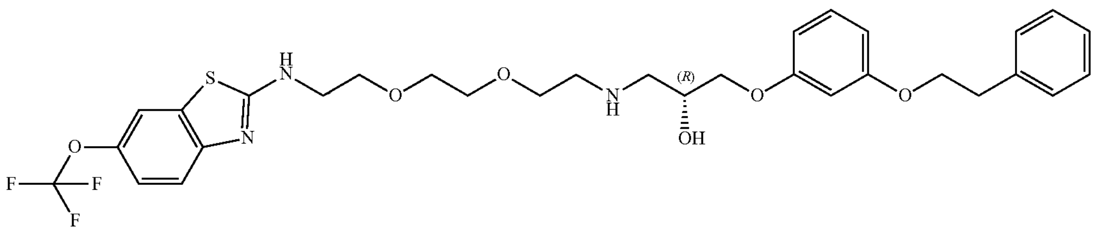 | (R)-1-(3-phenethoxyphenoxy)-3-((2-(2-((6-(trifluoromethoxy)benzo[d]thiazol-2-yl)amino)ethoxy)ethyl)amino)propan-2-ol |

Meanwhile, the compounds of the present invention may exist in the form of a pharmaceutically acceptable salt. As the salt, an addition salt formed by pharmaceutically acceptable free acids may be useful. The term "pharmaceutically acceptable salt" used herein refers to any organic or inorganic addition salt of the compounds represented by Chemical Formulae 1 to 3, in which the adverse effect caused by the salt does not impair the beneficial effect of the compound at a concentration exhibiting relatively non-toxic and non-harmful effective activity to a patient.

The acid addition salt may be prepared by a common method, for example, by dissolving a compound in an excess amount of aqueous acid solution and precipitating the resulting salt using a water-miscible organic solvent, such as methanol, ethanol, acetone or acetonitrile. Alternatively, an equimolar amount of a compound and an acid in water or alcohol (e.g., glycol monomethyl ether) can be heated, and subsequently, the resulting mixture can be dried by evaporating, or precipitated salts can be filtered under suction.

In this case, the free acid may be an inorganic acid or an organic acid. Examples of the inorganic acids include, but are not limited to, hydrochloric acid, phosphoric acid, sulfuric acid, nitric acid and stannic acid. Examples of the organic acids include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid.

In addition, a pharmaceutically acceptable metal salt may be prepared using a base. An alkali metal or alkaline earth metal salt may be obtained, for example, by dissolving a compound in an excess amount of alkali metal hydroxide or alkaline earth metal hydroxide solution, filtering the undissolved compound salt, and then evaporating the filtrate until dry. At this time, as the metal salts, particularly sodium, potassium or calcium salts are pharmaceutically suitable, but the present invention is not limited thereto. Also, the corresponding silver salts may be obtained by reacting an alkali metal or alkaline earth metal salt with a proper silver salt (e.g., silver nitrate).

Pharmaceutically acceptable salts of the compound of the present invention, unless otherwise indicated herein, include salts of acidic or basic groups, which may be present in the compound of Chemical Formula 1. For example, the pharmaceutically acceptable salts include sodium, calcium and potassium salts of hydroxy group, and other pharmaceutically acceptable salts of amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate). The salts may be prepared using a salt preparation method known in the art.

Salts of the compounds of Chemical Formula 1 of the present invention are pharmaceutically acceptable salts, and can be used without particular limitation as long as they are salts which exhibit pharmacological activities equivalent to those of the compound of Chemical Formula 1.

In addition, the compounds represented by Chemical Formula 1 according to the present invention include, but are not limited thereto, not only pharmaceutically acceptable salts thereof, but also all solvates or hydrates and all possible stereoisomers that can be prepared therefrom. All stereoisomers of the present compounds (e.g., those which may exist due to asymmetric carbons on various substituents), including enantiomeric forms and diastereomeric forms, are contemplated within the scope of this invention. Individual stereoisomers of the compounds of the present invention may, for example, be substantially free of other isomers (e.g., as a pure or substantially pure optical isomer having a specified activity), or may be admixed, for example, as racemates or with all other, or other selected, stereoisomers. The chiral centers of the compounds of the present invention may have the S or R configuration as defined by the IUPAC 1974 Recommendations. The racemic forms can be analyzed by physical methods, such as fractional crystallization, separation or crystallization of diastereomeric derivatives or separation by chiral column chromatography. The individual optical isomers can be obtained from the racemates by any suitable method, including without limitation, salt formation with an optically active acid followed by crystallization.

The solvate and stereoisomer of the compound represented by Chemical Formula 1 may be prepared from the compound represented by Chemical Formula 1 using methods known in the art.

Furthermore, the compound represented by Chemical Formula 1 according to the present invention may be prepared either in a crystalline form or in a non-crystalline form, When the compound is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

The compound of Chemical Formula 1 according to the present invention may be prepared by the following exemplary method, and specific examples thereof are the same as in Reaction Schemes described in Examples below.

In the preparation method of the present invention, the reactants used in Reaction Schemes may be commercially available compounds, or may be synthesized by performing one or more reactions known in the art as they are or by appropriately modifying the reactions. For example, in consideration of the presence, type and/or position of reactive functional groups and/or hetero elements contained in the skeletal structure, the reactants may be synthesized by performing one or more reactions in a series of order, but are not limited thereto.

The compound of Chemical Formula 1 according to the present invention acts as a chimeric ligand that binds to the ZZ domain of p62 and simultaneously binds to the target protein, organelles and aggregates, thereby activating the function of p62, and delivering target proteins, organelles (endoplasmic reticulum, mitochondria, peroxysome, etc.), intracellular structures (inflammasomes, stress granule, etc.), pathogens (viruse, bacteria, etc.) and aggregates that have invaded the cells to autophagy for degradation, similar to p62.

Therefore, in another aspect, the present invention provides a pharmaceutical composition for autophagy activation comprising the compound of Chemical Formula 1, a pharmaceutically acceptable salt, stereoisomer, hydrate, solvate or prodrug thereof.

The compound of Chemical Formula 1 according to the present invention can eliminate pathological proteins, organelles and aggregates of the pathological protein-related diseases by delivering target proteins, organelles and aggregates to autophagy and degrading them. In addition, the compound of Chemical Formula 1 is a p62 ligand, which binds to the p62 ZZ domain and activates PB1 domain and LIR domain of p62 protein, thereby p62 oligomerization and aggregate formation, and simultaneously increasing the delivery of target proteins, organelles and aggregates along with p62 protein to autophagosome. By the processes above, target proteins, organelles and aggregates are efficiently eliminated (see FIG. 1). Such target protein may be a major protein of pathological protein-related diseases, more preferably at least one selected from the group consisting of prion protein, amyloid precursor protein (APP), alpha-synuclein, superoxide dismutase 1, tau, immunoglobulin, amyloid-A, transthyretin, beta2-microglobulin, cystatin C, apolipoprotein Al, TDP-43, islet amyloid polypeptide, ANF, gelsolin, insulin, lysozyme, fibrinogen, huntingtin, alpha-1-antitrypsin Z, crystallin, c9 open reading frame 72 (c9orf72), glial fibrillary acidic protein, cystic fibrosis transmembrane conductance regulator protein, rhodopsin, and ataxin, and other proteins with a poly-Q stretch.

Therefore, in still another aspect, the present invention provides a pharmaceutical composition comprising an AUTOTAC chimeric compound of Chemical Formula 1, a pharmaceutically acceptable salt, stereoisomer, hydrate, solvate or prodrug thereof. The pharmaceutical composition is for preventing or treating a disease targeted by the target-binding ligand. Such disease may be a target without limitation as long as it can bind to a target-binding ligand, and preferably, it is a cancer or proteinopathies, and more preferably, it includes various diseases that can be expected to have a therapeutic effect when targeting and degrading specific proteins, such as rare or intractable diseases or genetic diseases. The pharmaceutical composition according to the present invention is characterized by directly eliminating the causative protein that induces the aforementioned diseases.

In another aspect, the present invention provides a pharmaceutical composition for autophagic delivery or degradation of disease-causing pathological proteins and misfolded proteins, including the compound of Chemical Formula 1, a pharmaceutically acceptable salt, stereoisomer, solvate, hydrate or prodrug thereof.

The term "proteinopathy" or "disease linked to protein aggregation" as used herein, refers to those diseases which are characterized by the presence of misfolded protein aggregates, and examples thereof include, but are not limited to, neurodegenerative diseases, alpha-1 antitrypsin deficiency, keratopathy, retinitis pigmentosa, type 2 diabetes, cystic fibrosis, and the like.

The term "aggregation", in accordance with the present invention, refers to the formation of oligomeric or multimeric complexes of typically one or more types of proteins, which may be accompanied by the integration of additional biomolecules, like carbohydrates, nucleic acids and lipids, into the complexes. Such aggregated proteins may form deposits in specific tissue, more preferably in nerve tissue or tissue of the brain. The extent of aggregation depends on the particular disease.

The neurodegenerative diseases herein are preferably selected from the group consisting of Lyme borreliosis, fatal familial insomnia, Creutzfeldt-Jakob Disease (CJD), multiple sclerosis (MS), dementia, Alzheimer's disease, epilepsy, Parkinson's disease, stroke, Huntington's disease, Picks disease, amyotrophic lateral sclerosis (ALS), spinocerebellar ataxias, other Poly-Q diseases, hereditary cerebral amyloid angiopathy, familial amyloid polyneuropathy, primary systemic amyloidosis (AL amyloidosis), reactive systemic amyloidosis (AA amyloidosis), injection-localized amyloidosis, beta-2 microglobulin amyloidosis, hereditary non-neuropathic amyloidosis, Alexander disease and Finnish hereditary systemic amyloidosis.

The dosage of the pharmaceutical composition of the present invention may vary with a broad range depending on weight, age, gender, or health condition a patient, diet, administration period, administration method, excretion and severity of disease. However, the effective dosage is generally about 1 ng to 10 mg/day and particularly about 1 ng to 1 mg/day for an adult (60 kg). As the dosage may vary depending on various conditions, it would be evident to a person skilled in the pertinent art that the dosage may be increased or decreased. Accordingly, the scope of the present invention is not limited by the aforementioned dosage in any way. As for the number of administration, the administration can be made either once or several divided times per day within a desired range, and the administration period is not particularly limited, either.

As used herein, the term "treatment" refers to all actions that alleviate or beneficially change the symptoms of various diseases linked to misfolded protein aggregation, and of diseases via targeted protein degradation, by administering the pharmaceutical composition of the present invention.

As described above, the compound of the present invention exhibits the effects of (1) inducing p62 oligomerization and structural activation, (2) increasing p62-LC3 binding, and (3) increasing the delivery of p62 to autophagosomes, (4) activating autophagy, and finally (5) eliminating targeted proteins. Therefore, the pharmaceutical composition containing this compound as an active ingredient can be used for the prevention, amelioration or treatment of various desired diseases, preferably cancer or proteinopathy.

For example, the composition of the present invention may further include pharmaceutically acceptable carriers, diluents or excipients. The composition can be used in the various forms such as oral dosage forms of powders, granules, tablets, capsules, suspensions, emulsions, syrups, aerosols and injections of a sterile injectable solution, which are formulated by the conventional method according to the purpose of each of the intended use. The composition can be administered through various routes including oral administration or intravenous, intraperitoneal, subcutaneous, rectal and topical administration. Examples of suitable carriers, excipients or diluents which can be included in this composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxy benzoate, propylhydroxy benzoate, talc, magnesium stearate, mineral oil, and the like. In addition, the composition of the present invention may further include fillers, anti-coagulants, lubricants, humectants, fragrances, emulsifiers, preservatives, and the like.

A solid formulation for oral administration includes tablets, pills, powders, granules, capsules and the like, and such solid dosage forms are formulated by mixing the composition of the present invention with one or more excipients, such as starch, calcium carbonate, sucrose, lactose, gelatin and the like. Also, lubricants such as magnesium stearate and talc can be used in addition to simple excipients.

A liquid formulation for oral administration can be illustrated as suspensions, solutions, emulsions, syrups and the like, and can include various excipients such as humectants, sweeteners, fragrances, preservatives and the like, in addition to water and liquid paraffin which are commonly used diluents.

A formulation for parenteral administration includes sterilized aqueous solutions, non-aqueous solvents, suspension agents, emulsion agents, lyophilizing agents and suppository agents. Non-aqueous solvent and suspending agent may include propylene glycol, polyethylene glycol, vegetable oil such as olive oil, and injectable esters such as ethyl oleate. As a substrate for the suppository agent, Witepsol, Macrogol, Tween 61, cacao butter, laurin butter, glycerogelatin or the like may be used. On the other hand, injections may include conventional additives such as solubilizing agents, isotonic agents, suspending agents, emulsifiers, stabilizers, or preservatives.

The formulation may be prepared according to conventional mixing, granulation or coating methods, and contains an active ingredient in an amount effective for medical treatment, specifically for the prevention, amelioration or treatment of diseases linked to protein aggregation.

In this case, the composition of the present invention is administrated in a pharmaceutically effective amount. The term "pharmaceutically effective amount" as used herein refers to an amount which is sufficient to treat the disease at a reasonable benefit/risk ratio applicable for any medical treatment, and also which is enough to not cause side effects. The level of effective amount can be determined depending on patient's health condition, disease type, severity of the disease, activity of the drug, sensitivity on the drug, administration method, administration time, administration route, excretion rate, treatment duration, combination, factors including other medicines used at the same time and other factors well-known in the medical field. The composition of the present invention may be administered as individual therapy or in combination with other therapies, and it can be administered simultaneously with or sequentially to conventional therapies, and once or multiple times. It is important to administer the minimum amount which can provide the maximum effect without the side effects in consideration of all the above factors, which can be easily determined by those skilled in the art.

For example, the dosage may be increased or decreased depending on administration route, the severity of a disease, gender, weight, age and the like, and the scope of the present invention is not limited by the aforementioned dosage in any way.

A preferred dose of the compound according to the present invention may be varied according to the condition and weight of a patient, the severity of a disease, the type of a drug, and the route and duration of administration, but it may be suitably selected by those skilled in the art.

In another aspect, the present invention provides a method for preventing, ameliorating or treating diseases, preferably cancer, diseases associated with pathological proteins, diseases linked to protein aggregation, comprising administering the pharmaceutical composition of the present invention to a subject in need thereof.

In another aspect, the present invention provides (i) a method of increasing the degradation of a target protein, (ii) a method of increasing the degradation of organelles and structures; (iii) a method of increasing the degradation of viruses and bacteria that have invaded the cells, (iv) a method of delivering drugs or small molecule compounds to autophagy and lysosomes, (v) method of self-oligomerization and autophagy activation of p62, and (vi) a method of increasing the degradation by lysosomes by connecting specific proteins in cells to p62 and delivering them to autophagy, including the compound of Chemical Formula 1, a pharmaceutically acceptable salt, stereoisomer, solvate, hydrate or prodrug thereof.

In still another aspect, the present invention provides a method of using a drug in which a chimeric compound according to the present invention is connected to a therapeutic antibody that specifically binds to a protein exposed on a cell membrane, and delivering such a drug to lysosomes via endosomes. The therapeutic antibody may be used without limitation as long as it exhibits pharmacological activity against a disease requiring treatment.

As used herein, the term "subject" refers to all animals comprising human, monkey, cow, horse, sheep, pig, chicken, turkey, quail, cat, dog, mouse, rat, rabbit, or guinea pig, which have target diseases for the prevention, amelioration or treatment. The target diseases, preferably cancer, diseases associated with pathological proteins, or diseases linked to misfolded protein aggregation can be effectively prevented, ameliorated or treated by administrating the pharmaceutical composition of the present invention to the subject. In addition, since the pharmaceutical composition of the present invention functions as a p62 ligand to activate autophagy, eliminates aggregates of misfolded proteins due to the autophagy activation, and thus exhibits a prophylactic or therapeutic effect of diseases linked to these aggregated proteins, it can exhibit synergistic effects by administration in combination with existing therapeutic agents.

As used herein, the term "administration" means introduction of a prescribed amount of a substance into a patient in certain appropriate method, and the composition of the present invention can be administrated via any of the general routes as long as it can reach a target tissue. For example, intraperitoneal administration, intravenous administration, intramuscular administration, subcutaneous administration, intradermal administration, oral administration, topical administration, intranasal administration, intrapulmonary administration and intrarectal administration may be performed, but the present invention is not limited to these exemplified administration modes. Also, the pharmaceutical composition of the present invention can be administered using any device capable of delivering the active ingredients to target cells. Preferable administration mode and formulation are an intravenous injection, a subcutaneous injection, an intradermal injection, an intramuscular injection, intravenous drip injection, or the like. Injectable formulations may be prepared using saline, aqueous solutions such as Ringer's solution, and non-aqueous solutions, such as vegetable oils, high fatty acid esters (e.g., ethyl oleic acid, etc.), alcohols (e.g., ethanol, benzyl alcohol, propylene glycol, glycerin, etc.). The injectable preparations may include pharmaceutical carriers, including a stabilizer for preventing degeneration (e.g., ascorbic acid, sodium hydrogen sulfite, sodium pyrosulfite, BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzylalcohol, etc.).

In the other aspect, the present invention provides a food composition for the prevention or amelioration of proteinopathies comprising an AUTOTAC chimeric compound of Chemical Formula 1, a pharmaceutically acceptable salt, stereoisomer, hydrate, solvate or prodrug thereof. The food composition is a health functional food and it can be used through formulation itself or be comprised in other health functional foods as an additive of health functional food. The health functional food means food having body modulating function such as prevention or amelioration of diseases, biodefense, immunity, recovery of convalescence, aging inhibition, etc., and it should be harmless to human body when taking in a long term. The mixing amount of active ingredients can be properly decided depending on purpose of use (prevention, health or therapeutic treatment).

The kind of the food is not particularly limited. Examples of food where the above substances can be added are meat, sausage, bread, chocolates, candies, snack, cookies, pizza, ramen, other noodles, gum, dairy products including ice cream, sorts of soup, beverages, tea, drinks, alcohol beverages and vitamin complex, etc., and it includes all the health functional foods in the common sense.

The food composition of the present invention can comprise common ingredients used in preparation of food or food additives, specifically, a flavoring agent; a natural sweetener such as monosaccharides like glucose, fructose, disaccharides like maltose, sucrose, and dextrin, cyclodextrin as a natural carbohydrate, or a synthetic sweetener such as saccharin, aspartame; a nutrient; vitamin; electrolyte; a coloring agent; an organic acid; a protective colloid viscosity agent; pH regulator; a stabilizer; a preservative; glycerin; alcohol; a carbonating agent which is used on carbonated drinks, etc.

In a specific embodiment of the present invention, the novel AUTOTAC chimeric compounds 1 to 13 represented by Chemical Formula 1 were newly synthesized. In addition, in order to evaluate whether the novel AUTOTAC chimeric compounds according to the present invention can increase the phenomenon of autophagy in cultured cells, cell lines primarily expressing the target protein (MCF7, NTERA-2, ACHN, U87-MG, LNCaP, HEK293T) or gene recombinant cell lines (SH-SY5Y-tau, HeLa-HttQ97, PC12-a-synA30P) were treated with the AUTOTAC chimeric compound according to the present invention and cultured, and then target protein degradation activity in cultured cells was confirmed by immunoblotting. As a result, not only the autophagy-mediated degradation effect of each target protein was gradually confirmed according to the concentration treated with the AUTOTAC compounds according to the present invention, but also the degradation efficiency was confirmed to be superior to that of the p62 ligand or target protein ligand constituting the chimeric compound. Thus, it was confirmed that the AUTOTAC compounds according to the present invention activated and oligomerized p62 proteins and thus delivered to autophagosome, and at the same time, selectively and effectively eliminated proteins and their aggregates associated with various target diseases, such as cancer-related proteins or proteinopathies.

EXAMPLE

Hereinafter, the present invention will be described in more detail with reference to Examples. However, these Examples are provided for illustrative purposes only, and the present invention is not intended to be limited by these Examples.

The compound of Formula 1-13 according to the present invention were prepared according to the methods of the following Examples 1 to 13.

TABLE 3

| No. | Code | Name of Chemical Formula |
|---|---|---|
| Example 1 | RTEG-1104 | (2E,4E,6E,8E)-N-(2-(2-(2-(((R)-3-(3,4-bis(benzyloxy)phenoxy)-2-hydroxypropyl)amino)ethoxy)ethoxy)ethyl)-3,7-dimethyl-9-(2,6,6-trimethylcyclohex-1-en-1-yl)nona-2,4,6,8-tetraenamide |
| Example 2 | RTEG-1105 | (2E,4E,6E,8E)-N-(2-(2-(2-((3,4-bis(benzyloxy)benzyl)amino)ethoxy)ethoxy)ethyl)-3,7-dimethyl-9-(2,6,6-trimethylcyclohex-1-en-1-yl)nona-2,4,6,8-tetraenamide |
| Example 3 | PBA-1104 | (R)-N-(15-(3,4-bis(benzyloxy)phenoxy)-14-hydroxy-3,6,9-trioxa-12-azapentadecyl)-4-phenylbutaneamide |
| Example 4 | PBA-1105 | N-(1-(3,4-bis(benzyloxy)phenyl)-5,8,11-trioxa-2-azatridecan-13-yl)-4-phenylbutanamide |
| Example 5 | Anle138b-F105 | 3-(3-(benzo[d][1,3]dioxol-5-yl)-1H-pyrazol-5-yl)-N-(2-(2-(2-((3-((4-fluorobenzyl)oxy))benzyl)amino)ethoxy)ethoxy)ethyl)aniline |
| Example 6 | Fumagillin-105 | (3R,4S,5S,6R)-5-methoxy-4-((2R,3R)-2-methyl-3-(3-methylbut-2-en-1-yl)oxiran-2-yl)-1-oxaspiro[2.5]octan-6-yl(13E,15E,17E,19E)-1-(3-(benzyloxy)phenyl)-12-oxo-5,8-dioxa-2,11-diazahenicosa-13,15,17,19-tetraene-21-oate |
| Example 7 | Vinclozolin-2204 | 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione |
| Example 8 | PHTPP-1304 | (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol |
| Example 9 | Baicalein-2204 | (R,Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol |
| Example 10 | Resveratrol-1105 | (E)-5-(4-(2-(2-(2-((3,4-bis(benzyloxy)benzyl)amino)ethoxy)ethoxy)ethoxy)styryl)benzene-1,3-diol |
| Example 11 | BTA-1-1104 | (R)-2-(4-(benzo[d]thiazol-2-yl)phenyl)-14-(3,4-bis(benzyloxy)phenoxy)-5,8-dioxa-2,11-diazatetradecane-13-ol |
| Example 12 | Curcumin-1204 | (1E,6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione |
| Example 13 | Riluzole-204 | (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol |

In the case of the starting materials for synthesizing the compounds of the present invention, various synthesis methods have been known, and if available on the market, the starting materials may be purchased from the providers. Examples of the reagents suppliers include Sigma-Aldrich, TCI, Wako, Kanto, Fluorchem, Acros, Alfa, Fluka, and the like, but are not limited thereto.

The compounds of the present invention can be prepared from readily available starting materials using the following general methods and procedures. As for typical or preferred process conditions (i.e., reaction temperature, time, molar ratio of reactants, solvents, pressure) and the like, other process conditions may also be used unless stated otherwise. The optimal reaction state may vary depending on the specific reactants or solvent used. Such conditions can be determined by one skilled in the art by conventional optimization procedures.

Hereinafter, the preparation methods of Examples 1 to 13 are described.

Example 1: Preparation of (2E, 4E, 6E, 8E)-N-(2-(2-(2-(((R)-3-(3,4-bis(benzyloxy)phenoxy)-2-hydroxypropyl)amino)ethoxy)ethoxy)ethyl)-3,7-dimethyl-9-(2,6,6-trimethylcyclohex-1-en-1-yl)nona-2,4,6,8-tetraenamide (RTEG-1104)

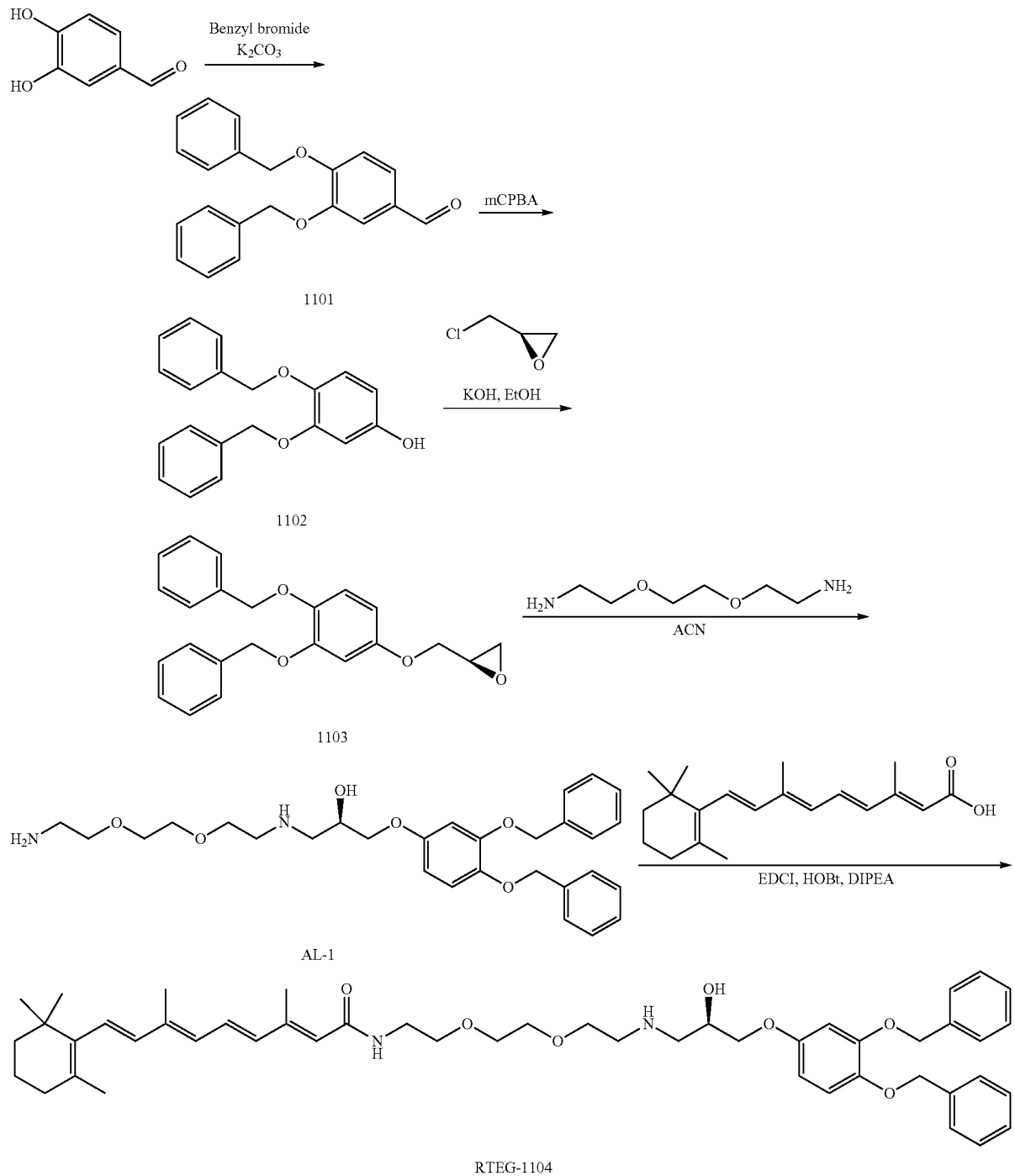

Step 1) Preparation of 3,4-bis(benzyloxy)benzaldehyde (1101)

After 3,4-dihydroxybenzaldehyde (0.50 g, 3.62 mmol) was dissolved in anhydrous DMF (5 ml), potassium carbonate ($K_2CO_3$, 1.50 g, 10.86 mmol) was added and benzyl bromide (0.92 mL, 7.96 mmol) was then slowly added to the reaction and stirred at 60° C. for 4 hours. When the reaction was completed, the reaction mixture was cooled to room temperature, diluted with purified water and extracted twice with diethyl ether (50 ml). The organic layer was washed twice with purified water (50 ml) and then once again with saturated aqueous sodium chloride solution (50 ml). Then, anhydrous sodium sulfate was added to the organic layer and stirred, followed by filtration under reduced pressure. The filtered solution was concentrated and then purified by column chromatography to give 3,4-bis(benzyloxy)benzaldehyde (1101, 1.04 g, yield: 90%). $^1$H NMR (CDCl$_3$, 300 MHz) δ 9.81 (s, 1H), 7.49-7.31 (m, 12H), 7.04 (d, J=8.3 Hz, 1H), 5.27 (s, 2H), 5.22 (s, 2H); ESIMS m/z: 319.33 [M+H]$^+$.

Step 2) Preparation of 3,4-bis(benzyloxy)phenol (1102)

Dichloromethane (15 ml) was added to and dissolved in 3,4-bis(benzyloxy)benzaldehyde (1101, 1.00 g, 3.0 mmol, 1 eq.), and then mCPBA (0.78 g, 4.5 mmol, 1.5 eq.) was added to the reaction and stirred at room temperature for 4 hours. The reaction mixture was diluted with ethyl acetate, washed with saturated aqueous sodium carbonate solution, and then the organic layer was separated. The organic layer was washed with an aqueous sodium chloride solution, then dehydrated with anhydrous sodium sulfate and filtered under reduced pressure. The filtered solution was concentrated and then dissolved in methanol (10 ml) again. 6N NaOH was added thereto and stirred at room temperature for 30 minutes. 4N HCl solution was added to the reaction, and further stirred for 30 minutes. The reaction mixture was diluted with ethyl acetate (50 ml), washed with brine, dehydrated with anhydrous sodium sulfate, and filtrated under reduced pressure. The filtered solution was concentrated and then purified by column chromatography (hexane/ethyl acetate ratio=7/3) to give 3,4-bis(benzyloxy)phenol (1102, 0.87 g, yield: 90%). $^1$H-NMR (CDCl$_3$, 300 MHz): 7.25-7.42 (m, 10H), 6.80 (d, 1H, J=9.0 Hz), 6.48 (d, 1H, J=3.0 Hz), 6.29 (dd, 1H, J=3.0 and 9.0 Hz), 5.08 (d, 4H, J=15 Hz), 4.55 (s, 1H); ESIMS m/z: 307.25 [M+H]$^+$.

Step 3) Preparation of R-2-((3,4-bis(benzyloxy)phenoxy)methyl)oxirane (1103)

3,4-Dibenzyloxyphenol (1102, 306 mg, 1.0 mmol) was diluted with ethanol (10 ml)j, and then aqueous KOH solution (KOH 66 mg, 1.2 mmol, 1 ml) and (R)-2-(chloromethyl) oxirane (410 ul, 5.0 mmol) were added sequentially. The reaction mixture was stirred at room temperature for 5 hours, and then the organic solvent was removed under reduced pressure. The concentrated reaction mixture was again diluted with ethyl acetate, washed with water and then with brine. The extracted organic layer was dehydrated with anhydrous sodium sulfate and then filtered under reduced pressure. The filtered organic layer was concentrated and purified by column chromatography to give pure R-2-((3,4-bis(benzyloxy)phenoxy)methyl)oxirane (1103, 297 mg, yield: 82%), ESIMS m/z: 363.5 [M+H]$^+$.

Step 4) Preparation of (R)-1-((2-(2-(2-aminoethoxy)ethoxy)ethyl)amino-3-(3,4-bis(benzyloxy)phenoxy) propan-2-ol (AL-1)

R-2-((3,4-bis(benzyloxy)phenoxy) methyl)oxirane (1103, 270 mg, 0.75 mmol) was dissolved in anhydrous ethanol (5 ml), and then 2,2'-(ethane-1,2-diylbis(oxy)) bis(ethane-1-amine) (880 mg, 5.9 mmol) was added and stirred at room temperature for 8 hours. After confirming the reaction by TLC, the reaction solvent was concentrated under reduced pressure. Water was added to the concentrated reaction and extracted with dichloromethane (3×5 mL). The extracted organic layer was dehydrated with anhydrous sodium sulfate and then filtered under reduced pressure. The filtered organic layer was concentrated and purified by column chromatography (dichloromethane:methanol=19:1) to give (R)-1-((2-(2-(2-aminoethoxy)ethoxy)ethyl)amino-3-(3,4-bis(benzyloxy)phenoxy)propan-2-ol (AL-1, 267 mg, yield: 70%). ESIMS m/z: 511.5 [M+H]+.

Step 5) (R)-1-((2-(2-(2-aminoethoxy)ethoxy)ethyl) amino-3-(3,4-bis(benzyloxy)phenoxy)propan-2-ol (AL-1, 100 mg, 0.19 mmol) was dissolved in DMF (4 ml), and then 1-ethyl-3-(3-dimethylaminopropyl) carbodiimide (EDCI, 44 mg, 0.285 mmol), hydroxybenzotriazole (HOBt, 38.5 mg, 0.285 mmol) and retinoic acid (60 mg, 0.2 mol) were added sequentially. Then, N, N-diisopropylethylamine (DIPEA, 0.6 ml) was added thereto, and stirred at room temperature for 12 hours. Water was added to the reaction and extracted twice with ethyl acetate, and then the organic layer was once washed with brine. The organic layer was dehydrated with anhydrous sodium sulfate and filtered under reduced pressure. The filtrate was concentrated under reduced pressure and purified by high resolution liquid chromatography to give (2E,4E,6E,8E)-N-(2-(2-(2-(((R)-3-(3,4-bis(benzyloxy)phenoxy)-2-hydroxypropyl)amino)ethoxy)ethoxy)ethyl)-3,7-dimethyl-9-(2,6,6-trimethylcyclohex-1-en-1-yl) nona-2,4,6,8-tetraenamide (RTEG-1104, 60 mg, yield: 41%) as a white solid. $^1$H NMR (400 MHZ, DMSO-d$_6$) δ (ppm) 1.01 (s, 6H), 1.53 (m, 2H), 1.74-1.79 (m, 5H), 1.96 (m, 2H), 2.12 (s, 3H), 2.42 (s, 3H), 2.56-2.81 (m, 4H), 3.04 (m, 2H), 3.52-3.54 (m, 6H), 3.67 (m, 2H), 3.95-4.05 (m, 3H), 5.16 (s, 4H), 5.37 (br s, 1H), 5.91 (br s, 1H), 6.22 (s, 2H), 6.51 (s, 4H), 6.57-6.61 (m, 2H), 6.98 (d, 1H), 7.32-7.48 (m, 10H), 8.51 (br s, 1H); ESI-MS Calcd m/z for C$_{49}$H$_{64}$N$_2$O$_7$ [M+H]$^+$ 794.35 Found 793.06.

Example 2: Preparation of (2E, 4E, 6E, 8E)-N-(2-(2-(2-((3,4-bis(benzyloxy) benzyl)amino)ethoxy)ethoxy)ethyl)-3,7-dimethyl-9-(2,6,6-trimethylcyclohex-1-en-1-yl)nona-2,4,6,8-tetraenamide (RTEG-1105)

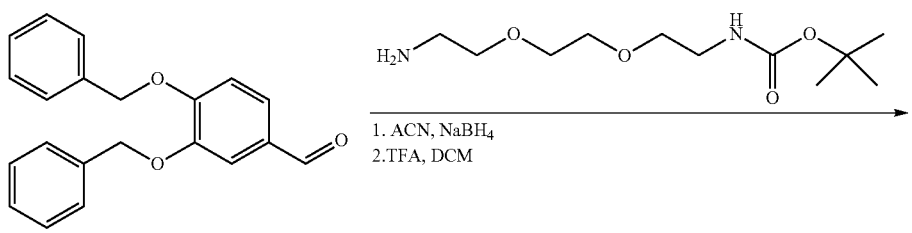

1101

1. ACN, NaBH$_4$
2. TFA, DCM

-continued

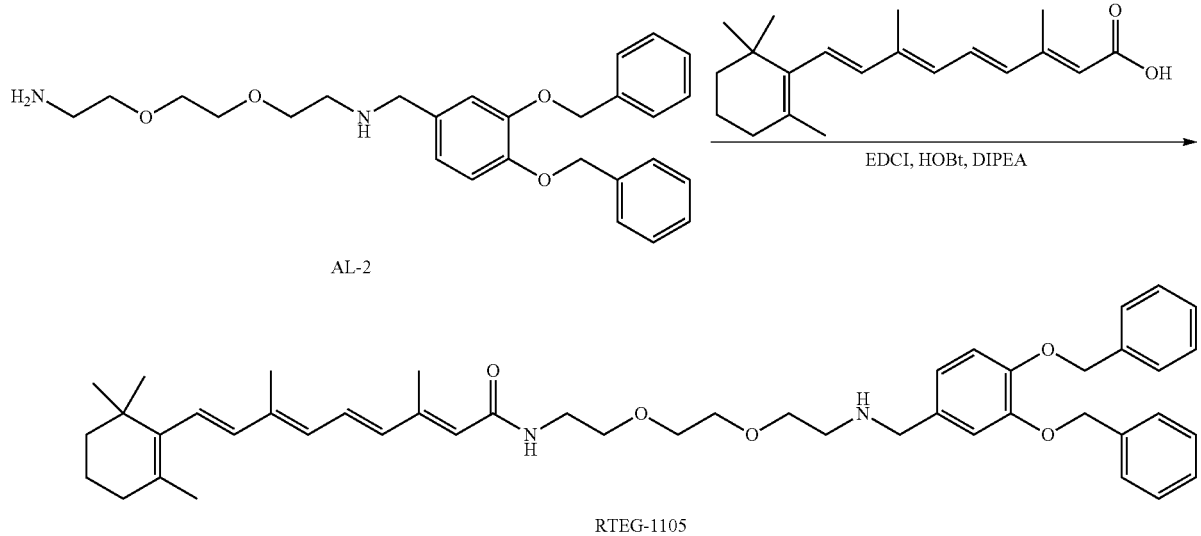

Step 1) Preparation of 2-(2-(2-aminoethoxy) ethoxy)-N-(3,4-bis(benzyloxy)benzyl)ethan-1-amine (AL-2)

3,4-Bis(benzyloxy)benzaldehyde (1101, 0.5 g, 1.57 mmol) was dissolved in acetonitrile (CAN, 10 ml), and then tert-butyl (2-(2-(2-aminoethoxy)ethoxy)ethyl)carbamate (468 mg, 1.88 mmol) was added thereto, and stirred at 60 to 70° C. for 5 hours. After cooling to room temperature, sodium boronhydride (NaBH$_4$, 106 mg, 2.82 mmol) was slowly added to the reaction, and then stirred at room temperature for about 5 hours. Water was added to the reaction solution to complete the reaction, and the compound was extracted with ethyl acetate (50 mL×3). The extracted organic solvent layer was washed with brine and dehydrated using sodium sulfate. The filtered solvent was concentrated, and when again dissolved in dichloromethane (6 ml). Trifluoroacetic acid (TFA, 2 ml) was then added t-hereto and stirred at room temperature for 2 hours, and the solvent was concentrated under reduced pressure. The concentrate was purified by column chromatography (methyl-ene chloride/methanol=15:1) to gave 2 (2-(2-aminoethoxy) ethoxy)-N-(3,4-bis(benzyloxy)benzyl)ethan-1-amine (AL-2, 590 mg, yield: 84%) as a pale yellow liquid $^1$H NMR (400 MHz, DMSO-d$_6$) δ (ppm) 2.59 (t, 2H), 3.32-3.61 (m, 12H), 4.62 (br s, 1H), 5.10 (s, 4H), 6.82 (d, 1H), 6.97 (d, 1H, 7.06 (s, 1H), 7.30-7.46 (m, 10H).

Step 2) (2E,4E,6E,8E)-N-(2-(2-(2-((3,4-bis(benzyloxy) benzyl)amino)ethoxy)ethoxy)ethyl)-3,7-dimethyl-9-(2,6,6-trimethylcyclohex-1-en-1-yl)nona-2,4,6,8-tetraenamide (RTEG-1105) was synthesized in a similar manner to step 5 of Example 1. $^1$H NMR (400 MHz, DMSO-d$_6$) δ (ppm) 1.01 (s, 6H), 1.54 (m, 2H), 1.75-1.80 (m, 5H), 1.98 (m, 2H), 2.12 (s, 3H), 2.42 (s, 3H), 2.72 (t, 2H), 3.04 (t, 2H), 3.51-3.54 (m, 6H), 3.67 (t, 2H), 3.76 (s, 2H), 5.14 (s, 4H), 6.22 (m, 2H), 6.37 (br s, 1H), 6.51 (s, 4H), 6.80 (d, 1H), 6.87 (d, 1H), 6.99 (s, 1H), 7.31-7.46 (m, 10H), 8.41 (br s, 1H); ESI-MS Calcd m/z for C$_{47}$H$_{60}$N$_2$O [M+H]+ 734.3 Found 733.01.

Example 3: Preparation of (R)—N-(15-(3,4-bis (benzyloxy)phenoxy)-14-hydroxy-3,6,9-trioxa-12-azapentadecyl)-4-phenylbutaneamide (PBA-1104)

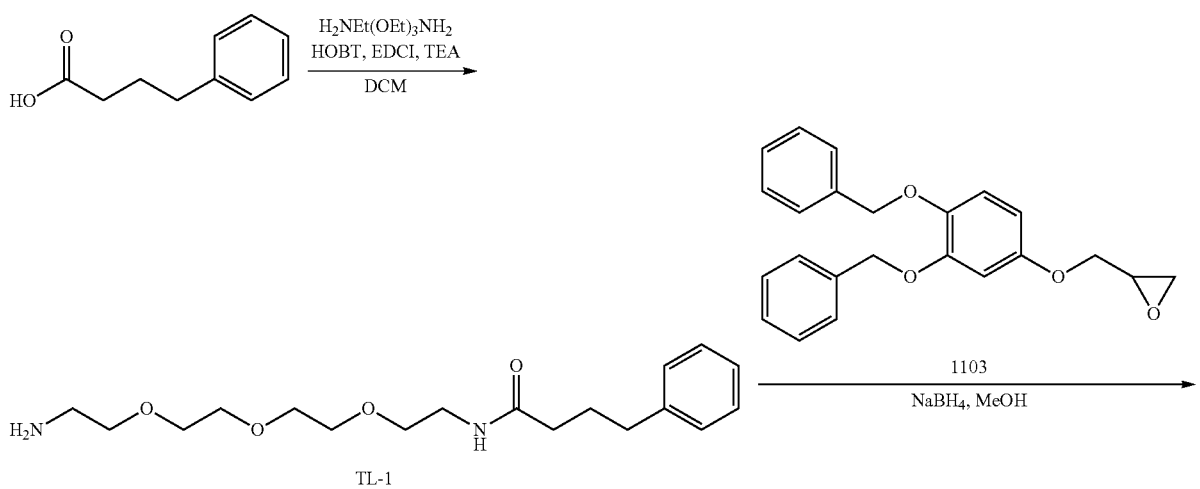

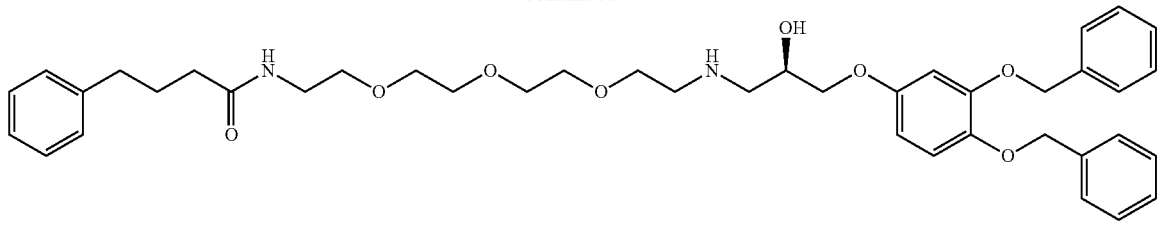

RTEG-1104

Step 1) 2,2'-(2,2'-oxybis(ethane-2,1-diyl)bis (oxy))diethanamine (21 g, 73.1 mmol) was dissolved in dichloromethane (400 ml), and then hydroxybenzotriazole (HOBt, 12.3 g, 91.5 mmol) and 1-ethyl-3-(3-dimethylaminopropyl) carbodiimide (EDCI, 17.6 g, 91.5 mmol) was added sequentially. Triethylamine ($Et_3N$, 18.5 g, 180 mmol) was added thereto and cooled to 0° C. 4-Phenylbutyric acid (15 g, 91.5 mmol) was dissolved in dichloromethane (200 ml) and then added to the reaction, followed by stirring at room temperature for 12 hours. The reaction mixture was diluted with water, and then extracted with dichloromethane (50 ml*3 times), the organic layer is dehydrated with anhydrous sodium sulfate and filtered. The filtrate was concentrated under reduced pressure, and then purified by silica gel column chromatography to give N-(2-(2-(2-(2-aminoethoxy) ethoxy) ethoxy) ethyl)-4-phenylbutanamide (TL-1, 12 g) as a yellow liquid. ESIMS m/z: 339.1 $[M+H]^+$.

Step 2) N-(2-(2-(2-(2-aminoethoxy) ethoxy) ethoxy) ethyl)-4-phenylbutanamide (TL-1, 100 mg, 0.295 mmol) was dissolved in methanol (6 ml), and then R-2-((3,4-bis(benzyloxy)phenoxy)methyl)oxirane (1103, 128 mg, 0.354 mmol) was added thereto, and stirred at 50° C. for 10 hours. The reaction mixture was concentrated under reduced pressure and purified by silica gel column chromatography to give (R)—N-(15-(3,4-bis(benzyloxy) phenoxy)-14-hydroxy-3,6,9-trioxa-12-azapentadecyl)-4-phenylbutanamide (PBA-1104, 2013 mg, yield: 50%) as a white solid. $^1$H NMR (400 MHZ, DMSO-$d_6$) δ (ppm) 1.25 (s, 1H), 1.92 (m, 2H), 2.31 (t, 2H), 2.56-2.81 (m, 4H), 3.28 (m, 2H), 3.51-3.53 (m, 10H), 3.67 (t, 2H), 3.95-4.20 (m, 3H), 5.14 (s, 4H), 5.37 (br s, 1H), 5.90 (br s, 1H), 6.57 (s, 1H), 6.67 (d, 1H), 6.96 (d, 1H), 7.16 (m, 3H), 7.30 (mk 8H), 7.45 (m, 4H); ESI-MS Calcd m/z for $C_{41}H_{52}N_2O_8$ $[M+H]^+$ 701.5 Found 700.87.

Example 4: Preparation of N-(1-(3,4-bis(benzyloxy) phenyl)-5,8,11-trioxa-2-azatridecan-13-yl)-4-phenylbutanamide (PBA-1105)

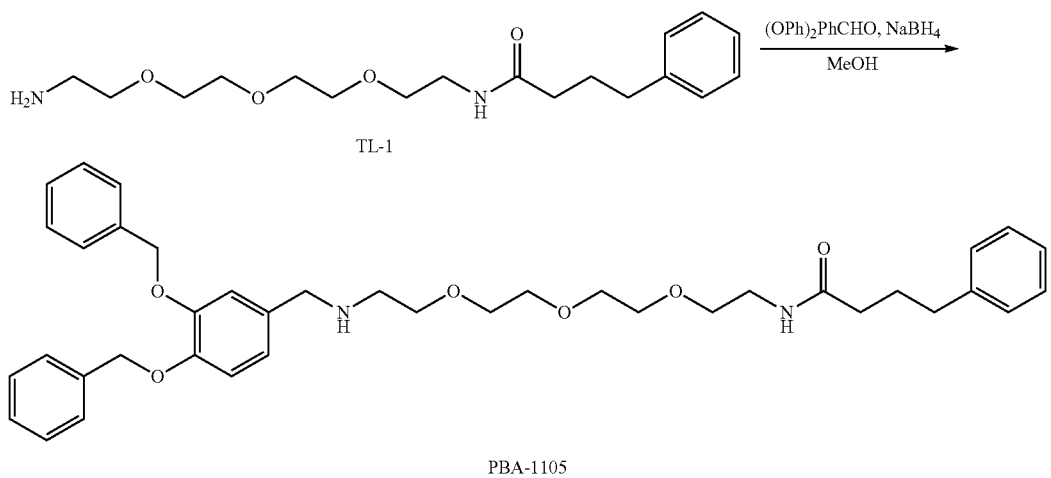

PBA-1105

Step 1) Preparation of N-(1-(3,4-bis(benzyloxy) phenyl)-5,8,11-trioxa-2-azatridecan-13-yl)-4-phenylbutanamide (PBA-1105)

N-(2-(2-(2-(2-aminoethoxy) ethoxy) ethoxy) ethyl)-4-phenylbutanamide (TL-1) (10 g, 29.6 mmol) was dissolved in methanol (MeOH, 150 mL), and then 3,4-dihydroxybenzaldehyde (10.3 g, 32.3 mmol) was added thereto. Thereafter, the mixture was stirred at 65° C. for about 5 hours. After cooling to room temperature, sodium borohydride ($NaBH_4$, 2.2 g, 57.9 mmol) was added and stirred at room temperature for about 5 hours. Water was added to the reaction solution to complete the reaction, and the compound was extracted with ethyl acetate (50 mL×3). The extracted organic solvent layer was washed with brine and water was removed using sodium sulfate. The filtered solvent was concentrated and then purified by column chromatography using silica gel (methylene chloride/methanol=15:1). Thereby, N-(1-(3,4-bis(benzyloxy)phenyl)-5,8,11-trioxa-2-azatridecan-13-yl)-4-phenylbutanamide (PBA-1105) (10.3 g) as a yellow liquid) was obtained. $^1$H NMR ($CDCl_3$, 400 MHZ) δ (ppm) 7.45-7.42 (m, 4H), 7.36-7.29 (m, 7H), 7.27-7.26 (m, 1H), 7.18-7.15 (m, 3H), 6.99 (d, 1H), 6.83 (d, 1H), 6.41 (brs, 1H), 5.15 (d, 4H), 3.71 (s, 2H), 3.60-3.55 (m, 10H), 3.55-3.49 (m, 2H), 3.42-3.39 (m, 2H), 2.75-2.73 (m, 2H), 2.65-2.61 (m, 2H), 2.18-2.15 (m, 2H), 1.97-1.93 (m, 2H), 1.25 (brs, 1H); ESI-MS Calcd m/z for $C_{39}H_{48}N_2O_6$ $[M+H]^+$ 641.00 Found 640.82.
Example 5: Preparation of 3-(3-(benzo[d][1,3]di-oxol-5-yl)-1H-pyrazol-5-yl)-N-(2-(2-(2-((3-((4-fluo-robenzyl)oxy)) benzyl)amino)ethoxy)ethoxy)ethyl) aniline (Anle138b-F105)
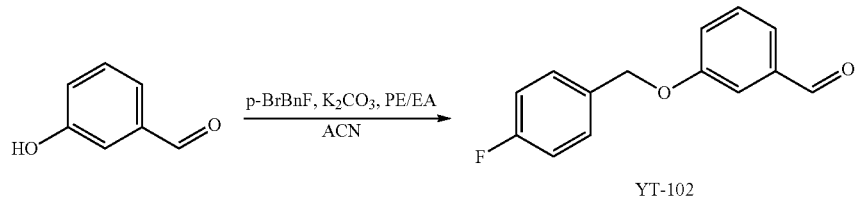
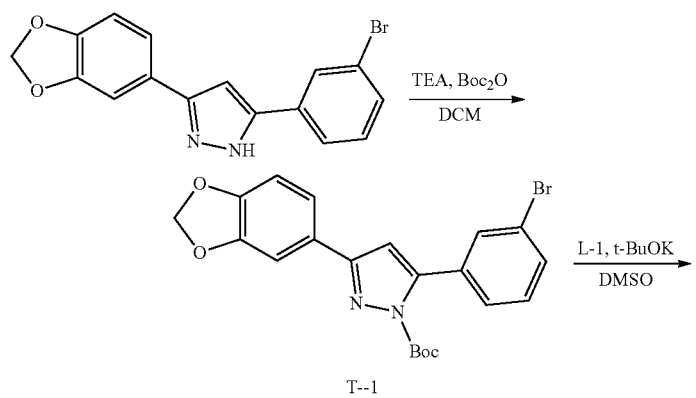
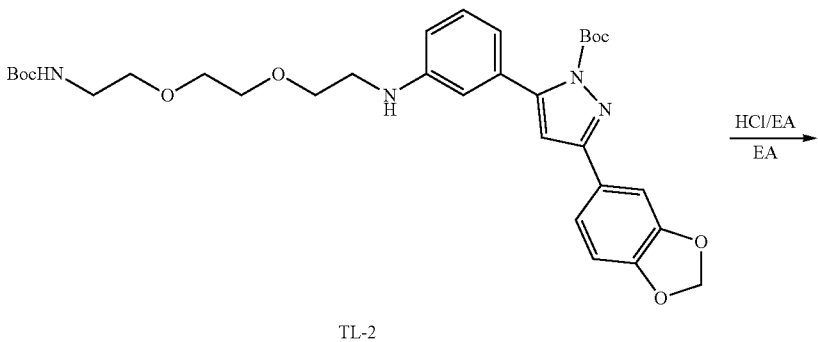
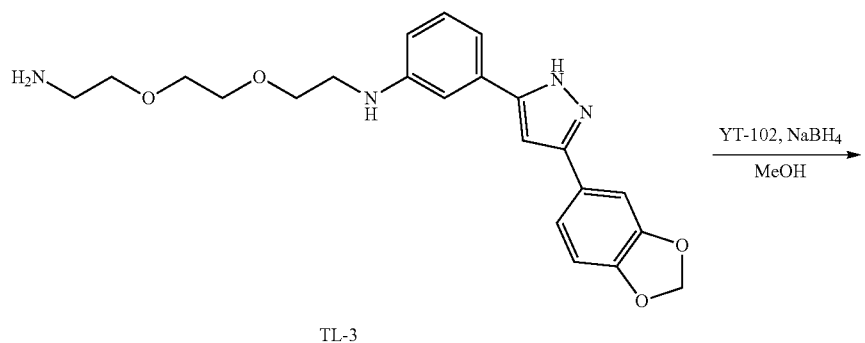

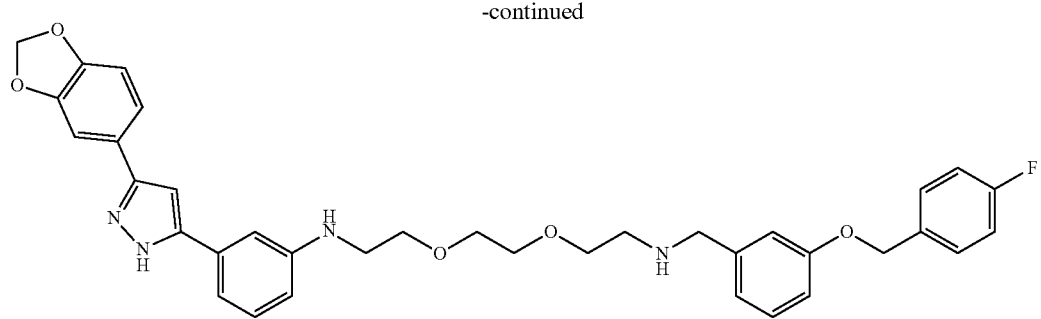

Anle 138b-F105

Step 1) Preparation of 3-((4-fluorobenzyl)oxy)benzaldehyde (YT-102)

Potassium carbonate ($K_2CO_3$, 112.5 g, 0.81 mol) and 1-(bromomethyl)-4-fluorobenzene (95 g, 0.50 mol) were added to a solution of 3-hydroxybenzaldehyde (50 g, 0.41 mol) in acetonitrile (ACN, 500 mL). The mixture was stirred at 60° C. for about 10 hours. After the reaction was completed, the reaction solution was filtered and concentrated. Petroleum ether/ethyl acetate (PE/EA, 20:1, 20 mL) was added thereto, and further stirred for about 1 hour, and then concentrated through a filter. Thereby, 3-((4-fluorobenzyl)oxy)benzaldehyde (YT-102, 25 g) was obtained as a greyish white solid. $^1$H NMR (DMSO-$d_6$, 400 MHZ) δ (ppm) 9.98 (s, 1H), 7.54-7.50 (m, 5H), 7.36 (m, 1H), 7.23 (m, 2H), 5.18 (s, 2H)

Step 2) Preparation of tert-butyl 3-(benzo[d][1,3]dioxol-5-yl)-5-(3-bromophenyl)-1H-pyrazole-1-carboxylate (T-1)

3-(Benzo[d][1,3]dioxol-5-yl)-5-(3-bromophenyl)-1H-pyrazole (200 mg, 0.58 mmol) was dissolved in methylene chloride (DCM, 4 mL), and then triethylamine (TEA, 88 mg, 0.87 mmol) and di-tert-butyl dicarbonate ($Boc_2O$, 153 mg, 0.70 mmol) were added. The mixture was stirred at room temperature for about 4 hours. After the reaction was completed, the filtered solution was concentrated and purified by column chromatography using silica gel (ethyl acetate/petroleum ether=1:15 to 1:5). Thereby, tert-butyl 3-(benzo[d][1,3]dioxol-5-yl)-5-(3-bromophenyl)-1H-pyrazole-1-carboxylate (T-1, 200 mg) was obtained as a white solid. $^1$H NMR (DMSO-$d_6$, 400 MHz) δ (ppm) 8.09-7.43 (m, 5H), 7.11-6.94 (m, 3H), 6.08 (s, 2H), 1.34 (d, J=20 Hz, 9H)

Step 3) Preparation of tert-butyl 3-(benzo[d][1,3]dioxol-5-yl)-5-(3-((2,2-dimethyl-4-oxo-3,8,11-trioxa-5-azatridecane-13-yl)amino)phenyl)-1H-pyrazole-1-carboxylate (TL-2)

Tert-butyl 3-(benzo[d][1,3]dioxol-5-yl)-5-(3-bromophenyl)-1H-pyrazole-1-carboxylate (T-1, 200 mg, 0.45 mmol) was dissolved in dimethylsulfoxide (DMSO, 4 mL), and then tert-butyl (2-(2-(2-aminoethoxy)ethoxy)ethyl)carbamate (L-1, 168 mg, 0.68 mmol) and potassium tert-butoxide (t-BuOK, 101 mg, 0.90 mmol) were added thereto. The mixture was stirred at 120° C. for about 16 hours. The reacted compound was filtered and concentrated, and then purified by preparative high performance liquid chromatography (Prep-HPLC). Thereby, tert-butyl 3-(benzo[d][1,3]dioxol-5-yl)-5-(3-((2,2-dimethyl-4-oxo-3,8,11-trioxa-5-azatridecane-13-yl)amino)phenyl)-1H-pyrazole-1-carboxylate (TL-2, 180 mg) was obtained as a pale yellow solid.

Step 4) Preparation of N-(2-(2-(2-aminoethoxy)ethoxy)ethyl)-3-(3-(benzo[d][1,3]dioxol-5-yl)-1H-pyrazol-5-yl)aniline (TL-3)

Tert-butyl 3-(benzo[d][1,3]dioxol-5-yl)-5-(3-((2,2-dimethyl-4-oxo-3,8,11-trioxa-5-azatridecane-13-yl)amino)phenyl)-1H-pyrazole-1-carboxylate (TL-2, 180 mg, 0.29 mmol) was dissolved in ethyl acetate (EA, 4 mL), and then hydrochloric acid/ethyl acetate (1 mL, 3N) solution was added thereto. The mixture was stirred at room temperature for about 2 hours. The reacted compound was filtered and concentrated. Thereby, N-(2-(2-(2-aminoethoxy)ethoxy)ethyl)-3-(3-(benzo[d][1,3]dioxol-5-yl)-1H-pyrazol-5-yl)aniline (TL-3, 100 mg) was obtained as a white solid.

Step 5) Preparation of 3-(3-(benzo[d][1,3]dioxol-5-yl)-1H-pyrazol-5-yl)-N-(2-(2-(2-((3-((4-fluorobenzyl)oxy)) benzyl)amino)ethoxy)ethoxy)ethyl)aniline (Anle138b-F105)

N-(2-(2-(2-aminoethoxy)ethoxy)ethyl)-3-(3-(benzo[d][1,3]dioxol-5-yl)-1H-pyrazol-5-yl)aniline (TL-3, 90 mg, 0.22 mmol) was dissolved in methanol (MeOH, 2 mL), and then 3-((4-fluorobenzyl)oxy)benzaldehyde (YT-102, 50 mg, 0.22 mmol) was added and stirred at 65° C. Then, sodium borohydride ($NaBH_4$, 16 mg, 0.44 mmol) was added thereto at 5° C. and further stirred for about 1 hour. The reacted compound was concentrated and purified by preparative high performance liquid chromatography (Prep-HPLC). Thereby, 3-(3-(benzo[d][1,3]dioxol-5-yl)-1H-pyrazol-5-yl)-N-(2-(2-(2-((3-((4-fluorobenzyl)oxy))benzyl)amino)ethoxy)ethoxy)ethyl)aniline (Anle138b-F105, 15 mg) was obtained as a colorless liquid. $^1$H NMR (DMSO-$d_6$, 400 MHz) δ (ppm) 13.08 (brs, 1H), 7.47 (q, J=6 Hz, 2H), 7.37-7.31 (m, 2H), 7.21-7.17 (m, 3H), 7.11 (t, J=8 Hz, 1H), 7.00-6.96 (m, 5H), 6.88-6.82 (m, 2H), 6.56 (d, J=8 Hz, 1H), 6.04 (s, 2H), 5.59 (brs, 1H), 5.04 (s, 2H), 3.66 (s, 2H), 3.60-3.52 (m, 6H), 3.47 (t, J=6 Hz, 2H), 3.26-3.22 (m, 2H), 2.61 (t, J=5.6 Hz, 2H); ESI-MS Calcd m/z for $C_{36}H_{37}FN_4O_5$ $[M+H]^+$ 625.10 Found 624.71.

Example 6: Preparation of (3R, 4S, 5S, 6R)-5-methoxy-4-((2R,3R)-2-methyl-3-(3-methylbut-2-en-1-yl)oxirane-2-yl)-1-oxaspiro[2.5]octan-6-yl(13E,15E,17E,19E)-1-(3-(benzyloxy)phenyl)-12-oxo-5,8-dioxa-2,11-diazahenicosa-13,15,17,19-tetraene-21-oate (Fumagillin-105)

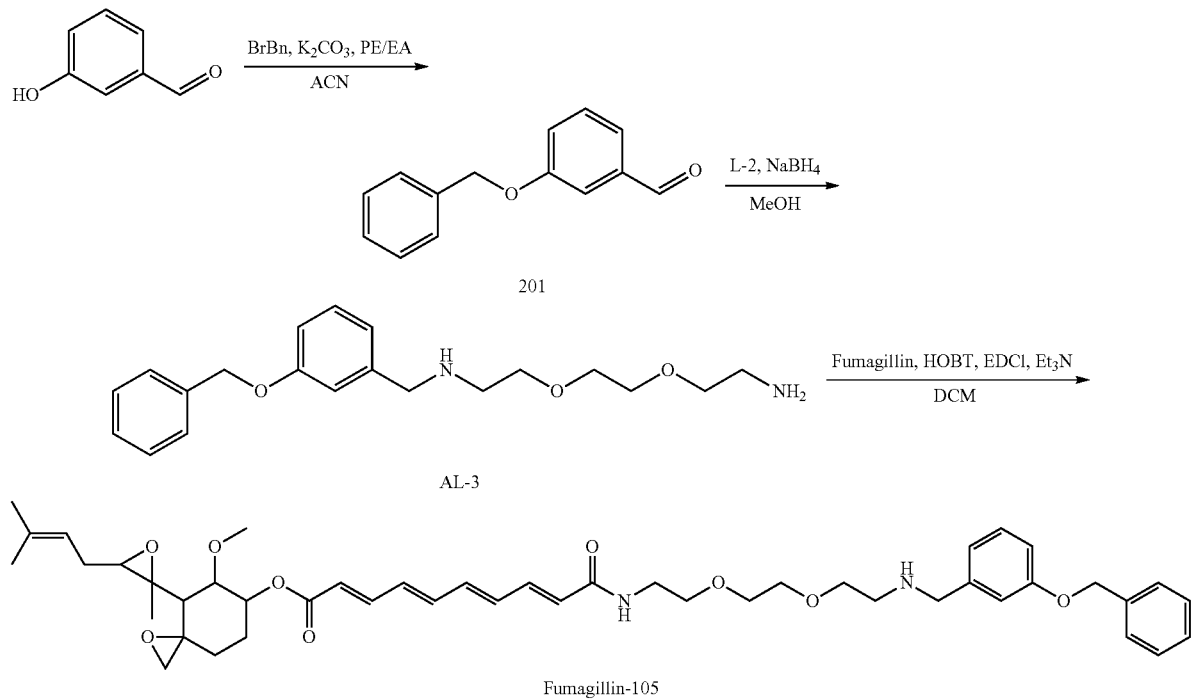

Step 1) Preparation of 3-(benzyloxy)benzaldehyde (201)

Potassium carbonate ($K_2CO_3$, 112.5 g, 0.81 mol) and bromomethylbenzene (85 g, 0.50 mol) were added to a solution of 3-hydroxybenzaldehyde (50 g, 0.41 mol) in acetonitrile (ACN, 500 mL). The mixture was stirred at 60° C. for about 10 hours. After the reaction was completed, the reaction solution was filtered and then concentrated. Then, petroleum ether/ethyl acetate (PE/EA, 20:1, 20 mL) was added thereto, and further stirred for about 1 hour, followed by concentration through a filter. Thereby, 3-(benzyloxy) benzaldehyde (201, 25 g) was obtained as a grayish white solid. $^1$H NMR (DMSO-$d_6$, 400 MHz) δ (ppm) 9.97 (s, 1H), 7.54-7.51 (m, 3H), 7.47 (d, J=7.2 Hz, 2H), 7.42-7.34 (m, 4H), 5.19 (s, 2H)

Step 2) Preparation of 2-(2-(2-aminoethoxy)ethoxy)-N-(3-(benzyloxy)benzyl)ethan-1-amine (AL-3)

3-(Benzyloxy)benzaldehyde (201, 50 g, 235.8 mmol) was dissolved in methanol (MeOH, 500 mL), and then 2,2'-(ethane-1,2-diylbis(oxy))diethanamine (L-2, 34.9 g, 235.8 mmol) was added thereto. The mixture was stirred at 65° C. for about 6 hours. After cooling to room temperature, sodium borohydride (NaBH$_4$, 8.95 g, 235.8 mmol) was added and stirred at 50° C. overnight. Water was added to compete the reaction, and the compound was extracted with ethyl acetate (EtOAc, 50 mL×3). The extracted organic solvent layer was washed with brine, and water was removed by adding sodium sulfate ($Na_2SO_4$). The solution was concentrated and then purified by column chromatography using silica gel (methylene chloride/methanol=12:1). Thereby, 2-(2-(2-aminoethoxy)ethoxy)-N-(3-(benzyloxy)benzyl)ethan-1-amine (AL-3, 20 g) was obtained as a yellow liquid. $^1$H NMR (DMSO+$D_2O$, 400 MHz) δ (ppm) 7.41-7.29 (m, 5H), 7.18 (t, J=8 Hz, 1H), 6.94 (s, 1H), 6.86-6.81 (m, 2H), 5.03 (s, 2H), 3.60 (s, 2H), 3.45-3.42 (m, 6H), 3.33 (t, J=5.6 Hz, 2H), 2.57-2.52 (m, 4H); ESI-MS Calcd m/z for $C_{20}H_{28}N_2O_3$ [M+H]$^+$ 345.10 Found 344.46.

Step 3) Preparation of (3R,4S,5S,6R)-5-methoxy-4-((2R,3R)-2-methyl-3-(3-methylbut-2-en-1-yl)oxirane-2-yl)-1-oxaspiro[2.5]octan-6-yl(13E,15E,17E,19E)-1-(3-(benzyloxy)phenyl)-12-oxo-5,8-dioxa-2,11-diazahenicosa-13,15,17,19-tetraene-21-oate (Fumagillin-105)

2-(2-(2-Aminoethoxy)ethoxy)-N-(3-(benzyloxy)benzyl)ethan-1-amine (AL-3, 70 mg, 0.22 mmol) was dissolved in methylene chloride (DCM, 2 mL), and then fumagillin (100 mg, 0.22 mmol), hydroxy benzotriazole (HOBT, 34 mg, 0.25) mmol), 1-ethyl-3-(3-dimethylaminopropyl)carbodiimide (EDCI, 48 mg, 0.25 mmol) and triethylamine (Et$_3$N, 44 mg, 0.44 mmol) were added thereto. The mixture was stirred at 30° C. for about 10 hours. After the reaction was completed, the compound was extracted with methylene chloride (DCM, 50 mL×3). The extracted organic solvent layer was washed with brine, and water was removed using sodium sulfate. The filtered solvent was concentrated and then purified by preparative high performance liquid chromatography (Prep-HPLC). Thereby (3R,4S,5S,6R)-5-methoxy-4-((2R,3R)-2-methyl-3-(3-methylbut-2-en-1-yl)oxirane-2-yl)-1-oxaspiro[2.5]octan-6-yl(13E,15E,17E,19E)-1-(3-

(benzyloxy)phenyl)-12-oxo-5,8-dioxa-2,11-diazahenicosa-13,15,17,19-tetraene-21-oate (Fumagillin-105, 3 mg) was obtained as a yellow solid. ESI-MS Calcd m/z for $C_{46}H_{60}N_2O_9$ [M]$^+$ 784.90 Found 784.99.
Example 7: Preparation of 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione (Vinclozolin-2204)
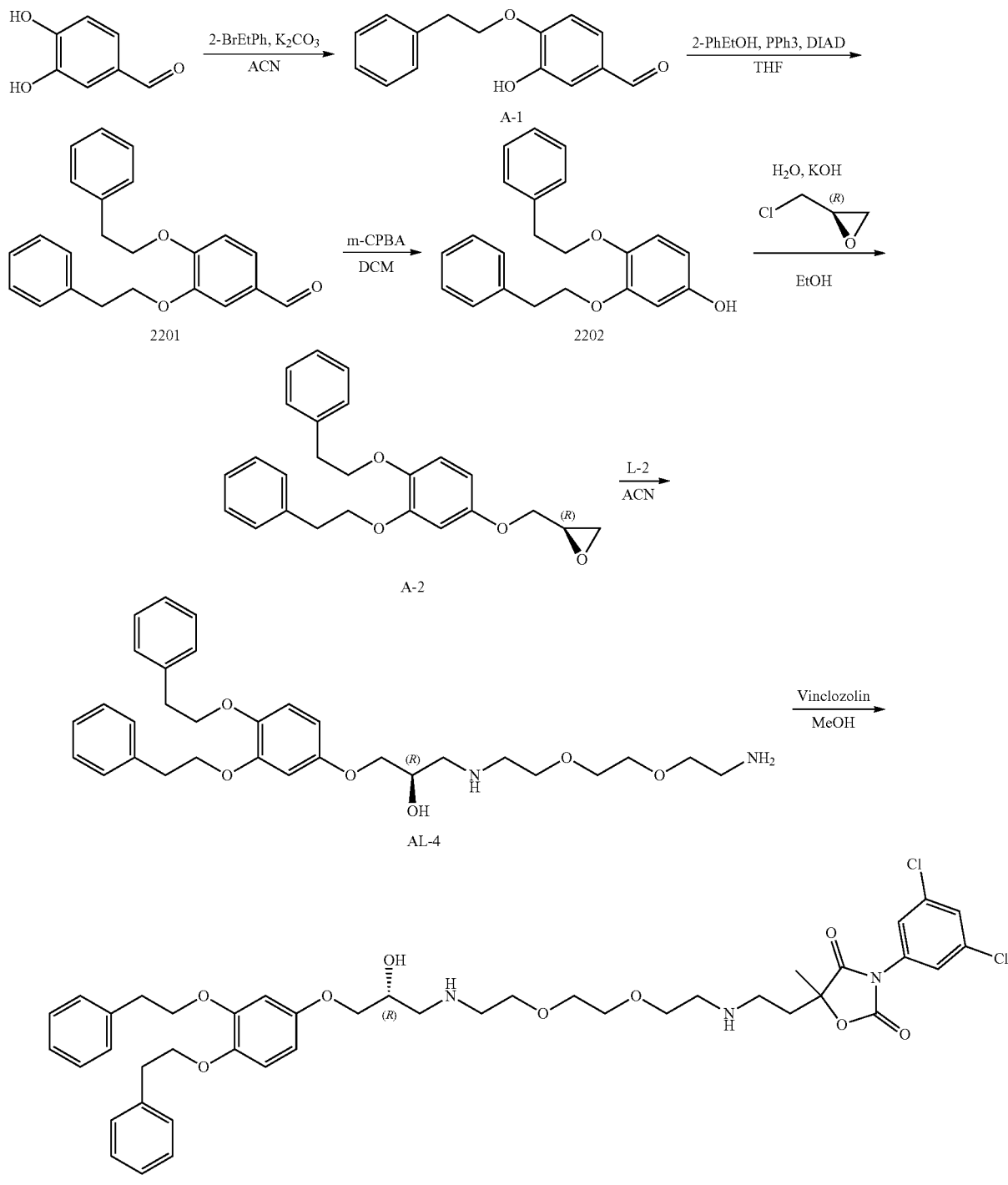
Vinclozolin-2204

Step 1) Preparation of 3-hydroxy-4-phenethoxybenzaldehyde (A-1)

3,4-Dihydroxybenzaldehyde (200 g, 1.4 mol) was dissolved in acetonitrile (ACN, 2 L), and then potassium carbonate ($K_2CO_3$, 260 g, 1.9 mol) and 1-(2-bromoethyl)benzene (267 g, 1.4 mol) were added thereto. The mixture was stirred at 80° C. for about 16 hours. After the reaction was completed using hydrochloric acid (1.5 L, 1N), the compound was extracted with ethyl acetate (EA, 1 L×3). The extracted organic solvent layer was washed with brine, water was removed with sodium sulfate and then filtered. The concentrated solution was purified by column chromatography using silica gel (ethyl acetate/petroleum ether=20:1 to 10:1). Thereby, 3-hydroxy-4-phenethoxybenzaldehyde (A-1, 320 g) was obtained as a while solid. ESI-MS Calcd m/z for $C_{15}H_{14}O_3[M+H]^+$ 243.0 Found 242.27.

Step 2) Preparation of 3,4-diphenethoxybenzaldehyde (2201)

3-Hydroxy-4-phenethoxybenzaldehyde (A-1, 320 g, 1.32 mol) was dissolved in tetrahydrofuran (THF, 5 L), and then, 2-phenylethanol (193.5 g, 1.59 mol), triphenylphosphine ($PPh_3$, 520 g, 1.98 mol) and diisopropyl azodicarboxylate (DIAD, 400 g, 1.98 mol) were added thereto. The mixture was stirred at 65° C. for about 16 hours. Water (100 mL) was added to the reaction solution to complete the reaction, and extracted with ethyl acetate (100 mL×2). Sodium sulfate was added to the extracted organic solvent layer to remove water, filtered and then concentrated. The concentrated compound was purified by column chromatography using silica gel (ethyl acetate/petroleum ether=1:15 to 1:10). Thereby, 3,4-diphenenthoxybenzaldehyde (2201, 160 g) was obtained as a white solid. $^1$H NMR (DMSO-$d_6$, 400 MHz) (ppm) 9.81 (s, 1H), 7.51 (dd, J=8 Hz and 1.6 Hz, 1H), 7.40-7.17 (m, 12H), 4.27 (t, J=6.8 Hz, 2H), 4.22 (t, J=6.8 Hz, 2H), 3.06 (q, J=6.4 Hz, 4H); ESI-MS Calcd m/z for $C_{23}H_{22}O_3[M+H]^+$ 346.90 Found 346.43.

Step 3) Preparation of 3,4-diphenethoxyphenol (2202)

3,4-Diphenethoxybenzaldehyde (2201, 160 g, 0.46 mmol) was dissolved in methylene chloride (DCM, 2 L), and then meta-chloroperoxybenzoic acid (m-CPBA, 119 g, 069 mmol) was added thereto. The mixture was stirred at room temperature for about 16 hours. When the reaction was completed, the solution was filtered and then concentrated. The concentrated solution was purified by column chromatography using silica gel (ethyl acetate/petroleum ether=1:15 to 1:5). Thereby, 3,4-diphenoxyphenol (2202, 100 g) was obtained as a grayish white solid. ESI-MS Calcd m/z for $C_{22}H_{22}O_3[M+H]^+$ 335.00 Found 334.42.

Step 4) Preparation of (R)-2-((3,4-diphenethoxyphenoxy)methyl)oxirane (A-2)

3,4-Diphenethoxyphenol (2202) (5 g, 15 mmol) was dissolved in ethanol (EtOH, 50 mL), and then water (2.5 mL) and potassium hydroxide (KOH, 1.93 g, 34.5 mmol) were added thereto. Then, (R)-2-(chloromethyl)oxirane (8 g, 87 mmol) was added and stirred at room temperature for about 16 hours. Water (50 mL) was added to the reaction solution to complete the reaction, and the compound was extracted with ethyl acetate (EA, 20 mL×3). The extracted organic solvent was washed with brine, water was removed with sodium sulfate, filtered and concentrated. The concentrated compound was purified by column chromatography using silica gel (ethyl acetate/petroleum ether=1:15 to 1:10). Thereby, (R)-2-((3,4-diphenethoxyphenoxy)methyl)oxirane (A-2, 2.5 g) was obtained as a white solid. ESI-MS Calcd m/z for $C_{25}H_{26}O_4[M+H]^+$ 391.00 Found 390.48.

Step 5) Preparation of (R)-1-((2-(2-(2-aminoethoxy)ethoxy)ethyl)amino)-3-(3,4-diphenethoxyphenoxy)propan-2-ol (AL-4)

(R)-2-((3,4-diphenethoxyphenoxy)methyl)oxirane (A-2, 20 g, 51.2 mmol) was dissolved in acetonitrile (ACN, 200 mL), and then 2-(2-(2-aminoethoxy)ethoxy)ethanamine (L-2, 15.2 g, 102.5 mmol) was added thereto. The mixture was stirred at 70° C. for about 40 hours. When the reaction was completed, the reaction solution was filtered and concentrated. The concentrated solution was purified by column chromatography using silica gel (methylene chloride/methanol=100:1 to 30:1). Thereby, (R)-1-((2-(2-(2-aminoethoxy)ethoxy)ethyl)amino)-3-(3,4-diphenethoxyphenoxy)propan-2-ol (AL-4, 12 g) was obtained as a yellow liquid. $^1$H NMR (CD$_3$OD, 400 MHz) δ (ppm) 8.52 (s, 3H), 7.30-7.20 (m, 10H), 6.85 (d, J=8 Hz, 1H), 6.60 (d, J=2.8 Hz, 1H), 6.47 (dd, J=8 Hz and 2 Hz, 1H), 4.16 (t, J=6.8 Hz, 3H), 4.08 (t, J=6.8 Hz, 2H), 3.96 (q, J=4 Hz, 2H), 3.79 (t, J=5.2 Hz, 2H), 3.70 (m, 7H), 3.32-3.25 (m, 3H), 3.17-2.98 (m, 8H); ESI-MS Calcd m/z for $C_{31}H_{42}N_2O_6 [M+H]^+$ 539.20 Found 538.69.

Step 6) Preparation of liquid 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione (Vinclozolin-2204)

(R)-1-((2-(2-(2-aminoethoxy)ethoxy)ethyl)amino)-3-(3,4-diphenethoxyphenoxy)propan-2-ol (AL-4, 120 mg, 0.22 mmol) was dissolved in methanol (MeOH, 2 mL), and then vinclozolin (117 mg, 0.33 mmol) was added thereto. The mixture was stirred at 65° C. for about 16 hours. When the reaction was completed, the solution was filtered and concentrated. The concentrated solution was purified by preparative high performance liquid chromatography (Prep-RPLC) Thereby, 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione (Vinclozolin-2204, 15 mg) was obtained as a colorless liquid. $^1$H NMR (DMSO-$d_6$, 400 MHz) δ (ppm) 1.65 (m, 3H), 2.65 (m, 4H), 2.97 (m, 4H), 3.17 (m, 2H), 3.42 (m, 8H), 3.57 (d, J=8 Hz, 1H), 3.80 (m, 3H), 4.02 (t, J=8 Hz, 2H), 4.13 (t, J=8 Hz, 2H), 4.90 (b, 1H), 5.33 (m, 2H), 6.20 (m, 1H), 6.38 (d, J=8 Hz, 1H), 6.54 (m, 1H), 6.82 (d, J=8 Hz, 1H), 7.25 (m, 11H), 7.49 (d, J=1 Hz, 1H), 7.76 (s, 1H), 9.70 (s, 1H); ESI-MS Calcd m/z for $C_{43}H_{51}Cl_2N_3O_9 [M+H]^+$ 825.00 Found 824.79.

Example 8: Preparation of (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol (PHTPP-1304)
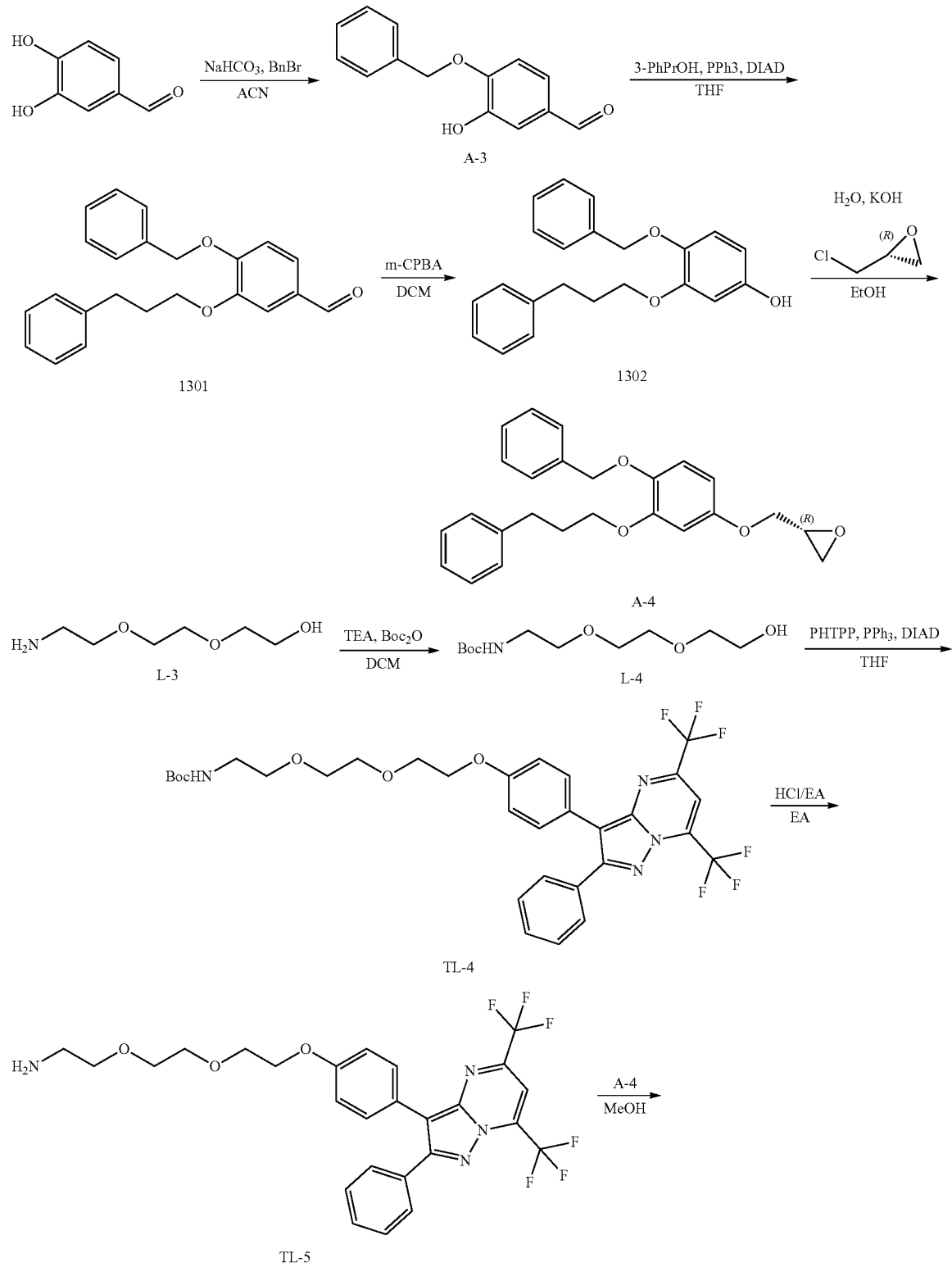

-continued

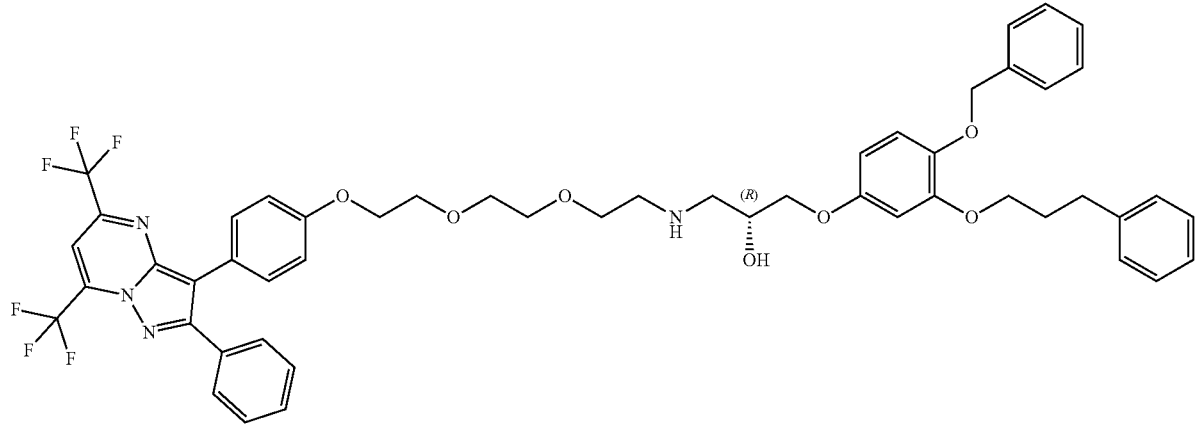

PHTPP-1304

Step 1) Preparation of 4-(benzyloxy)-3-hydroxybenzaldehyde (A-3)

3,4-Dihydroxybenzaldehyde (500 g, 3.62 mol) was dissolved in acetonitrile (ACN, 7 L), and then sodium bicarbonate (NaCHO$_3$, 395 g, 4.71 mol) and benzylbromide (BnBr, 619 g, 3.62 mol) were added thereto. The mixture was stirred at 80° C. for about 16 hours. The reaction was completed using hydrochloric acid (3 L, 1N), and the compound was extracted with ethyl acetate (3 L×3). The extracted organic with brine, and the solvent layer was washed remaining water was removed with sodium sulfate, filtered to remove impurities and concentrated. The concentrated solution was purified by column chromatography using silica gel (EA/PE=20:1 to 10:1). Thereby, 4-(benzyloxy)-3-hydroxybenzaldehyde (A-3, 250 g) was obtained as a white solid. $^1$H NMR (DMSO-d$_6$, 400 MHZ) δ (ppm) 9.76 (s, 1H), 9.65 (s, 1H), 7.49 (d, J=6.8 Hz, 2H), 7.42-7.34 (m, 4H), 7.29 (d, J=2 Hz, 1H), 7.19 (d, J=8 Hz, 1H), 5.23 (s, 2H)

Step 2) Preparation of 4-(benzyloxy)-3-(3-phenylpropoxy) benzaldehyde (1301)

4-(Benzyloxy)-3-hydroxybenzaldehyde (A-3, 120 g, 526 mmol) was dissolved in tetrahydrofuran (THF, 2 L), and then 3-phenylpropan-1-ol (85.9 g, 631 mmol), 789 triphenylphosphine (PPh$_3$, 206.9 g, mmol) and diisopropyl azodicarboxylate (DIAD, 159.5 g, 789 mmol) were added thereto. The mixture was stirred at 65° C. for about 16 hours. When the reaction was completed, the reaction mixture was filtered and concentrated. The concentrated solution was purified by column chromatography using silica gel (ethyl acetate/petroleum ether=1:15 to 1:10). Thereby, 4-(benzyloxy)-3-(3-phenylpropoxy)benzaldehyde (1301, 100 g) was obtained as a white solid. $^1$H NMR (DMSO-d$_6$, 400 MHz) δ (ppm) 9.82 (s, 1H), 7.55-7.50 (m, 3H), 7.38 (t, J=7.2 Hz, 3H), 7.36-7.34 (m, 1H), 7.29-7.25 (m, 3H), 7.21-7.16 (m, 3H), 5.26 (s, 2H), 4.04 (t, J=6.4 Hz, 2H), 2.76 (t, J=8 Hz, 2H), 2.04 (t, J=7.2 Hz, 2H)

Step 3) Preparation of 4-(benzyloxy)-3-(3-phenylpropoxy)phenol (1302)

4-(Benzyloxy)-3-(3-phenylpropoxy)benzaldehyde (1301, 100 g, 289 mmol) was dissolved in methylene chloride (DCM, 900 mL), and then meta-chloroperoxybenzoic acid (m-CPBA, 74.7 g, 433 mmol) was added thereto. The mixture was stirred at room temperature for about 16 hours. When the reaction was completed, the reaction mixture was filtered and then concentrated. The concentrated solution was purified by column chromatography using silica gel (ethyl acetate/petroleum ether=1:15 to 1:5). Thereby, 4-(benzyloxy)-3-(3-phenylpropoxy)phenol (1302, 66 g) was obtained as a grayish white solid. $^1$H NMR (DMSO-d$_6$, 400 MHz) δ (ppm) 9.00 (s, 1H), 7.44-7.18 (m, 10H), 6.81 (d, J=8 Hz, 1H), 6.39 (d, J=2.8 Hz, 1H), 6.22 (dd, J=8.8 Hz and 2.8 Hz, 1H), 4.96 (s, 2H), 3.90 (t, J=6 Hz, 2H), 2.74 (t, J=8 Hz, 2H), 2.01 (q, J=5.6 Hz, 2H)

Step 4) Preparation of (R)-2-((4-(benzyloxy)-3-(3-phenylproxy)phenoxy)methyl)oxirane (A-4)

4-(Benzyloxy)-3-(3-phenylpropoxy)phenol (1302, 40 g, 60 mmol) was dissolved in ethanol (EtOH, 800 mL), and then water (40 mL) and potassium hydroxide (KOH, 8.0 g, 143 mmol) were added thereto. Then, (R)-2-(chloromethyl)oxirane (33.2 g, 359 mmol) was added and then stirred at room temperature for about 16 hours. When the reaction was completed, water (1600 mL) was added to the reaction solution to complete the reaction, and the compound was extracted with ethyl acetate (1600 mL×3). The extracted organic solvent layer was washed with brine, and then the remaining water was removed with sodium sulfate. The impurities were removed by a filter and then concentrated. The concentrated solution was purified by column chromatography using silica gel (ethyl acetate/petroleum ether=1: 15 to 1:10). Thereby, (R)-2-((4-(benzyloxy)-3-(3-phenylproxy)phenoxy)methyl)oxirane (A-4, 30 g) was obtained as a white solid. $^1$H NMR (DMSO-d$_6$, 400 MHz) (ppm) 7.46-7.17 (m, 10H), 6.93 (d, J=8.8 Hz, 1H), 6.61 (d, J=3.2 Hz, 1H), 6.43 (dd, J=8.8 Hz and 2.8 Hz, 1H), 5.02 (s, 2H), 4.23 (dd, J=7.6 Hz and 2.8 Hz, 1H), 3.97 (t, J=6.4 Hz, 2H), 3.75 (dd, J=7.2 Hz and 1.6 Hz, 1H), 3.28 (m, 1H), 2.82 (dd, J=5.2 Hz and 4 Hz, 1H), 2.75 (t, J=7.6 Hz, 2H), 2.73-2.67 (m, 1H), 2.01 (m, 2H)

Step 5) Preparation of tert-butyl (2-(2-(2-hydroxyethoxy)ethoxy)ethyl)carbamate (L-4)

2-(2-(2-Aminoethoxy)ethoxy)ethan-1-ol (L-3, 5 g, 33 mmol) was dissolved in methylene chloride (DCM, 100 mL), and then triethylamine (TEA, 4.1 g, 40 mmol) and di-tert-butyl dicarbonate (Boc$_2$O, 8.1 g, 37 mmol) were added thereto. The mixture was stirred at room temperature for about 16 hours. When the reaction was completed, the reaction mixture was filtered and then concentrated. The concentrated solution was purified by column chromatography using silica gel (EA/PE=1:3 to 1:1). Thereby, tert-butyl (2-(2-(2-hydroxyethoxy)ethoxy)ethyl)carbamate (L-4, 4.2 g) was obtained as a colorless liquid. $^1$H NMR (DMSO-d$_6$, 400 MHz) δ (ppm) 6.74 (m, 1H), 4.56 (t, J=5.6 Hz, 1H), 3.51-3.46 (m, 6H), 3.42-3.37 (m, 4H), 3.07-3.03 (m, 2H), 1.37 (s, 9H)

Step 6) Preparation of tert-butyl(2-(2-(2-(4-(2-phenyl-5,7-bis(trifluoromethyl)pyrazolo[1,5-a]pyrimidin-3-yl)phenoxy)ethoxy)ethoxy)ethyl)carbamate (TL-4)

Tert-butyl (2-(2-(2-hydroxyethoxy)ethoxy)ethyl)carbamate (L-4, 300 mg, 1.2 mmol) was dissolved in tetrahydrofuran (THF, 5 mL), and then 4-[2-phenyl-5,7-bis(trifluoromethyl)pyrazolo[1,5-a]pyrimidin-3-yl]phenol (PHTPP, 509 mg, 1.2 mmol), triphenylphosphine (PPh$_3$, 377 mg, 1.44 mmol) and diisopropyl azodicarboxylate (DIAD, 291 mg, 1.44 mmol) were added thereto. The mixture was stirred at 65° C. for about 16 hours. After the reaction was completed, the reaction was terminated, and the solution was filtered and concentrated. The concentrated solution was purified by column chromatography using silica gel (DCM/MeOH=100:1 to 50:1). Thereby, tert-butyl (2-(2-(2-(4-(2-phenyl-5,7-bis(trifluoromethyl)pyrazolo[1,5-a]pyrimidin-3-yl)phenoxy)ethoxy)ethoxy)ethyl)carbamate (TL-4, 200 mg) was obtained as a yellow solid.

Step 7) Preparation of 2-(2-(2-(4-(2-phenyl-5,7-bis(trifluoromethyl)pyrazolo[1,5-a]pyrimidin-3-yl)phenoxy)ethoxy)ethoxy)ethan-1-amine (TL-5)

Tert-butyl (2-(2-(2-(4-(2-phenyl-5,7-bis(trifluoromethyl)pyrazolo[1,5-a]pyrimidin-3-yl)phenoxy)ethoxy)ethoxy)ethyl)carbamate (TL-4, 200 mg, 0.31 mmol) was dissolved in ethyl acetate (EA, 4 mL), and then hydrochloric acid (g)/ethyl acetate (1 mL) was added thereto. The mixture was stirred at room temperature for about 2 hours. After the reaction was completed, the reaction was terminated and the solution was filtered and concentrated. The concentrated solution was subjected to a purification process, and thereby 2-(2-(2-(4-(2-phenyl-5,7-bis(trifluoromethyl)pyrazolo[1,5-a]pyrimidin-3-yl)phenoxy)ethoxy)ethoxy)ethan-1-amine (TL-5, 120 mg) was obtained as a yellow solid.

Step 8) Preparation of (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol (PHTPP-1304)

2-(2-(2-(4-(2-phenyl-5,7-bis(trifluoromethyl)pyrazolo[1,5-a]pyrimidin-3-yl)phenoxy)ethoxy)ethoxy)ethan-1-amine (TL-5, 120 mg, 0.22 mmol) was dissolved in methanol (MeOH, 2 mL), and then (R)-2-((4-(benzyloxy)-3-(3-phenylproxy)phenoxy)methyl)oxirane (A-4, 117 mg, 0.33 mmol) was added thereto. The mixture was stirred at 65° C. for about 16 hours. After the reaction was completed, the reaction was terminated, and the solution was filtered and concentrated. The concentrated solution was purified by preparative high performance liquid chromatography (Prep-HPLC). Thereby, (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol (PHTPP-1304, 15 mg) was obtained as a yellow solid. $^1$H NMR (DMSO-d$_6$, 400 MHz) δ (ppm) 1.99 (m, 2H), 2.73 (m, 6H), 3.55 (m, 8H), 3.80 (m, 5H), 3.94 (t, J=8 Hz, 2H), 4.13 (t, J=4 Hz, 2H), 4.99 (s, 2H), 6.40 (d, J=8 Hz, 1H), 6.55 (d, J=4 Hz, 1H), 6.89 (d, J=8 Hz, 1H), 7.04 (d, J=8 Hz, 2H), 7.18 (t, J=4 Hz, 3H), 7.27 (dd, J=4 Hz and 4 Hz, 3H), 7.35 (m, 4H), 7.44 (m, 5H), 7.61 (m, 2H), 8.07 (s, 1H), 8.42 (s, 1H); ESI-MS Calcd m/z for C$_{51}$H$_{50}$F$_6$N$_4$O$_7$[M+H]$^+$ 945.10 Found 944.97.

Example 9: Preparation of (R,Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol (Baicalein-2204)

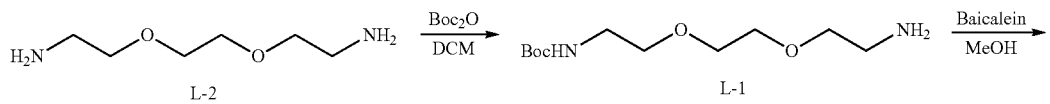

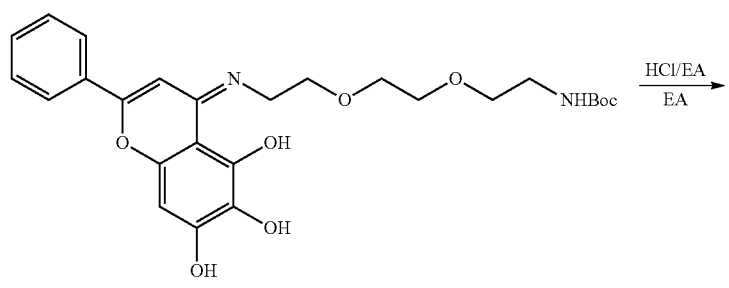

TL-6

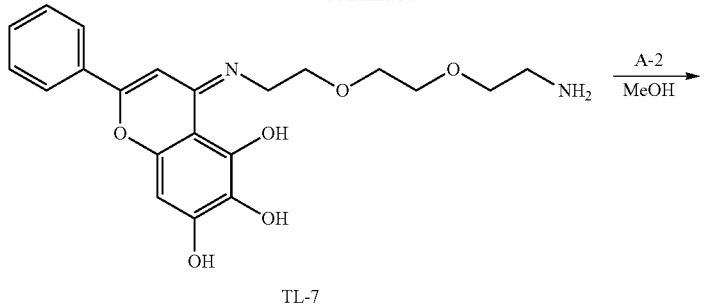

TL-7

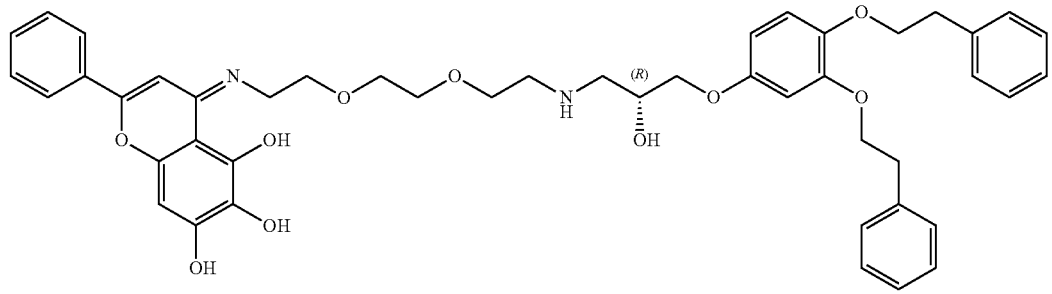

Baicalein-2204

Step 1) Preparation of tert-butyl (2-(2-(2-aminoethoxy)ethoxy)ethyl)carbamate (L-1)

2,2'-(Ethane-1,2-diylbis(oxy))dietanamine (L-2, 5 g, 33.7 mmol) was dissolved in methylene chloride (DCM, 100 mL), and then di-tert-butyl dicarbonate ($Boc_2O$, 7.36 g, 33.7 mmol) was added thereto. The mixture was stirred at room temperature for about 16 hours. After the reaction was completed, the reaction solution was filtered and concentrated. The concentrated solution was purified by column chromatography using silica gel (ethyl acetate/petroleum ether=1:3 to 1:1). Thereby, tert-butyl (2-(2-(2-aminoethoxy)ethoxy)ethyl)carbamate (L-2, 2.2 g) was obtained as a colorless liquid.

Step 2) Preparation of tert-butyl (Z)-(2-(2-(2-((5,6,7-trihydroxy-2-phenyl-4H-chromen-4-ylidene)amino)ethoxy)ethoxy)ethyl)carbamate (TL-6)

Tert-butyl (2-(2-(2-aminoethoxy)ethoxy)ethyl)carbamate (TL-6, 300 mg, 1.21 mmol) was dissolved in methanol (MeOH, 5 mL), and then 5,6,7-trihydroxyflavone (Baicalein, 326 mg, 1.21 mmol) was added thereto. The mixture was stirred at 65° C. for about 16 hours. When the reaction was completed, the reaction solution was filtered and then concentrated. The concentrated solution was purified by preparative high performance liquid chromatography (Prep-HPLC). Thereby, tert-butyl (Z)-(2-(2-(2-((5,6,7-trihydroxy-2-phenyl-4H-chromen-4-ylidene)amino)ethoxy)ethoxy)ethyl)carbamate (TL-6, 120 mg) was obtained as a yellow solid.

Step 3) Preparation of (Z)-4-((2-(2-(2-aminoethoxy)ethoxy)ethyl)imino)-2-phenyl-4H-chromen-5,6,7-triol (TL-7)

Tert-butyl (Z)-(2-(2-(2-((5,6,7-trihydroxy-2-phenyl-4H-chromen-4-ylidene)amino)ethoxy)ethoxy)ethyl)carbamate (TL-6, 120 mg, 0.24 mmol) was dissolved in ethyl acetate (EA, 2 mL), and then hydrochloric acid (g)/ethyl acetate (1 mL) was added thereto. The mixture was stirred at room temperature for about 2 hours. When the reaction was completed, the reaction mixture was extracted with ethyl acetate, filtered and concentrated. Thereby, (Z)-4-((2-(2-(2-aminoethoxy)ethoxy)ethyl)imino)-2-phenyl-4H-chromen-5,6,7-triol (TL-7, 90 mg) was obtained as a yellow solid.

Step 4) Preparation of (R,Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol (Baicalein-2204)

(Z)-4-((2-(2-(2-aminoethoxy) ethoxy) ethyl) imino)-2-phenyl-4H-chromen-5,6,7-triol (TL-7, 90 mg, 0.22 mmol) was dissolved in methanol (MeOH, 2 mL), and then (R)-2-((3,4-diphenethoxyphenoxy)methyl)oxirane (A-2, 87 mg, 0.22 mmol) was added thereto. The mixture was stirred at 65° C. for about 16 hours. When the reaction was completed, the reaction solution was filtered and then concentrated. The concentrated solution was purified by preparative high performance liquid chromatography (Prep-HPLC). Thereby, (R,Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol (Baicalein-2204, 12 mg) was obtained as a yellow solid. $^1$H NMR (DMSO-$d_6$, 400 MHz) δ (ppm) 2.91 (m, 7H), 3.35 (m, 11H), 3.80 (m, 3H), 3.96 (t, J=8 Hz, 2H), 4.08 (t, J=8 Hz, 2H), 6.32 (dd, J=4 Hz and 4 Hz, 1H), 6.37 (s, 1H), 6.47 (s, 1H), 6.76 (d, J=12 Hz, 2H), 7.25 (m, 10H), 7.58 (t, J=4 Hz, 3H), 7.99 (d, J=8 Hz, 2H), 8.42 (s, 1H); ESI-MS Calcd m/z for $C_{46}H_{50}N_2O_0$ [M+H]$^+$ 791.20 Found 790.91.

Example 10: Preparation of E)-5-(4-(2-(2-(2-((3,4-bis(benzyloxy)benzyl)amino)ethoxy)ethoxy)ethoxy)styryl)benzene-1,3-diol (Resveratrol-1105)
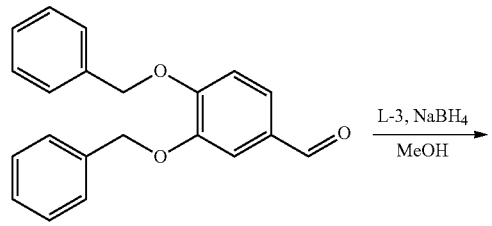
1101
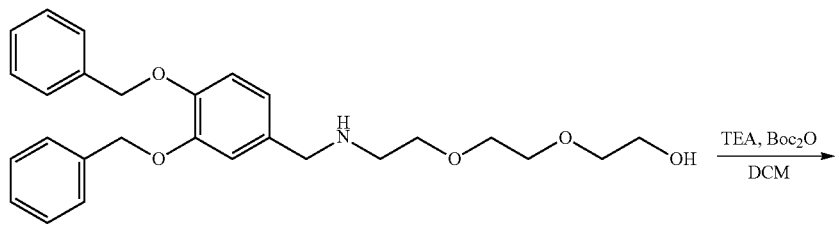
AL-5
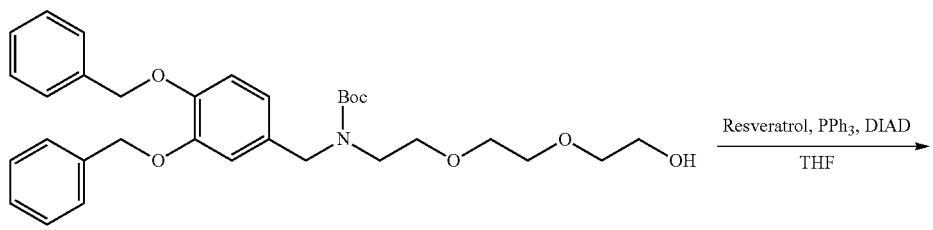
AL-6
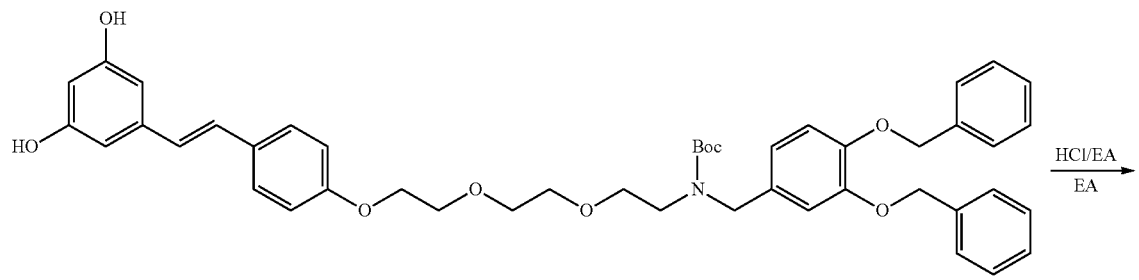
ATL-1
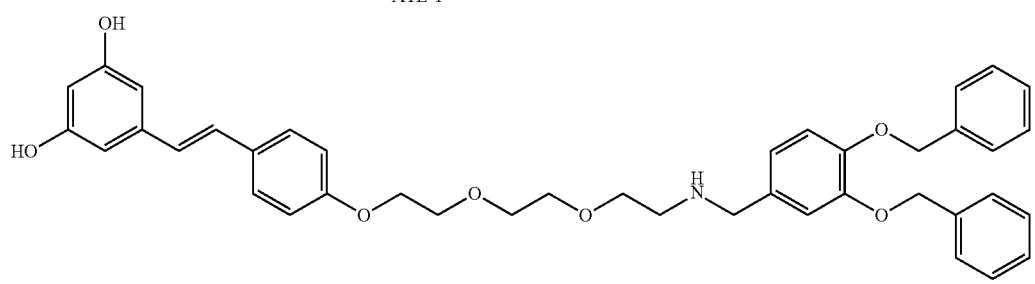
Resveratrol-1105

Step 1) Preparation of 2-(2-(2-((3,4-bis(benzyloxy)benzyl)amino)ethoxy)ethoxy)ethan-1-ol (AL-5)

3,4-Bis(benzyloxy)benzaldehyde (1101, 25 g, 78.6 mmol) was dissolved in methanol (MeOH, 250 mL), and then 2-(2-(2-aminoethoxy)ethoxy)ethanol (L-3, 11.7 g, 78.6 mmol) was added thereto. The mixture was stirred at 65° C. for about 6 hours. After cooling to room temperature, sodium borohydride (NaBH$_4$, 3 g, 78.6 mmol) was further added and then stirred at 50° C. overnight. Water was added to the reaction solution to complete the reaction, and the compound was extracted with ethyl acetate (EtOAc, 50 mL×3). The extracted compound was washed with brine, and the remaining water was removed with sodium sulfate. After filtering, the solution was concentrated and the concentrated solution was purified by column chromatography using silica gel (methylene chloride/methanol=20:1). Thereby, 2-(2-(2-((3,4-bis(benzyloxy)benzyl)amino)ethoxy)ethoxy)ethan-1-ol (AL-5, 13 g) was obtained as a yellow liquid. $^1$H NMR (DMSO-d$_6$, 400 MHz) δ (ppm) 7.46-7.30 (m, 10H), 7.06 (d, J=1.6 Hz, 1H), 6.97 (d, J=8 Hz, 1H), 6.82 (d, J=1.2 Hz, 1H), 5.10 (d, J=4 Hz, 4H), 3.61 (s, 2H), 3.50-3.39 (m, 11H), 2.58 (t, J=6 Hz, 2H) ESI-MS Calcd m/z for C$_{27}$H$_{33}$N$_5$O$_5$ [M+H]$^+$ 452.10 Found 451.56.

Step 2) Preparation of tert-butyl (3,4-bis(benzyloxy)benzyl)(2-(2-(2-hydroxyethoxy)ethoxy)ethyl)carbamate (AL-6)

2-(2-(2-((3,4-Bis(benzyloxy)benzyl)amino)ethoxy)ethoxy)ethan-1-ol (AL-5, 500 mg, 1.11 mmol) was dissolved in methylene chloride (DCM, 6 mL), and then triethylamine (TEA, 168 mg, 1.66 mmol) and di-tert-butyl dicarbonate (Boc$_2$O, 290 mg, 1.33 mmol) were added thereto. The mixture was stirred at room temperature for about 4 hours. When the reaction was completed, the reaction solution was filtered and then concentrated. The concentrated solution was purified by column chromatography using silica gel (ethyl acetate/petroleum ether=1:5 to 1:1). Thereby, colorless tert-butyl (3,4-bis(benzyloxy)benzyl) (2-(2-(2-hydroxyethoxy)ethoxy)ethyl)carbamate (AL-6, 520 mg) was obtained.

Step 3) Preparation of tert-butyl (E)-(3,4-bis(benzyloxy)benzyl)(2-(2-(2-(4-(3,5-dihydroxystyryl)phenoxy)ethoxy)ethoxy)ethyl)carbamate (ATL-1)

Tert-butyl (3,4-bis(benzyloxy)benzyl)(2-(2-(2-hydroxyethoxy)ethoxy)ethyl)carbamate (AL-6, 300 mg, 0.54 g) was dissolved in tetrahydrofuran (THF, 5 mL), and then resveratrol (149 mg, 0.65 mmol), triphenylphosphine (PPh$_3$, 214 mg, 0.82 mmol) and diisopropyl azodicarboxylate DIAD (165 mg, 0.82 mmol) were added thereto. The mixture was stirred at 65° C. for about 16 hours. After the reaction was completed, the reaction solution was filtered and then concentrated. The concentrated solution was purified by column chromatography using silica gel (methylene chloride/methanol=100:1 to 50:1). Thereby, tert-butyl (E)-(3,4-bis(benzyloxy)benzyl)(2-(2-(2-(4-(3,5-dihydroxystyryl)phenoxy)ethoxy)ethoxy)ethyl)carbamate (ATL-1, 200 mg) was obtained as a yellow solid.

Step 4) Preparation of E)-5-(4-(2-(2-(2-((3,4-bis(benzyloxy)benzyl)amino)ethoxy)ethoxy)ethoxy)styryl)benzene-1,3-diol (Resveratrol-1105)

Tert-butyl (E)-(3,4-bis(benzyloxy)benzyl)(2-(2-(2-(4-(3,5-dihydroxystyryl)phenoxy)ethoxy)ethoxy)ethyl)carbamate (ATL-1, 200 mg) was dissolved in ethyl acetate (EA, 4 mL), and then hydrochloric acid (g)/ethyl acetate (1 mL) was added thereto. The mixture was stirred at room temperature for about 2 hours. After the reaction was completed, the reaction solution was filtered and then concentrated. The concentrated solution was purified by high resolution liquid chromatography (Prep-HPLC). Thereby, E)-5-(4-(2-(2-(2-((3,4-bis(benzyloxy)benzyl)amino)ethoxy)ethoxy)ethoxy)styryl)benzene-1,3-diol (Resveratrol-1105, 15 mg) was obtained as a white solid. $^1$H NMR (DMSO-d$_6$, 400 MHz) (ppm) 2.58 (t, J=4 Hz, 2H), 3.45 (t, J=4 Hz, 2H), 3.51 (m, 2H), 3.57 (m, 4H), 3.73 (m, 2H), 4.06 (m, 2H), 5.07 (m, 4H), 6.12 (m, 1H), 6.40 (m, 2H), 6.90 (m, 7H), 7.39 (m, 12H), 9.20 (s, 2H); ESI-MS Calcd m/z for C$_{41}$H$_{43}$NO$_7$ [M+H]$^+$ 662.10 Found 661.80.

Example 11: Preparation of (R)-2-(4-(benzo[d]thiazol-2-yl) phenyl)-14-(3,4-bis(benzyloxy)phenoxy)-5,8-dioxa-2,11-diazatetradecane-13-ol (BTA-1-1104)

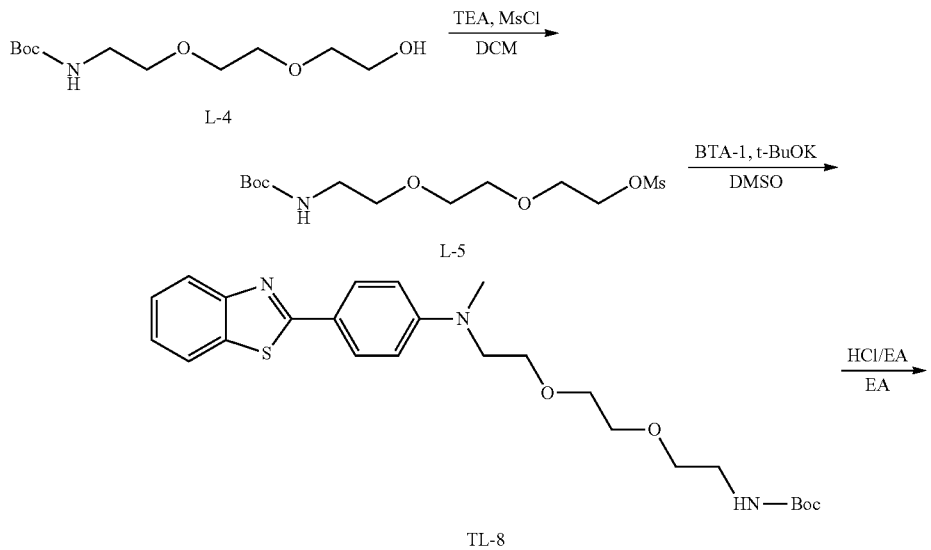

TL-8

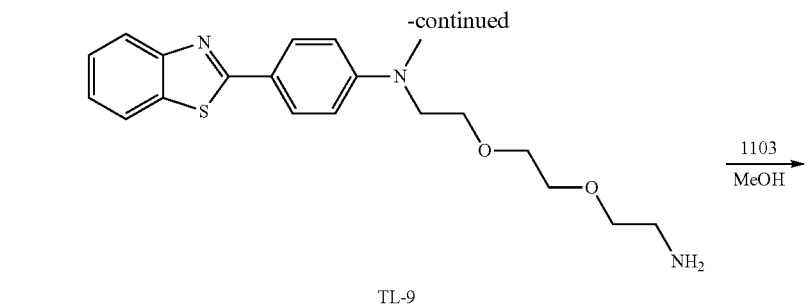

TL-9

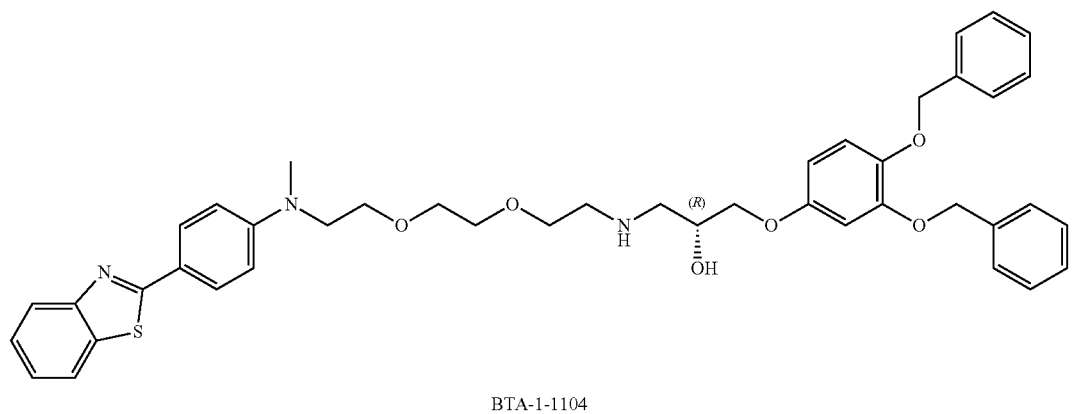

BTA-1-1104

Step 1) Preparation of 2,2-dimethyl-4-oxo-3,8,11-trioxa-5-azatridecane-13-yl-methanesulfonate (L-5)

Tert-butyl (2-(2-(2-hydroxyethoxy) ethoxy) ethyl) carbamate (L-4, 1 g, 4.0 mmol) was dissolved in methylene chloride (DCM, 15 mL), and then triethylamine (TEA, 0.486 g, 4.8 mmol) and methanesulfonyl chloride (MsCl, 0.504 g, 4.4 mmol) were added thereto. The mixture was stirred at room temperature for about 4 hours. When the reaction was completed, the compound was extracted, filtered and then concentrated. The concentrated solution was purified by column chromatography using silica gel (ethyl acetate/petroleum ether=1:5 to 1:1). Thereby, 2,2-dimethyl-4-oxo-3,8,11-trioxa-5-azatridecane-13-yl-methanesulfonate (L-5, 1 g) was obtained as a colorless liquid.

Step 2) Preparation of tert-butyl (2-(2-(2-((4-(benzo[d]thiazol-2-yl)phenyl)(methyl)amino)ethoxy)ethoxy)ethyl)carbamate (TL-8)

2,2-Dimethyl-4-oxo-3,8,11-trioxa-5-azatridecane-13-yl-methanesulfonate (L-5, 300 mg, 0.92 mmol) was dissolved in dimethyl sulfoxide (DMSO, 5 mL), and then 2-(4'-methylaminophenyl)benzothiazole (BTA-1, 220 mg, 0.92 mmol) and potassium tert-butoxide (t-BuOK, 154 mg, 1.37 mmol) were added thereto. The mixture was stirred at 120° C. for about 16 hours. When the reaction was completed, the reaction solution was filtered and then concentrated. The concentrated solution was purified by preparative high performance liquid chromatography (Prep-HPLC). Thereby, tert-butyl (2-(2-(2-((4-(benzo[d]thiazol-2-yl)phenyl)(methyl)amino)ethoxy)ethoxy)ethyl)carbamate (TL-8, 180 mg) was obtained as a yellow liquid.

Step 3) Preparation of N-(2-(2-(2-aminoethoxy)ethoxy)ethyl)-4-(benzo[d]thiazol-2-yl)-N-methylaniline (TL-9)

Tert-butyl (2-(2-(2-((4-(benzo[d]thiazol-2-yl)phenyl)(methyl)amino)ethoxy)ethoxy)ethyl)carbamate (TL-8, 180 mg, 0.38 mmol) was dissolved in ethyl acetate (EA, 4 mL), and then hydrochloric acid (g)/ethyl acetate (1 mL) was added thereto. The mixture was stirred at room temperature for 2 hours. When the reaction was completed, the compound was extracted, filtered and then concentrated. Thereby, N-(2-(2-(2-aminoethoxy)ethoxy)ethyl)-4-(benzo[d]thiazol-2-yl)-N-methylaniline (TL-9, 120 mg) was obtained as a yellow solid.

Step 4) Preparation of (R)-2-(4-(benzo[d]thiazol-2-yl)phenyl)-14-(3,4-bis(benzyloxy)phenoxy)-5,8-dioxa-2,11-diazatetradecane-13-ol (BTA-1-1104)

N-(2-(2-(2-aminoethoxy)ethoxy)ethyl)-4-(benzo[d]thiazol-2-yl)-N-methylaniline (TL-9, 120 mg, 0.33 mmol) was dissolved in methanol (MeOH, 2 mL), and then (R)-2-((3,4-bis(benzyloxy)phenoxy)methyl)oxirane (1103, 117 mg, 0.33 mmol) was added thereto. The mixture was stirred at 65° C. for about 16 hours. When the reaction was completed, the compound was extracted, filtered and then concentrated. The concentrated solution was purified by preparative high performance liquid chromatography (Prep-HPLC). Thereby, (R)-2-(4-(benzo[d]thiazol-2-yl)phenyl)-14-(3,4-bis(benzyloxy)phenoxy)-5,8-dioxa-2,11-diazatetradecane-13-ol (BTA-1-1104, 8 mg) was obtained as a yellow solid. $^1$H NMR (DMSO-$d_6$, 400 MHz) δ (ppm) 1.15 (d, J=8 Hz, 3H), 1.23 (s, 1H), 2.67 (m, 4H), 3.50 (m, 11H), 3.81 (m, 4H), 5.01 (s, 2H), 5.10 (s, 2H), 6.27 (d, J=8 Hz, 1H), 6.41 (d, J=8 Hz, 1H), 6.69 (m, 3H), 6.91 (d, J=12 Hz, 1H), 7.38 (m, 12H), 7.79 (d, J=8 Hz, 2H), 7.89 (d, J=8 Hz, 1H), 7.90 (d, J=8 Hz, 1H), 8.40 (s, 1H); ESI-MS Calcd m/z for $C_{43}H_{47}N_3O_6S$ $[M+H]^+$ 734.10 Found 733.92.
Example 12: Preparation of (1E,6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione (Curcumin-1204)
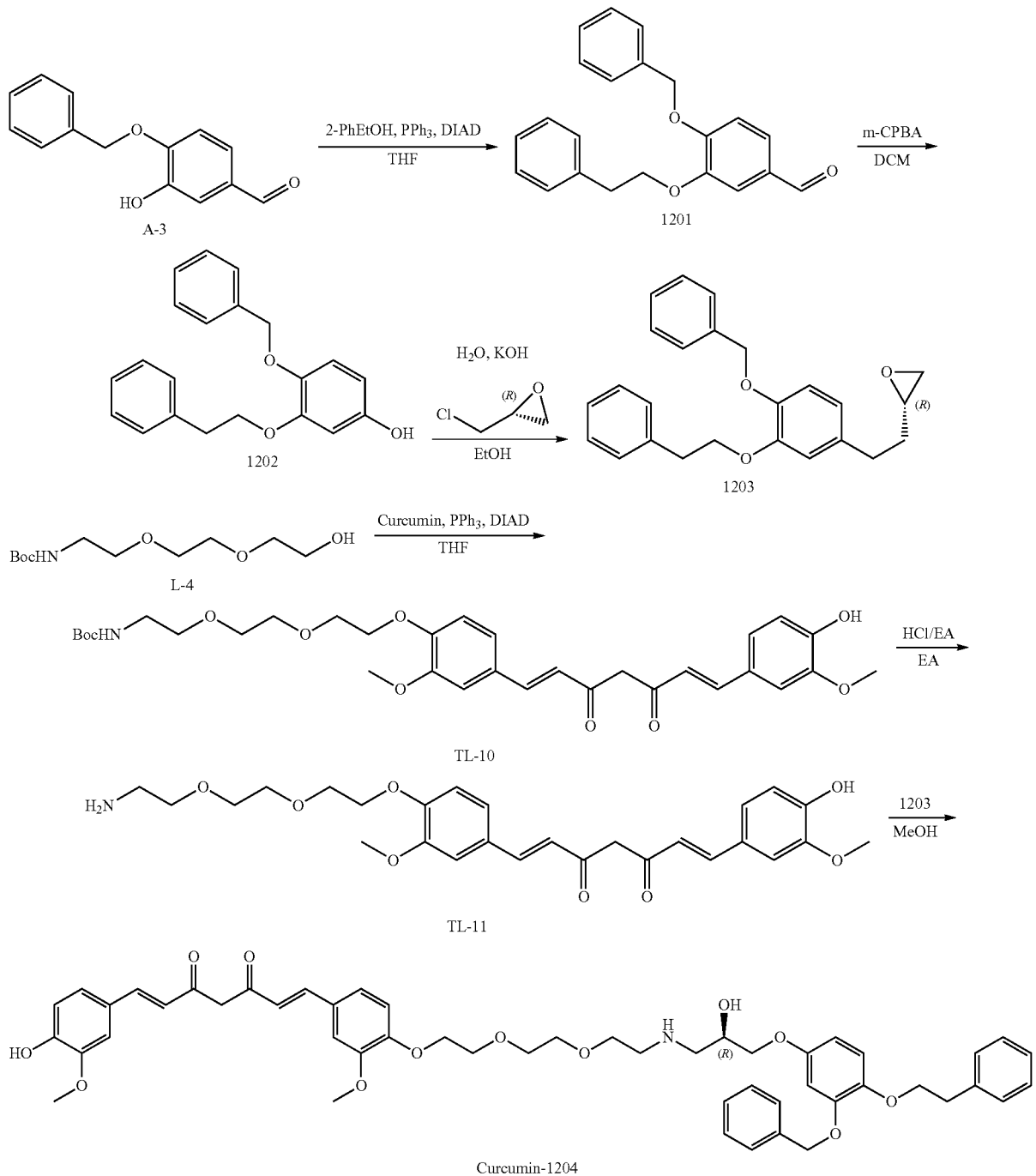

Step 1) Preparation of 4-(benzyloxy)-3-phenethoxybenzaldehyde (1201)

4-(Benzyloxy)-3-hydroxybenzaldehyde (A-3, 50 g, 219 mmol) was dissolved in tetrahydrofuran (THF, 1 L), and then 2-phenylethanol (32.1 g, 263 mmol), triphenylphosphine (PPh$_3$, 86.2 g, 329 mmol) and diisopropyl azodicarboxylate (DIAD, 66.4 g, 329 mmol) were added thereto. The mixture was stirred at 65° C. for about 16 hours. When the reaction was completed, the compound was extracted, filtered and concentrated. The concentrated solution was purified by column chromatography using silica gel (ethyl acetate/petroleum ether=1:15 to 1:10). Thereby, 4-(benzyloxy)-3-phenethoxybenzaldehyde (1201, 25 g) was obtained as a white solid.

$^1$H NMR (DMSO-d$_6$, 400 MHz) δ (ppm) 9.82 (s, 1H), 7.52 (dd, J=8 Hz and 2 Hz, 1H), 7.43-7.40 (m, 5H), 7.37-7.32 (m, 3H), 7.28-7.21 (m, 4H), 5.21 (s, 2H), 4.26 (t, J=6.4 Hz, 2H), 3.05 (t, J=6.4 Hz, 2H)

Step 2) Preparation of 4-(benzyloxy)-3-phenethoxyphenol (1202)

4-(benzyloxy)-3-phenethoxybenzaldehyde (1201, 50 g, 150 mmol) was dissolved in methylene chloride (DCM, 500 mL), and then meta-chloroperoxybenzoic acid (m-CPBA, 39 g, 225 mmol) was added thereto. The mixture was stirred at room temperature for about 16 hours. When the reaction was completed, the compound was extracted, filtered and concentrated. The concentrated solution was purified by column chromatography using silica gel (ethyl acetate/petroleum ether=1:15 to 1:5). Thereby, 4-(benzyloxy)-3-phenethoxyphenol (1202, 32 mg) was obtained as a white solid. $^1$H NMR (DMSO-d$_6$, 400 MHz) δ (ppm) 9.00 (s, 1H), 7.36-7.20 (m, 10H), 6.78 (d, J=8 Hz, 1H), 6.43 (d, J=2.8 Hz, 1H), 6.22 (dd, J=8 Hz and 2.8 Hz, 1H), 4.86 (s, 2H), 4.13 (t, J=6.8 Hz, 2H), 3.02 (t, J=6.4 Hz, 2H)

Step 3) Preparation of (R)-2-((4-(benzyloxy)-3-phenethoxyphenoxy)methyl)oxirane (1203)

4-(Benzyloxy)-3-phenethoxyphenol (1203, 40 g, 64 mmol) was dissolved in ethanol (EtOH, 800 mL), and then water (40 mL) and potassium hydroxide (KOH, 8.2 g, 146 mmol) were added thereto. Then, (R)-2-(chloromethyl)oxirane (34.6 g, 374 mmol) was added and further stirred at room temperature for 16 hours. Water (1600 mL) was added to the reaction solution to complete the reaction, and extracted with ethyl acetate (1600 mL×3). The extracted organic solvent layer was washed with brine, and the remaining water was removed with sodium sulfate. The resulting material was filtered to remove impurities, and concentrated. The concentrated solution was purified by column chromatography using silica gel (ethyl acetate/petroleum ether=1:15 to 1:10). Thereby, (R)-2-((4-(benzyloxy)-3-phenethoxyphenoxy)methyl)oxirane (1203, 34 g) was obtained as a white solid. $^1$H NMR (DMSO-d$_6$, 400 MHz) (ppm) 7.38-7.20 (m, 10H), 6.90 (d, J=8.8 Hz, 1H), 6.64 (d, J=2 Hz, 1H), 6.41 (dd, J=8.8 Hz and 2.8 Hz, 1H), 4.93 (s, 2H), 4.25-4.17 (m, 3H), 3.75 (dd, J=11.2 Hz and 6.4 Hz, 1H), 3.28 (m, 1H), 3.03 (t, J=6.8 Hz, 2H), 2.81 (t, J=4.4 Hz, 1H), 2.67 (dd, J=5.2 Hz and 2.8 Hz, 1H)

Step 4) Preparation of tert-butyl (2-(2-(2-(4-((1E,6E)-7-(4-hydroxy-3-methoxyphenyl)-3,5-dioxohepta-1,6-dien-1-yl)-2-methoxyphenoxy)ethoxy)ethoxy)ethyl)carbamate (TL-10)

Tert-butyl (2-(2-(2-hydroxyethoxy)ethoxy)ethyl)carbamate (L-4, 300 mg, 1.2 mmol) was dissolved in tetrahydrofuran (THF, 5 mL), and then curcumin (442 mg, 1.2 mmol), triphenylphosphine (PPh$_3$, 377 mg, 1.44 mmol) and diisopropyl azodicarboxylate (DIAD, 291 mg, 1.44 mmol) were added thereto. The mixture was stirred at 65° C. for about 16 hours. When the reaction was completed, the compound was extracted, filtered and concentrated. The concentrated solution was purified by column chromatography using silica gel (methylene chloride/methanol=100:1 to 50:1). Thereby, tert-butyl (2-(2-(2-(4-((1E,6E)-7-(4-hydroxy-3-methoxyphenyl)-3,5-dioxohepta-1,6-dien-1-yl)-2-methoxyphenoxy)ethoxy)ethoxy)ethyl)carbamate (TL-10, 200 mg) was obtained as a yellow solid. $^1$H NMR (DMSO-d$_6$, 400 MHz) δ (ppm) 9.87 (brs, 1H), 7.57 (dd, J=16 Hz and 4 Hz, 2H), 3.34 (dd, J=12 Hz and 1.6 Hz, 2H), 7.24 (dd, J=8 Hz and 1.2 Hz, 1H), 7.16 (dd, J=8 Hz and 1.2 Hz, 1H), 7.02 (d, J=8 Hz, 1H), 6.85-6.74 (m, 4H), 6.08 (s, 1H), 4.13 (t, J=4 Hz, 2H), 3.83 (m, 6H), 3.75 (t, J=4 Hz, 2H), 3.59 (q, J=4 Hz, 2H), 3.52 (q, J=4 Hz, 2H), 3.40-3.38 (m, 4H), 3.06 (q, J=6 Hz, 2H), 1.36 (s, 9H)

Step 5) Preparation of (1E,6E)-1-(4-(2-(2-(2-aminoethoxy)ethoxy)ethoxy)-3-methoxyphenyl)-7-(4-hydroxy-3-methoxyphenyl)hepta-1,6-diene-3,5-dione (TL-11)

Tert-butyl (2-(2-(2-(4-((1E,6E)-7-(4-hydroxy-3-methoxyphenyl)-3,5-dioxohepta-1,6-dien-1-yl)-2-methoxyphenoxy)ethoxy)ethoxy)ethyl)carbamate (TL-10, 200 mg, 0.33 mmol) was dissolved in ethyl acetate (EA, 4 mL), and then hydrochloric acid (g)/ethyl acetate (1 mL) was added thereto. The mixture was stirred at room temperature for about 2 hours. After the reaction was completed, the compound was extracted, filtered and then concentrated. Thereby, (1E,6E)-1-(4-(2-(2-(2-aminoethoxy) ethoxy) ethoxy)-3-methoxyphenyl)-7-(4-hydroxy-3-methoxyphenyl)hepta-1,6-diene-3,5-dione (TL-11, 120 mg) was obtained as a yellow solid.

Step 6) Preparation of (1E, 6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione (Curcumin-1204)

(1E, 6E)-1-(4-(2-(2-(2-aminoethoxy)ethoxy)ethoxy)-3-methoxyphenyl)-7-(4-hydroxy-3-methoxyphenyl)hepta-1, 6-diene-3,5-dione (TL-11, 120 mg, 0.24 mmol) was dissolved in methanol (MeOH, 2 mL), and then (R)-2-((4-(benzyloxy)-3-phenethoxyphenoxy)methyl)oxirane (1203, 90 mg, 0.24 mmol) was added thereto. The mixture was stirred at 65° C. for about 16 hours. When the reaction was completed, the compound was extracted, filtered and then concentrated. The concentrated solution was purified by preparative high performance liquid chromatography (Prep-HPLC). Thereby, (1E,6E)-1-(4-(2-(2-(2-(((R)-3-(3-(benzyloxy)-4-phenethoxyphenoxy)-2-hydroxypropyl)amino) ethoxy)ethoxy)ethoxy)-3-methoxyphenyl)-7-(4-hydroxy-3-methoxyphenyl)hepta-1,6-diene-3,5-dione (Curcumin-1204, 12 mg) was obtained as a yellow solid. $^1$H NMR (DMSO-d$_6$+D$_2$O, 400 MHz) δ (ppm) 2.81 (m, 1H), 2.92 (m, 3H), 3.00 (t, J=6.4 Hz, 2H), 3.56 (m, 9H), 3.80 (m, 9H), 3.97 (b, 2H), 4.09 (m, 2H), 4.14 (t, J=6.4 Hz, 2H), 4.88 (s, 2H), 6.36 (d, J=8.8 Hz and 2.8 Hz, 1H), 6.56 (d, J=2.8 Hz, 1H), 6.79 (m, 4H), 6.97 (d, J=8 Hz, 1H), 7.23 (m, 14H), 7.53 (d, J=16 Hz, 2H), 8.33 (s, 1H); ESI-MS Calcd m/z for C$_{51}$H$_{57}$NO$_{12}$ [M]+876.10 Found 876.01.

Example 13: Preparation of (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol (Riluzole-204)

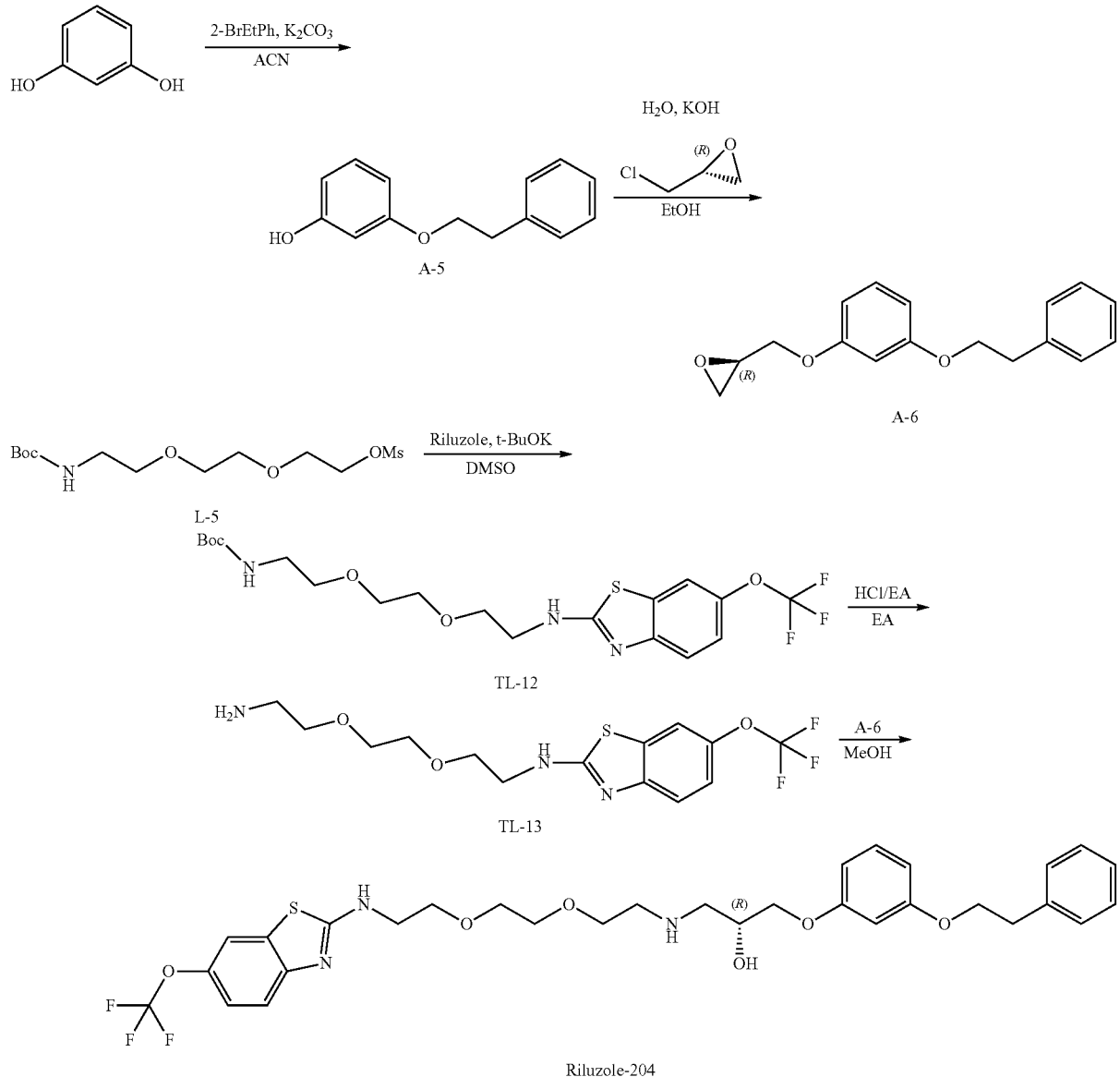

Riluzole-204

Step 1) Preparation of 3-phenethoxyphenol (A-5)

Resorcinol (50 g, 0.45 mol) was dissolved in acetonitrile (ACN, 500 mL), and then potassium carbonate ($K_2CO_3$, 112.5 g, 0.81 mol) and (2-bromoethyl)benzene (83.2 g, 0.45 mol) were added thereto. The mixture was stirred at 60° C. for about 10 hours. After the reaction was completed, the compound was extracted, filtered and concentrated. The concentrated solution was purified by column chromatography using silica gel (petroleum ether/ethyl acetate=5:1). Thereby, 3-phenethoxyphenol (A-5, 25 g) was obtained as a yellow liquid. $^1$H NMR ($CDCl_3$, 400 MHz) δ (ppm) 7.31-7.23 (m, 5H), 7.11 (t, J=8 Hz, 1H), 6.50-6.39 (m, 3H), 4.74 (s, 1H), 4.14 (m, 2H), 3.08 (t, J=7.2 Hz, 2H)

Step 2) Preparation of (R)-2-((3-phenethoxyphenoxy)methyl)oxirane (A-6)

3-Phenethoxyphenol (A-5, 25 g, 116.8 mmol) was dissolved in ethanol (EtOH, 500 mL), and then water (25 mL) and potassium hydroxide (KOH, 11.1 g, 278.3 mmol) were added thereto. Then, (R)-2-(chloromethyl)oxirane (64.6 g, 698.8 mmol) was added and then stirred at room temperature for about 16 hours. Water (1000 mL) was added to the reaction solution to complete the reaction, and the compound was extracted with ethyl acetate (500 mL×3). The extracted organic solvent layer was washed with brine, and the remaining water was removed with sodium sulfate. The resulting material was filtered to remove impurities, and concentrated. The concentrated solution was purified by column chromatography using silica gel (ethyl acetate/petroleum ether=1:15 to 1:10). Thereby, (R)-2-((3-phenethoxyphenoxy)methyl)oxirane (A-6, 18 g) was obtained as a yellow liquid. $^1$H NMR (DMSO-d$_6$, 400 MHz) (ppm) 7.32-7.28 (m, 4H), 7.24-7.14 (m, 2H), 6.52 (m, 3H), 4.29 (dd, J=11.2 Hz and 2 Hz, 1H), 4.16 (t, J=6.8 Hz, 2H), 3.79 (m, 1H), 3.34 (s, 1H), 3.01 (t, J=6 Hz, 2H), 2.82 (t, J=4 Hz, 1H), 2.69-2.67 (m, 1H)

Step 3) Preparation of tert-butyl (2-(2-(2-((6-(trifluoromethoxy)benzo[d]thiazol-2-yl)amino)ethoxy)ethoxy)ethyl)carbamate (TL-12)

2,2-Dimethyl-4-oxo-3,8,11-trioxa-5-azatridecane-13-yl-methanesulfonate (L-5, 300 mg, 0.92 mmol) was dissolved in dimethylsulfoxide (DMSO, 5 mL), and then riluzole (214 mg, 0.92 mmol) and potassium tert-butoxide (t-BuOK, 154 mg, 1.37 mmol) were added thereto. The mixture was stirred at 120° C. for about 16 hours. After the reaction was completed, the compound was extracted, filtered and then concentrated. The concentrated solution was purified by preparative high performance liquid chromatography (Prep-HPLC). Thereby, tert-butyl(2-(2-(2-((6-(trifluoromethoxy)benzo[d]thiazol-2-yl)amino)ethoxy)ethoxy)ethyl)carbamate (TL-12, 180 mg) was obtained as a pale yellow liquid. $^1$H NMR (DMSO-d$_6$, 400 MHz) δ (ppm) 8.27-8.25 (m, 1H), 7.78 (d, J=1.6 Hz, 1H), 7.41 (d, J=8 Hz, 1H), 7.18 (dd, J=8 Hz and 1.6 Hz, 1H), 6.74 (m, 1H), 3.63-3.51 (m, 12H), 3.05 (q, J=6 Hz, 2H), 1.36 (s, 11H)

Step 4) Preparation of N-(2-(2-(2-aminoethoxy)ethoxy)ethyl)-6-(trifluoromethoxy)benzo[d]thiazol-2-amine (TL-13)

Tert-butyl (2-(2-(2-((6-(trifluoromethoxy)benzo[d]thiazol-2-yl)amino)ethoxy)ethoxy)ethyl)carbamate (TL-12, 180 mg, 0.39 mmol) was dissolved in ethyl acetate (EA, 4 mL), and then hydrochloric acid (g)/ethyl acetate (1 mL) was added thereto. The mixture was stirred at room temperature for about 2 hours. When the reaction was completed, the compound was extracted, filtered and concentrated. Thereby, N-(2-(2-(2-aminoethoxy)ethoxy)ethyl)-6-(trifluoromethoxy)benzo[d]thiazol-2-amine (TL-13, 120 mg) was obtained as a yellow solid.

Step 5) Preparation of (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol (Riluzole-204)

N-(2-(2-(2-aminoethoxy)ethoxy)ethyl)-6-(trifluoromethoxy)benzo[d]thiazol-2-amine (TL-13, 120 mg, 0.33 mmol) was dissolved in methanol (MeOH, 2 mL), and then (R)-2-((3-phenethoxyphenoxy)methyl)oxirane (A-6, 89 mg, 0.33 mmol) was added thereto. The mixture was stirred at 65° C. for about 16 hours. After the reaction was completed, the compound was extracted, filtered and concentrated. The concentrated solution was purified by preparative high performance liquid chromatography (Prep-HPLC). Thereby, (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol (Riluzole-204, 15 mg) was obtained as a colorless liquid. $^1$H NMR (400 MHz, DMSO-d$_6$) δ (ppm) 2.60 (m, 4H), 3.00 (t, J=8 Hz, 2H), 3.52 (m, 10H), 3.85 (m, 3H), 4.15 (t, J=8 Hz, 2H), 6.48 (dd, J=12 Hz and 8 Hz, 3H), 7.18 (m, 3H), 7.31 (d, J=4 Hz, 4H), 7.43 (d, J=12 Hz, 1H), 7.75 (s, 1H); ESI-MS Calcd m/z for C$_{31}$H$_{66}$F$_3$N$_3$O$_6$S [M+H]$^+$ 636.10 Found 635.70.

Experimental Example 1. Evaluation of Oligomerization Activity of p62 Protein in Cultured Cells by Immunoblotting In order to evaluate the p62 protein oligomerization activity efficacy by the compounds 1 to 13 (Examples 1-13), HEK293 cell line, which is human embryonic kidney-derived cell, was collected. Cells were treated with the compounds of Examples and p62 ligand compound YTK-1105, and the cells were treated with DMSO as a control.

In order to measure intracellular p62 protein activation and oligomerization in cells according to the treatment with these compounds, the respective cells were dispensed into a 100 pi dish. The cells were collected after further culturing for 24 hours so that the cells were completely attached to the surface of the plate. 100 ul of lysis buffer (20 mM Tris (pH 7.4), 150 mM NaCl, 1% Triton X-100, 2 mM NaF, 2 mM EDTA, 2 mM beta-glycerophosphate, 5 mM sodium orthovanadate, 1 mM PMSF, leupeptin, aprotinin) were injected into each sample and the cells were lysed. Based on the measured total protein concentration, each sample was treated with test compounds at room temperature for 2 hours, and then a sample buffer was added and allowed to react at 95° C. for 10 minutes. 25 ul was taken from the samples after the reaction, and dispensed into each well of acrylamide gel, and then immunoblotting was performed. Immunoblotting showed representative results from three or more independent experiments. The results are shown in FIGS. 2a to 2c.

As seen in FIGS. 2a to 2c, it was confirmed that when treated with the AUTOTAC chimeric compounds according to the present invention as well as p62 ligand compound YTK-1105, it resulted in a decrease of the monomer of p62 proteins and simultaneously an increase in oligomers and high-molecular aggregates, unlike when treated with DMSO as a control.

Experimental Example 2. Evaluation of of Target Protein Degradation in Cultured Cells by Immunoblotting In order to evaluate the target protein degradation efficacy by the compounds (Examples 1-13), cell lines primarily expressing target proteins (MCF7, NTERA-2, ACHN, U87-MG, LNCaP, HEK293T) or gene recombinant cell lines (SH-SY5Y-tau, HeLa-HttQ97, PC12-a-synA30P) were cultured in a 12-well plate, and treated with the corresponding AUTOTAC chimeric compounds according to the concentration, and then immunoblotting was performed as in Experimental Example 1. Immunoblotting showed representative results from three or more independent experiments. The results are shown in FIGS. 3a, 3b and 3c.

As seen in FIGS. 3a, 3b and 3c, when treated with the AUTOTAC chimeric compounds according to the present invention, it was confirmed that the target protein level gradually increased according to the concentration of the compounds.

Experimental Example 3. Evaluation of Target Protein Degradation Mechanism in Cultured Cells by Immunoblotting In order to evaluate whether the target protein degradation mechanism of the aforementioned compounds (Example 1-13) was mediated by autophagy, cell lines primarily expressing target proteins or gene recombinant cell lines were cultured in 12-well plates, and treated with 2.5 uM of the corresponding AUTOTAC chimeric compound alone, or treated in combination with 10 uM of hydrxoxychloroquine (HCQ), an inhibitor of the autophagy-lysosomal pathway, and then immunoblotting was performed as in Experimental Example 1. Immunoblotting showed representative results from three or more independent experiments. The results are shown in FIGS. 4a and 4b.

As seen in FIGS. 4a and 4b, it was confirmed that when treated with the AUTOTAC chimeric compound according to the present invention alone, the target protein level decreased, and that when treated in combination with HCQ, an inhibitor of the autophagy-lysosomal pathway, the decreased target protein level again increased.

Experimental Example 4. Comparison Evaluation of Target Protein Degradation Efficacy in Cultured Cells by Immunoblotting In order to evaluate whether the target protein degradation efficacy of the compounds (Examples 1-13) is superior to the target protein degradation efficacy of the p62 ligand or target protein ligand, which is a chimeric component, cell lines primarily expressing target proteins or gene recombinant cell lines were cultured in 12-well plates, and treated with the corresponding AUTOTAC chimeric compound, p62 ligand or target protein ligand, and then immunoblotting was performed as in Experimental Example 1. Immunoblotting showed representative results from three or more independent experiments. The results are shown in FIGS. 5a to 5c.

As seen in FIGS. 5a to 5c, it was confirmed that after treatment with the AUTOTAC chimeric compound according to the present invention, the target protein level was significantly decreased as compared with that after treatment with the p62 ligand or target protein ligand.

Experimental Example 5. Evaluation of the Activity of P62-Mediated Delivery of Target Proteins in Cultured Cells to Autophagy by Immunofluorescence Staining and Confocal Microscopy In order to confirm the efficacy of P62-mediated delivery of target proteins to autophagy after treatment with the compounds (Examples 1-13), immunofluorescence staining was performed by using p62 and each target protein as markers. The cover glass was placed on a 24-well plate for immunofluorescence staining, cell lines primarily expressing the target protein or gene recombinant cell lines were cultured. The cells were dispensed and cultured 24 hours, and then treated with 2.5 uM of the novel AUTOTAC chimeric ligands according to the present invention. The cells were further cultured for 24 hours for the action of the compounds, the medium was removed, and the cells were fixed using formaldehyde at room temperature. In order to prevent non-specific staining, the cells were reacted with the blocking solution at room temperature for 1 hour, and then the p62 antibody and target protein antibody diluted at a certain ratio were treated using the block solution, and then reacted at room temperature for 1 hour. After the antibody-treated cells were washed three times with PBS, the goat-derived secondary antibody was diluted to a certain ratio using a blocking solution, and then reacted at room temperature for 30 minutes. The cells were washed again with PBS three times, and subjected to DAPI staining for intracellular nuclear staining, and then the level of expression of p62 and LC3, intracellular puncta formation and intracellular coexistence level were observed by confocal microscopy. The results are shown in FIGS. 6a to 6c. Immunofluorescence staining showed representative results from three or more independent experiments.

As shown in FIGS. 6a to 6c, it was confirmed that after treatment with the AUTOTAC chimeric compounds according to the present invention, intracellular puncta formation of p62 proteins, intracellular puncta formation of target proteins, and the local co-existence thereof were increased.

What is claimed is:
1. A compound selected from the group consisting of the following compounds 1 to 13:
   1) (2E,4E,6E,8E)-N-(2-(2-(2-(((R)-3-(3,4-bis(benzyloxy)phenoxy)-2-hydroxypropyl)amino)ethoxy)ethoxy)ethyl)-3,7-dimethyl-9-(2,6,6-trimethylcyclohex-1-en-1-yl)nona-2,4,6,8-tetraenamide;
   2) (2E,4E,6E,8E)-N-(2-(2-(2-((3,4-bis(benzyloxy) benzyl)amino)ethoxy)ethoxy)ethyl)-3,7-dimethyl-9-(2,6,6-trimethylcyclohex-1-en-1-yl)nona-2,4,6,8-tetraenamide;
   3) (R)—N-(15-(3,4-bis(benzyloxy)phenoxy)-14-hydroxy-3,6,9-trioxa-12-azapentadecyl)-4-phenylbutaneamide;
   4) N-(1-(3,4-bis(benzyloxy)phenyl)-5,8,11-trioxa-2-azatridecan-13-yl)-4-phenylbutanamide;
   5) 3-(3-(benzo[d][1,3]dioxol-5-yl)-1H-pyrazol-5-yl)-N-(2-(2-(2-((3-((4-fluorobenzyl)oxy)) benzyl)amino)ethoxy)ethoxy)ethyl)aniline;
   6) (3R,4S,5S,6R)-5-methoxy-4-((2R,3R)-2-methyl-3-(3-methylbut-2-en-1-yl)oxirane-2-yl)-1-oxaspiro[2.5]octan-6-yl(13E,15E,17E,19E)-1-(3-(benzyloxy)phenyl)-12-oxo-5,8-dioxa-2,11-diazahenicosa-13,15,17,19-tetraene-21-oate;
   7) 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione;
   8) (R)-1-(4-(benzyloxy)-3-(3-phenylpropoxy)phenoxy)-3-((2-(2-(2-(4-(2-phenyl-5,7-bis(trifluoromethyl)pyrazolo[1,5-a] pyrimidin-3-yl)phenoxy)ethoxy)ethoxy)ethyl)amino)propan-2-ol;
   9) (R,Z)-4-((2-(2-(2-((3-(3,4-diphenethoxyphenoxy)-2-hydroxypropyl)amino) ethoxy)ethoxy)ethyl)imino)-2-phenyl-4H-chromene-5,6,7-triol;
   10) (E)-5-(4-(2-(2-(2-((3,4-bis(benzyloxy)benzyl)amino)ethoxy)ethoxy)ethoxy)styryl)benzene-1,3-diol;
   11) (R)-2-(4-(benzo[d]thiazol-2-yl) phenyl)-14-(3,4-bis(benzyloxy)phenoxy)-5,8-dioxa-2,11-diazatetradecane-13-ol
   12) (1E,6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione; and
   13) (R)-1-(3-phenethoxyphenoxy)-3-((2-(2-(2-((6-(trifluoromethyl))benzo[d]thiazol-2-yl)amino)ethoxy)ethoxy)ethyl)amino)propan-2-ol,
or a pharmaceutically acceptable salt, stereoisomer, solvate, or hydrate thereof.

2. A composition comprising the compound according to claim 1, a pharmaceutically acceptable salt, stereoisomer, solvate, or hydrate thereof.

3. The composition according to claim 2, wherein the composition is a pharmaceutical composition.

4. A method for activating selective autophagy, comprising administering an effective amount of the compound of claim 1, a pharmaceutically acceptable salt, stereoisomer, solvate, or hydrate thereof to a subject in need thereof.

5. The method according to claim 4, wherein activating selective autophagy is increasing autophagic delivery or degradation of targets comprising pathological misfolded proteins, aggregates, organelles and/or pathogens thereof.

6. The method according to claim 4, wherein the activating selective autophagy is increasing degradation of viruses and bacteria that have invaded cells.

7. The method according to claim 4, wherein activating selective autophagy is delivering drugs or small molecule compounds in tandem with target proteins, organelles or pathogens to autophagic membranes.

8. The method according to claim 4, wherein the activation of selective autophagy is mediated by the autophagy target receptor p62/SQSTM1, comprising self-oligomerization, conformational activation and delivery to autophagic membranes.

9. The method according to claim 4, wherein activating selective autophagy is increased delivery of target proteins, organelles and/or pathogens to lysosomes by connecting these targets to p62.

10. The method according to claim 4, wherein the method comprises prevention, amelioration or treatment of cancer, or proteinopathy.

11. The method according to claim 10, wherein the proteinopathy is neurodegenerative diseases, alpha-1 antitrypsin deficiency, keratopathy, retinitis pigmentosa, type 2 diabetes, or cystic fibrosis.

12. The method according to claim 11, wherein the neurodegenerative diseases are selected from the group consisting of Lyme borreliosis, fatal familial insomnia, Creutzfeldt-Jakob Disease (CJD), multiple sclerosis (MS), dementia, Alzheimer's disease, epilepsy, Parkinson's disease, stroke, Huntington's disease, Picks disease, amyotrophic lateral sclerosis (ALS), spinocerebellar ataxias, other Poly-Q diseases, hereditary cerebral amyloid angiopathy, familial amyloid polyneuropathy, primary systemic amyloidosis (AL amyloidosis), reactive systemic amyloidosis (AA amyloidosis), injection-localized amyloidosis, beta-2 microglobulin amyloidosis, hereditary non-neuropathic amyloidosis, Alexander disease and Finnish hereditary systemic amyloidosis.

* * * * *